(12) United States Patent
Park et al.

(10) Patent No.: US 6,548,667 B2
(45) Date of Patent: Apr. 15, 2003

(54) SULFONAMIDE DERIVATIVE AS A MATRIX METALLOPROTEINASE INHIBITOR

(75) Inventors: Young-Jun Park, Taejon (KR); Hae-Young Bae, Taejon (KR); Ji-Uk Yoo, Taejon (KR); Myeong-Yun Chae, Taejon (KR); Sang-Hyun Paek, Taejon (KR); Hye-Kyung Min, Taejon (KR); Hyun-Gyu Park, Taejon (KR); Choon-Ho Ryu, Taejon (KR); Kyung-Chul Kim, Taejon (KR); Jeoung-Wook Lee, Taejon (KR)

(73) Assignee: Samsung Electronics Co. Ltd., Kyunggi-do (KR)

( * ) Notice: Subject to any disclaimer, the term of this patent is extended or adjusted under 35 U.S.C. 154(b) by 0 days.

(21) Appl. No.: 10/018,507

(22) PCT Filed: Apr. 7, 2001

(86) PCT No.: PCT/KR01/00585

§ 371 (c)(1),
(2), (4) Date: Dec. 6, 2001

(87) PCT Pub. No.: WO01/77092

PCT Pub. Date: Oct. 18, 2001

(65) Prior Publication Data

US 2002/0169314 A1 Nov. 14, 2002

(30) Foreign Application Priority Data

Apr. 7, 2000 (KR) ......................... 2000-18327
Apr. 7, 2000 (KR) ......................... 2000-18328
Apr. 8, 2000 (KR) ......................... 2000-18431

(51) Int. Cl.$^7$ ............... C07D 277/68; C07D 263/58; A61K 31/423

(52) U.S. Cl. ............. 544/62; 544/135; 544/137; 546/141; 546/198; 546/270.7; 546/271.7; 548/159; 548/169; 548/173; 548/165; 548/221

(58) Field of Search .................. 548/165, 221, 548/173, 169, 159; 544/135, 137, 62; 546/271.7, 270.7, 141, 198

(56) References Cited

FOREIGN PATENT DOCUMENTS

| WO | WO 98/03166 | 1/1998 |
| WO | WO 98/07742 | 2/1998 |
| WO | WO 98/09934 | 3/1998 |
| WO | WO 99/41246 | 8/1999 |
| WO | WO 99/52862 | 10/1999 |

OTHER PUBLICATIONS

Sorbera, L.A., et al. "Prinomastat," Drugs Fut., 25(2):150–158(2000).
Sorbera, L.A., et al. "AE–941," Drugs Fut., 25(6):551–557(2000).
Price, A., et al. "Marked Inhibition of Tumor Growth in a Malignant Glioma Tumor Model by a Novel Synthetic Matrix Metalloproteinase Inhibitor AG3340," Clin. Cancer Res., 5:845–854(1999).
O'Brien, P.M., et al., "Structure–Activity Relationships and Pharmacokinetic Analysis for a Series of Potent, Systemically Available Biphenylsulfonamide Matrix Metalloproteinase Inhibitors," J. Med. Chem., 43(2):156–166(2000).
Natchus, M.G., et al., "Development of New Carboxylic Acid–Based MMP Inhibitors Derived from Functionalized Propargylglycines," J. Med. Chem., 44(7):1060–1071(2001).
Scozzafava, A., et al., "Carbonic Anhydrase and Matrix Metalloproteinase Inhibitors: Sulfonylated Amino Acid Hydroxamates with MMP Inhibitory Properties Act as Efficient Inhibitors of CA Isozymes I, II, and IV, and N–Hydroxysulfonamides Inhibit Both These Zinc Enzymes," J. Med. Chem., 43(20):3677–3687(2000).
Scozzafava, A., et al., "Protease Inhibitors: Synthesis of Potent Bacterial Collagenase and Matrix Metalloproteinase Inhibitors Incorporating N–4–Nitrobenzylsulfonylglycine Hydroxamate Moieties," J. Med. Chem., 43(9):1858–1865(2000).
Barta, T.E., et al., "Synthesis and Activity of Selective MMP Inhibitors with an Aryl Backbone," Bioorg. Med. Chem. Lett., 10:2815–2817(2000).
Fray, M.J., et al., "Selectivity of Inhibition of Matrix Metalloproteases MMP–3 and MMP–2 by Succinyl Hydroxamates and Their Carboxylic Acid Analogues is Dependent P3' Group Chirality," Bioorg. Med. Chem. Lett., 11:567–570 (2001).
Fray, M.J., et al., "Discovery of Potent and Selective Succinyl Hydroxamate Inhibitors of Matrix Metalloprotease–3(Stromelysin–1)," Bioorg. Med. Chem. Lett., 11:571–574(2001).

(List continued on next page.)

Primary Examiner—Laura L. Stockton

(57) ABSTRACT

The present invention provides a novel sulfonamide derivative of general formula (I) useful as an inhibitor of matrix metalloproteinase (MMP), its isomers, pharmaceutically acceptable salts thereof and a process for preparing the same. Since the sulfonamide derivatives of the present invention selectively inhibit MMP activity in vitro, the MMP inhibitors comprising the sulfonamide derivatives as an effective ingredient can be practically applied for the prevention and treatment of all sorts of diseases caused by overexpression and overactivation of MMP.

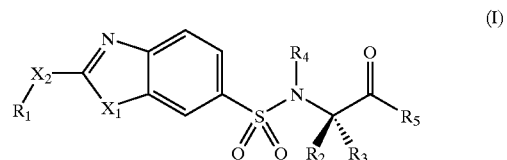

(I)

9 Claims, No Drawings

OTHER PUBLICATIONS

Levin, J.I., et al., "The Discovery of Anthranillic Acid–Based MMP Inhibitors. Part 1: SAR of the 3–Position," Bioorg. Med. Chem. Lett., 11:235–238(2001).

Levin, J.I., et al., "Hetroaryl and Cycloalkyl Sulfonamide Hydroxamic Acid Inhibitors of Matrix Metalloproteinases," Bioorg. Med. Chem. Lett., 11:239–242(2001).

Chollet, A.M., et al., "General Synthesis of α–Substituted 3–Bisarloxy Propionic Acid Derivatives as Specific MMP Inhibitors," Bioorg. Med. Chem. Lett., 11:295–299(2001).

Hudlicky, T., et al., "Chemoenzymatic Synthesis of Functionalized Cyclohexylglycines and α–Methylcyclohexylglycines via Kazmaier–Claisen Rearrangement," Bioorg. Med. Chem. Lett., 11:627–629(2001).

Whittaker, M., et al., "Design and Therapeutic Application of Matrix Metalloproteinase Inhibitors," Chem. Rev., 99(9):2735–2776(1999).

Hajduk, P.J., et al., "Discovery of Potent Nonpeptide Inhibitors of Stromelysin Using SAR by NMR," J. Am. Chem. Soc., 119(25):5818–5827(1997).

Hanessian, S., et al., "Design and Synthesis of MMP Inhibitors Using N–Arylsulfonylaziridine Hydroxamic Acids as Constrained Scaffolds," Tetrahedron, 57:6885–6900(2001).

Foley, L.H., et al., "Novel 5,5–Disubstitutedpyrimidine–2,4,6–triones as Selective MMP Inhibitors," Bioorg. Med. Chem. Lett., 11:969–972(2001).

Pikul, S., et al., "Heterocycle–Based MMP Inhibitors with P2' Substituents," Bioorg. Med. Chem. Lett., 11:1009–1013(2001).

Montana, J., et al., "The Design of Selective Non–Substrate– Based Matrix Metalloproteinase Inhibitors," Curr. Opin. Drug. Dis. Dev., 3(4):353–361(2000).

Brown, P.D., "Ongoing Trials with Matrix Metalloproteinase Inhibitors," Exp. Opin. Invest. Drugs, 9(9):2167–2177(2000).

Curtin, M.L., et al., "Discovery and Characterization of the Potent, Selective and Orally Bioavailable MMP Inhibitor ABT–770," Bioorg. Med. Chem. Lett., 11:1557–1560(2001).

Tullis, J.S., et al., "The Development of New Carboxylic Acid–Based MMP Inhibitors Derived from a Cyclohexylglycine Scaffold," Bioorg. Med. Chem. Lett., 11:1975–1979(2001).

Michaelides, M.R., et al., "Biaryl Ether Retrohydroxamates as Potent, Long–Lived, Orally Bioavailable MMP Inhibitors," Bioorg. Med. Chem. Lett., 11:1553–1556(2001).

Baxter, A.D., et al., "Arylsulphonyl Hydroxamic Acids: Potent and Selective Matrix Metalloproteinase Inhibitors," Bioorg. Med. Chem. lett., 11:1465–1468(2001).

Michaelides, M.., et al., "Recent Advances in Matrix Metalloproteinase Inhibitors Research," Curr. Pharm. Design, 5(10):787–819(1999).

Gasparini,G., "The Rationale and Future Potential of Angiogenesis Inhibitors in Neoplasia," Drugs,58(1):17–38(1999).

Koivunen, E., et al., "Tumor Targeting with a Selective Gelatinase Inhibitor," Nat. Biotechnol., 17:768–774(1999).

Caldarelli, M., et al., "Synthesis of an Array of Potential Matrix Metalloproteinase Inhibitors Using a Sequence of Polymer–Supported Reagents," Bioorg. Med. Chem. Lett., 9:2049–2052(1999).

Kiyama, R., et al., "Homology Modeling of Gelatinase Catalytic Domains and Docking Simulations of Novel Sulfonamide Inhibitors," J. Med. Chem., 42(10):1723–1738(1999).

Matter, H., et al., "Quantitative Structure–Activity Relationship of Human Neutrophil Collagenase (MMP–8) Inhibitors Using Comparative Molecular Field Analysis and X–ray Structure Analysis," J. Med. Chem., 42(11):1908–1920(1999).

Pikul, S., et al., "Discovery of Potent, Achiral Matrix Metalloproteinase Inhibitors," J. Med. Chem., 41(19):3568–3571(1998).

Pikul, S., et al., "Design and Synthesis of Phosphinamide–Based Hydroxamic ACids as Inhibitors of Matrix Metalloproteinases," J. Med. Chem., 42(1):87–94(1999).

Pfizer Products, Inc., "Arylsulphonamide Hydroxamic Acids as Potent Inhibitors MMP–13," Exp. Opin. Ther. Patents, 9(9):1303–1307(1999).

Davidson, A.H., et al., The Inhibition of Matrix Metalloproteinase Enzymes, Chem. Ind., 258–261(1997).

SULFONAMIDE DERIVATIVE AS A MATRIX METALLOPROTEINASE INHIBITOR

This is the U.S. National Phase under 35 U.S.C. §371 of International Application PCT/KR01/00585, filed Apr. 7, 2001 and published in the English language, which claims priority of KR 10-2000-0018327, filed Apr. 7, 2000; KR 10-2000-0018328, filed Apr. 7, 2000 and KR 10-2000-0018431, filed Apr. 8, 2000.

BACKGROUND OF THE INVENTION

1. Field of the Invention

The present invention relates to sulfonamide derivatives, more specifically, to novel sulfonamide derivatives represented as the following general formula (I), useful as matrix metalloproteinase inhibitor and pharmaceutically acceptable salts thereof and a process for preparing the compounds.

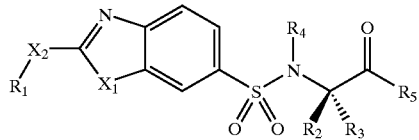

2. Description of the Prior Art

Matrix metalloproteinase ("MMP") is a $Ca^{2+}$-dependent proteinase containing zinc ion ($Zn^{2+}$) at its active site. At least, more than 18 matrix metalloproteinases including stromelycin, collagenase and a family of gelatinase have been identified. MMP degrades various extracellular matrix components of collagen, laminin, proteoglycan, fibronectin, elastin and gelatin under physiological conditions and, therefore, are effective on growth and tissue remodeling of articulation tissue, bone tissue, and connective tissue. The MMP contains $Zn^{2+}$ at its active site and has $Ca^{2+}$-dependent activity. They are secreted as an inactive form of proenzyme, which is subsequently activated in extracellular side, together with a naturally occuring inhibitor, TIMP (tissue inhibitor of metalloproteinase)

Meanwhile, MMP inhibitor is useful to prevention and treatment of all sorts of diseases caused by overexpression or overactivation of MMP. Such diseases are, for example, rheumatoid, arthrosteitis, unusual bone resorption, osteoporosis, periodontitis, interstitial nephritis, arteriosclerosis, pulmonary emphysema, cirrhosis, cornea injury, metastasis, invasion or growth of tumor cell, autoimmune disease, disease caused by vascular emigration or infiltration of leukocytes, arterialization (see: Beeley et al., Curr. Opin. Ther. Patents, 4(1):7–16, 1994). For instance, it was reported that synthetic MMP inhibitor has an anti-cancer activity in vivo along with inhibition of basement membrane remodeling in the mouse model bearing ovarian cancer (see: Cancer Res., 53:2087, 1993). Particularly, considering the fact that MMP-2 and MMP-9 among the above MMP enzymes play an essential role in angiogenesis required for the growth of cancer cells (see: Biochim. Biophys. Acta, 695, 1983), and that MMP-1 and MMP-3 among MMP enzymes play an important role in the progress of arthritis as observed in much higher concentration than normal in the synovium and cartilage of a patient of rheumatoid arthritis (see: Arthritis Rheum., 35:35–42, 1992), the selectivity to MMP-1/MMP-2 is considered to play a crucial role in reducing side effects such as arthralgia. Therefore, researches have been made while focusing on the development of selective inhibitors, and many MMP inhibitors have been designed and synthesized in many aspects (see: J. Enzyme Inhibitor, 2:1–22, 1987; Current Medicinal Chemistry, 2:743–762, 1995; Progress in Medicinal Chemistry, 29:271–334, 1992; Exp. Opin. Ther. Patents, 5:1287–1296, 1995; Drug Discovery Today, 1:16–26, 1996; Chem. Rev., 99:2735–2776, 1999).

Some compounds possessing inhibitory activity against MMP are known. In general, they have a zinc binding group ("ZBG"), which is coordinated to the zinc ion of MMP enzymes at the active site of them. Such ZBGs include hydroxamic acid, carboxylic acid, phosphoric acid, phosphinic acid, thiol and so forth (see: WO 92/09564; WO 95/04033; WO 00/04030; WO 00/43404; WO 95/13289; WO 96/11209; WO 95/09834; WO 95/09620; WO 00/40577; WO 00/40600; WO 98/03166; Chem. Rev. 99:2735–2776, 1999). Especially, several kinds of succinic acid derivatives based on substrate backbone have been designed and synthesized as a peptide-mimic inhibitor. (see: WO 99/25693; WO 98/43959; WO 98/24759; WO 98/30551; WO 98/30541; WO 97/32846; WO 99/01428; EP 897908; WO 98/38179; JP 95002797; WO 99/18074; WO 99/19296; EP 641323). The peptide-mimic inhibitors are known to contain a hydroxamic acid as a ZBG and display a broad spectrum for MMP enzymes.

However, some of the above peptide-mimic inhibitors are often poorly absorbed, exhibiting low oral bioavailability. They are also subject to rapid proteolytic metabolism, thus having short half-life. Furthermore, they possess lower selectivity to MMP-1/MMP-2 and induce the side effect of arthralgia in clinical trial (see: Current Pharmaceutical Design, 5:787–819, 1999; Current Opinion in Drug Discovery & Development, 3:353–361, 2000; Drugs of the Future, 21(12) :1215–1220, 1996).

In 1996, non-peptide inhibitors was developed to solve the said problems which are substantially distinguished in terms of chemical structure from the above peptide-mimic inhibitors having simple sulfonyl amino acid derivative represented as a chemical formula below (see: U.S. Pat. No. 5,506,242; J. Med. Chem., 40:2525–2532, 1997).

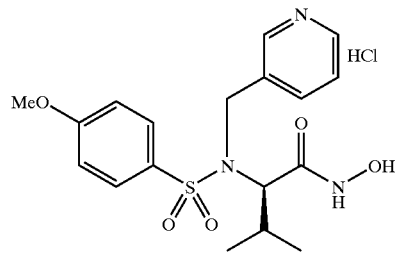

CGS-27023A(Novartis)

Under a consideration that the small molecule of sulfonamide-derived MMP inhibitors have strong activities in vitro against MMP enzymes, and have advantages over the said peptide-mimic inhibitors, a variety of sulfonamide inhibitors have been synthesized and reported in the literature (see: WO 98/50348; WO 97/20824; WO 00/09485; WO 99/58531; WO 99/51572; WO 99/52889; WO 99/52910; WO 99/37625; WO 98/32748; WO 99/18076; WO 99/06410; WO 99/07675; WO 98/27069; WO 97/22587; EP 979816; EP895988; EP 878467; EP 1041072) To improve in vitro enzymatic activity, selectivity, and pharmacokinetic profiles, new sulfonamide derivatives have been designed and synthesized, by changing P1' of the above sulfonamide inhibitor which binds to S1' sub-site of the enzymes.
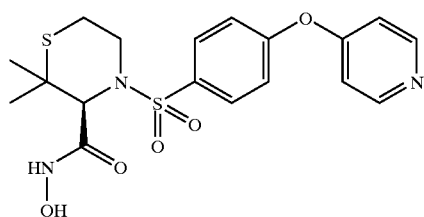
(Agouron, WO 9720824)
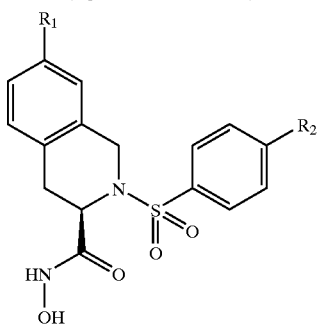
(Aventis, JP 98316662)
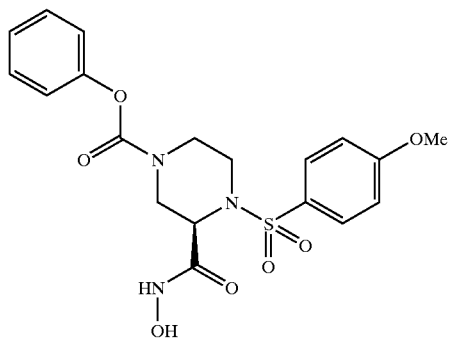
(P & G, WO 9808825)
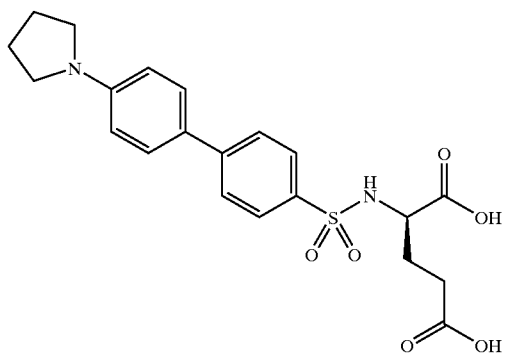
(Aventis, EP 877018)
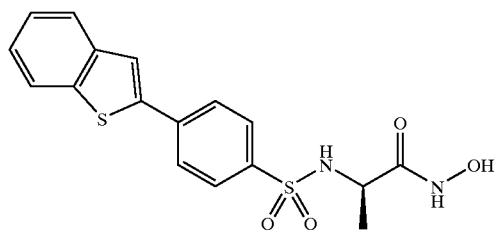
(Ono, JP 98204059)
-continued
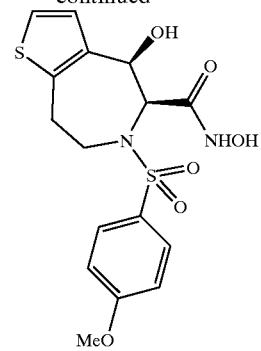
(Amgen, WO 9906410)
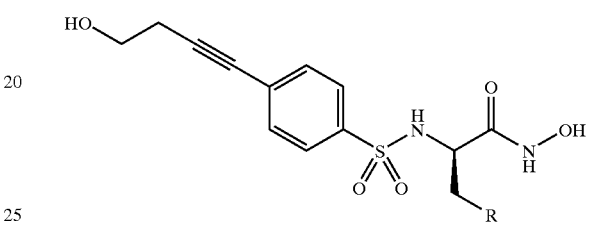
(Ono, JP 98204054)
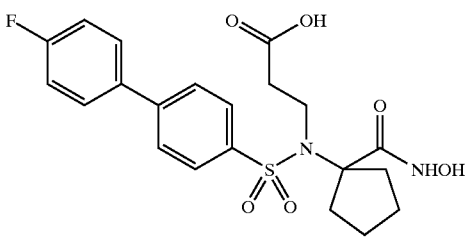
(Pfizer, EP 895988)
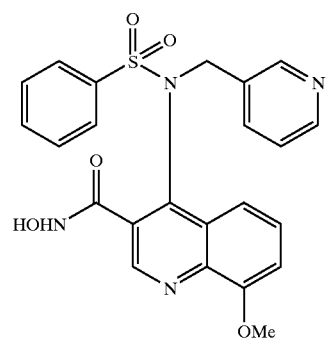
(AHP, EP 9918076)
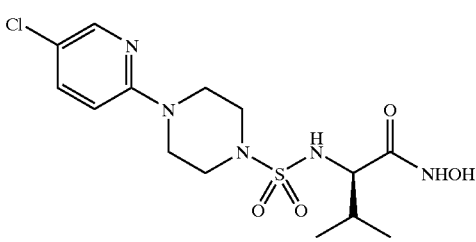
(Roche, WO 9832748)

-continued

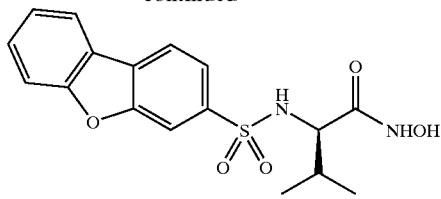

(Warner-Lambert, WO 9809934)

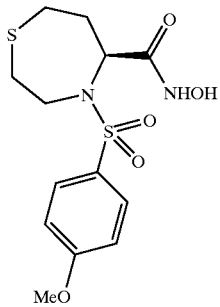

(P & G, WO 9808823)

However, while the above sulfonamide inhibitors have relatively high inhibitory activity against MMP, they do not have a higher selectivity to MMP-1/MMP-2 as compared with previous peptide-mimic inhibitors. Some of them have also side effect of arthralgia in clinical trials (see: Current Pharmaceutical Design, 5:787–819, 1999; Current Opinion in Drug Discovery & Development, 3:353–361, 2000; Exp. Opin. Invest. Drugs, 9:2159–2165, 2000; Drugs of the Future, 24(1):16–21, 1999). Although the sulfonamide inhibitors containing a hydroxamic acid as a ZBG typically showed a very strong in vitro inhibitory activity as compared with those containing a carboxylic acid as a ZBG, they also have revealed a limitation in oral administration due to their lower bioavailability and lower metabolic stability in vivo (see: J. Med. Chem., 41:640–649, 1988; Investigational New Drugs 16:303–313, 1999; Exp. Opin. Ther. Patents, 10:111–115, 2000; WO 00/63194; WO 00/27808; WO 99/18079; U.S. Pat. No. 6,117,869).

Under the circumstance, there are strong reasons for developing alternative compounds whose inhibitory action on MMP and the selectivity to MMP-1/MMP-2 are increased to reduce side effects.

SUMMARY OF THE INVENTION

The present inventors have made an effort to develop a new compound in which the inhibitory action on MMP and the selectivity to MMP-1/MMP-2 are increased to reduce side effects, and finally found that a new synthetic inhibitor of sulfonamide derivatives selectively inhibit MMP activity in vitro.

A primary object of the present invention is, therefore, to provide a sulfonamide derivative inhibiting MMP activity.

The other object of the invention is to provide a process for preparing the said derivative.

DETAILED DESCRIPTION OF THE INENTION

The present invention provides a sulfonamide derivative, which inhibits MMP activity, represented as the following general formula (I), the isomers and the pharmaceutically acceptable salts thereof, and a process for preparing the above compounds.

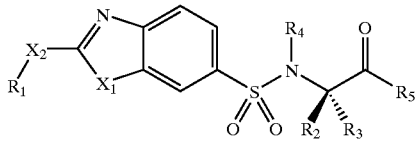

wherein, $R_1$ denotes hydrogen, $C_{1-12}$ alkyl, carbocyclic aryl-lower alkyl, $C_{3-7}$ cycloalkyl, $C_{3-7}$ cycloalkyl-lower alkyl, (oxo, amino or thio) $C_{3-7}$ cycloalkyl, (oxo, amino or thio) $C_{3-7}$ cycloalkyl-lower alkyl, $C_{2-12}$ lower alkenyl, $C_{2-12}$ lower alkynyl, carbocyclic aryl, heterocyclic aryl, heterocyclic aryl-lower alkyl, biaryl, halo lower alkyl, biaryl-lower alkylarylalkyl, hydroxy-lower alkyl, alkoxyalkyl, acyloxy-lower alkyl, alkyl or aryl (thio, sulfinyl or sulfonyl) lower alkyl, (amino, mono or dialkylamino) lower alkyl, acylamino lower alkyl, (N-lower alkyl-piperazino, or N-carbocyclic or heterocyclic aryl-lower alkyl piperazino)-lower alkyl or (morpholino, thiomorpholino, piperidino, pyrrolidino or piperidyl)-lower alkyl;

$R_2$ denotes hydrogen, lower alkyl, carbocyclic aryl-lower alkyl, $C_{1-4}$ carbocyclic aryl-lower alkyl, $C_{1-4}$ heterocyclic aryl-lower alkyl, $C_{1-5}$ alkoxyphenyl-lower alkyl, $C_{1-5}$ alkenoxyphenyl-lower alkyl, $C_{1-5}$ alkynoxyphenyl-lower alkyl, heterocyclic aryl-lower alkyl, hydroxy-lower alkyl, alkoxyalkyl, acyloxy-lower alkyl, thio-lower alkyl, alkyl or aryl-(thio, sulfinyl or sulfonyl) lower alkyl, (amino, mono or dialkylamino) lower alkyl, carboxyl-lower alkyl, (amino, mono or dialkylamino) lower alkyl or acylamino lower alkyl;

$R_3$ denotes hydrogen or $C_{1-6}$ lower alkyl;

$R_4$ denotes hydrogen, $C_{1-12}$ alkyl, $C_{3-7}$ cycloalkyl, $C_{3-7}$ cycloalkyl-lower alkyl, (oxo, amino or thio) $C_{3-7}$ cycloalkyl, (oxo, amino or thio) $C_{3-7}$ cycloalkyl-lower alkyl, carbocyclic aryl, carbocyclic aryl-lower alkyl, heterocyclic aryl, heterocyclic aryl-lower alkyl, biaryl, biaryl-lower alkyl, halo lower alkyl, hydroxy-lower alkyl, alkoxyalkyl, acyloxy-lower alkyl, alkyl or aryl-(thio, sulfinyl or sulfonyl) lower alkyl, (amino, mono or dialkylamino) lower alkyl, acylamino lower alkyl, carboxyl lower alkyl, (N-lower alkyl-piperazino, or N-carbocyclic or heterocyclic aryl piperazino)-lower alkyl or (morpholino, thiomorpholino, piperidino, pyrrolidino or piperidyl)-lower alkyl;

$R_5$ denotes hydroxy, alkoxy, halogen, thiol, thioalkoxy or hydroxylamine; and, $X_1$ and $X_2$ denote N—$R_7$ (wherein, $R_7$ is hydrogen, $C_{1-6}$ lower alkyl, aryl, heteroaryl or arylalkyl), S or O.

Otherwise mentioned, all kinds of isomers of the above sulfonamide compounds are fallen within the scope of the invention. For instance, in case of alkyl, alkoxy alkene and alkyne, compounds of the invention include isomers due to an asymmetric carbon atom as well as the straight- and branched-chains thereof.

The pharmaceutically acceptable salts of the invention include acid-added salts and hydrates. In general formula (I), the compound of the invention can be converted to the salts corresponding to them, preferably alkali metal salts (sodium, potassium, etc.), alkaline earth metal salts (calcium, magnesium, etc.), ammonium salts, non-toxic salts of pharmaceutical organic amine and water-soluble salts. The compound of the general formula (I) can be converted to inorganic acid salts (hydrochloride, hydrogen bromide, hydrogen iodide, sulfate, phosphate, nitrate, etc.) and organic acid salts (acetate, lactate, tartarate, oxalate, fumarate, glucuronate, etc.), preferably non-toxic salts and water-soluble salts. The compound of the general formula (I) and its salts can be also converted to the hydrates corresponding to them by the conventionally method in the art.

Among the compounds of general formula (I), a cyclic compound may be formed by the linkage of the above defined $R_2$ and $R_3$, which is represented as the general formula (I-1), and a cyclic compound formed by the linkage of $R_2$ and $R_4$, which is represented as the general formula (I-2).

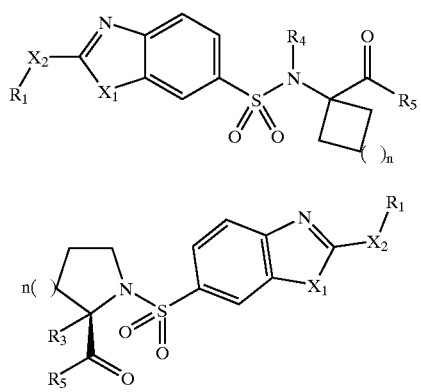

wherein,
$R_1$, $R_3$, $R_4$, $R_5$, $X_1$ and $X_2$ are the same as defined in the general formula (I) above; and,
n is an integer of 0 to 4.

Each of the above cyclic compounds can contain heteroatoms of one or two nitrogens, oxygens, sulfurs, etc.

Two processes for preparing the compounds of the general formula (I) are illustrated by the following steps, which may be applied to the preparation of the compounds, depending physical and chemical properties of $R_1$.

Process 1: In a case that $R_1$ does not have an aromatic ring and the carbon which is directly linked with $X_2$ is a primary carbon Step 1: Synthesis of Intermediate Compound (IV)

An amino acid derivative (III) is reacted with a sulfonyl halide (II) in an organic solvent in the presence of a base to give an intermediate compound(IV): The organic solvent includes most of non-protic solvents, preferably, dichloromethane or dichloroethane, and the base includes triethylamine or N-methylmorpholine.

Step 2: Introduction of $R_4$ Group

The intermediate compound (IV) is reacted with $R_4$-L (L: reactive leaving group) in an organic solvent in the presence of a base to give an intermediate compound (V): The organic solvent preferably includes DMF, THF or MeCN, and the base includes $K_2CO_3$, $NaHCO_3$, t-BuOH, NaH, etc.

Step 3: Deprotection of Intermediate Compound (V)

A protecting group of amino acid, $R_6$, is removed from the intermediate compound (V) by the hydrolysis in the presence of a base or an acid, or by subjecting in various conditions of H2/Pd—C, KF, etc. to give the compound of the general fomula (I): The base preferably includes NaOH, KOH, LiOH, $K_2CO_3$, etc. and the acid preferably includes HCl, $CF_3CO_2H$, etc. In the case that $R_6$ is silyl group, it is removed by heating the intermediate compound (V) in the presence of $F^-$ of HF, KF, TBAF, etc. or methanol. Optionally, a condensation reaction with hydroxylamine is carried out generally by activating the acid of intermediate compound (V), and reacting with hydroxylamine. The activation of the acid can be made by acid chloride method, mixed anhydride method, active ester method, etc. (see: J. Med. Chem., 40: 2525–2532, 1997; J. Med. Chem., 41:640–649, 1998).

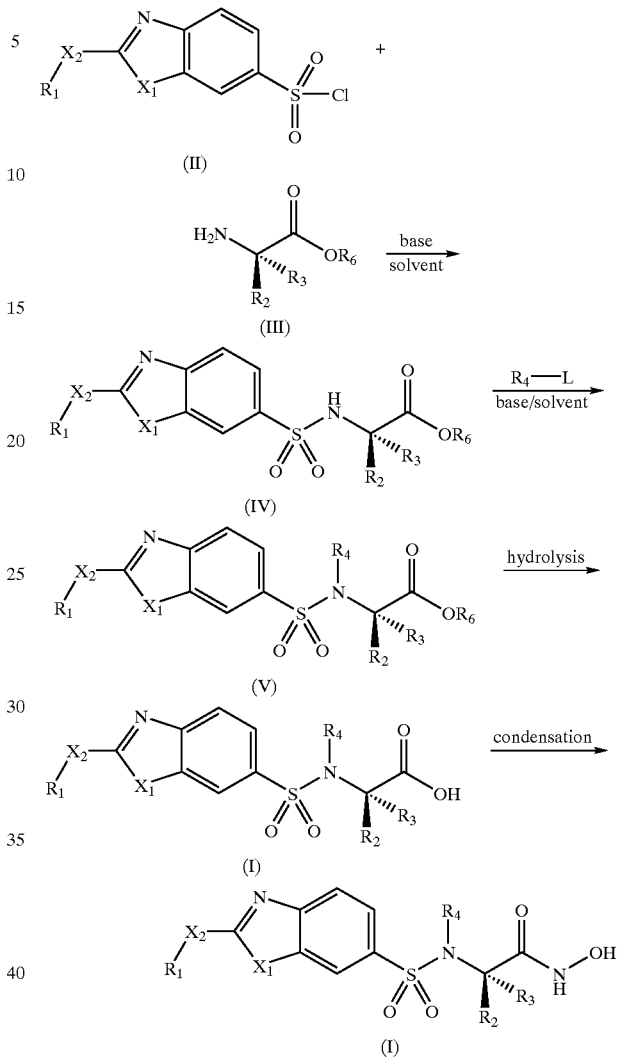

wherein,
$R_1$, $R_2$, $R_3$, $R_4$, $X_1$ and $X_2$ are the same as defined in the general formula (I) above; and,
$R_6$ is a substituent used as a protecting group of amino acid, such as hydrogen, methyl, ethyl, t-butyl, benzyl, diphenylmethyl or silyl group.

Meanwhile, sulfonyl halide (II) employed as a starting material is prepared as follows:

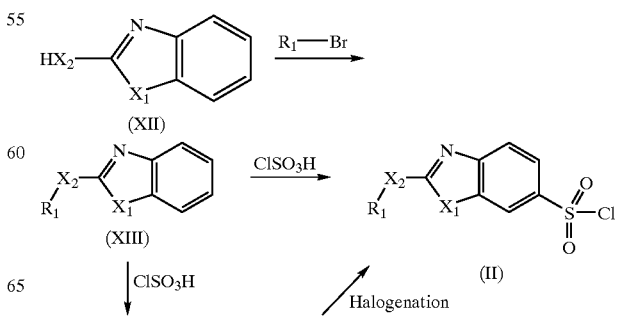

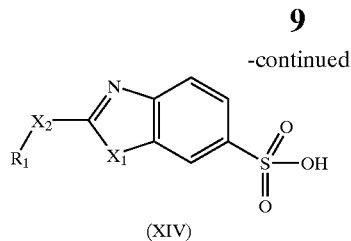

(XIV)

Step 1: Preparation of Compound (XIII)

A compound (XII) is subjected to substitution reaction with alkylhalide using an inorganic salt or organic salt at a room temperature to 100° C. in an organic solvent to prepare a compound (XIII): The compound (XII) preferably includes 2-mercaptobenzthiazol, 2-mercaptobenzoxazol, hydroxybenzthiazol, hydroxybenzoxazol, halobenzthiazol or halobenzoxazol, and the organic solvent is preferably a mixed solution of water and water-miscible organic solvents.

Step 2: Preparation of Sulfonyl Halide (II)

Chlorosulfonylation of a compound (XIII) is accomplished by the conventionally known methods below or the partially modified methods (see: U.S. Pat. No. 4,820,332, U.S. Pat. No. 5,504,098, U.S. Pat. No. 5,985,870, U.S. Pat. No. 5,559,081, EP 168264, U.S. Pat. No. 5,973,148, U.S. Pat. No. 5,962,490): For example, chlorosulfonylation of a compound (XIII) is made by reacting the compound (XIII) at a temperature of 50 to 130° C. in an organic solvent of dichloromethane, 1,2-dichloroethane, 1,1,2,2-tetrachloroethane, etc., or without organic solvent, in the presence of 2.5 to 5.0 volumes of chlorosulfonic acid. Also, in the reaction, though it is variable depending on the $R_1$, 2-substituted sulfonic acid (XIV) is obtained as a product along with 2-substituted sulfonylchloride (II) in the form of mixture. Without an isolating step, the mixture is treated with a chlorination reagent of $SOCl_2$, $POCl_3$, $PCl_3$, etc. to obtain 2-substituted sulfonylchloride (II) only, or the mixture is isolated by recrystallization to give a pure 2-substituted sulfonic acid (XIV) which is then treated with a chlorination reagent of $SOCl_2$, $POCl_3$, $PCl_3$, etc. to be converted into 2-substituted sulfonylchloride (II).

In the Process 1 above, if the compound (III-1) is employed instead of the amino acid derivative (III), a cyclic compound formed by the linkage of $R_2$ and $R_3$ is prepared as follows, where the compound (III-1) is obtained commercially or prepared by the conventionally known methods (see: WO 9952889; EP 1041072):

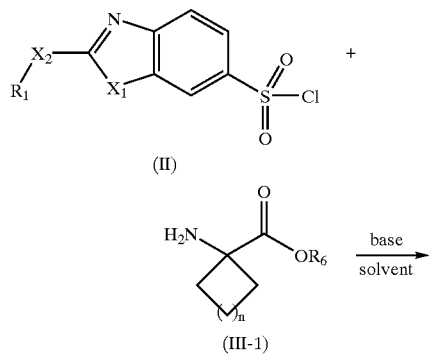

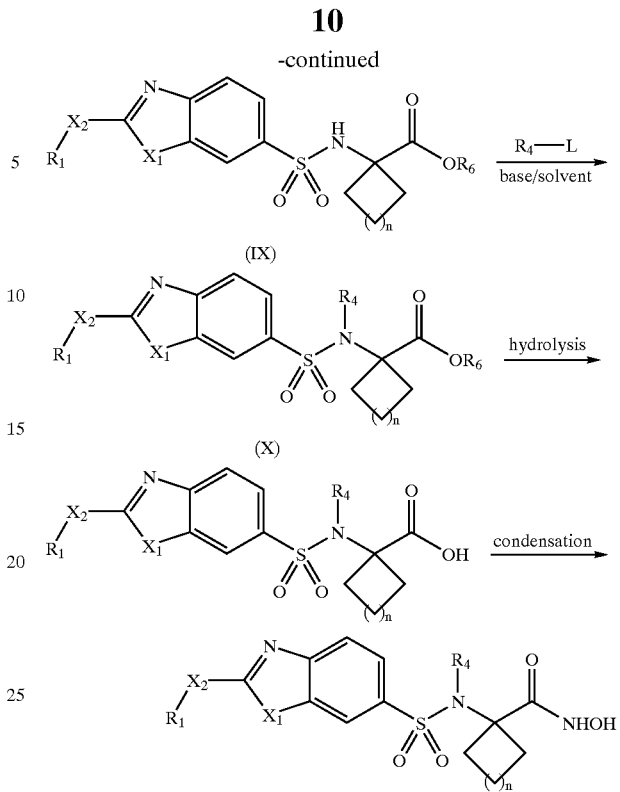

wherein, $R_1$, $R_4$, $X_1$, and $X_2$ are the same as defined in the general formula (I) above;

$R_6$ is a substituent used as a protecting group of amino acid, such as hydrogen, methyl, ethyl, t-butyl, benzyl, diphenylmethyl or silyl group; and, n is an integer of 0 to 4.

Also, if the compound (III-2) is employed instead of the amino acid derivative (III), a cyclic compound formed by the linkage of $R_2$ and $R_4$ is prepared as follows, where the compound (III-2) is obtained commercially or prepared by conventionally known methods (see: U.S. Pat. No. 5,861,510; U.S. Pat. No. 5,753,635; WO 97/20824; WO 98/08814; EP 803505; WO 98/08815; WO 98/08825; WO 98/08850; WO 98/50348; EP 878467):

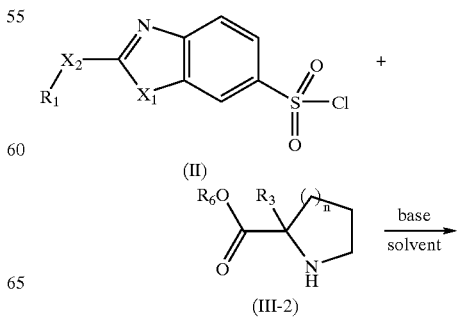

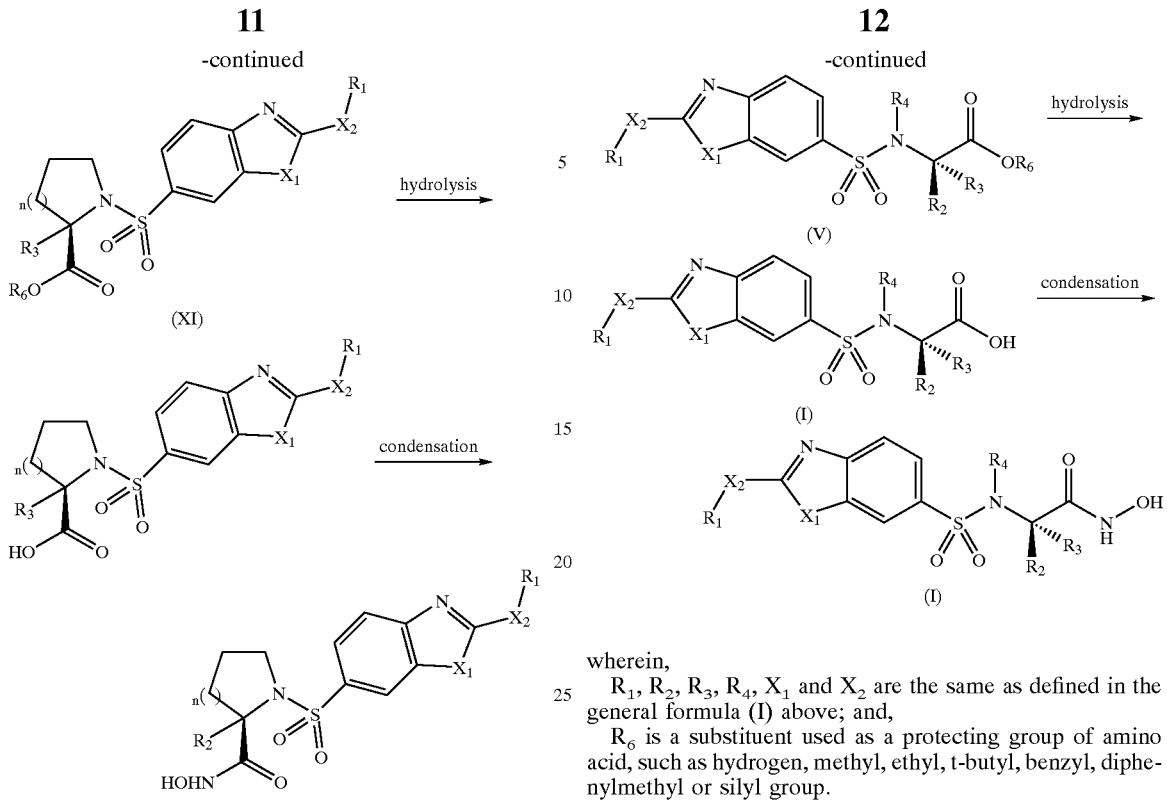

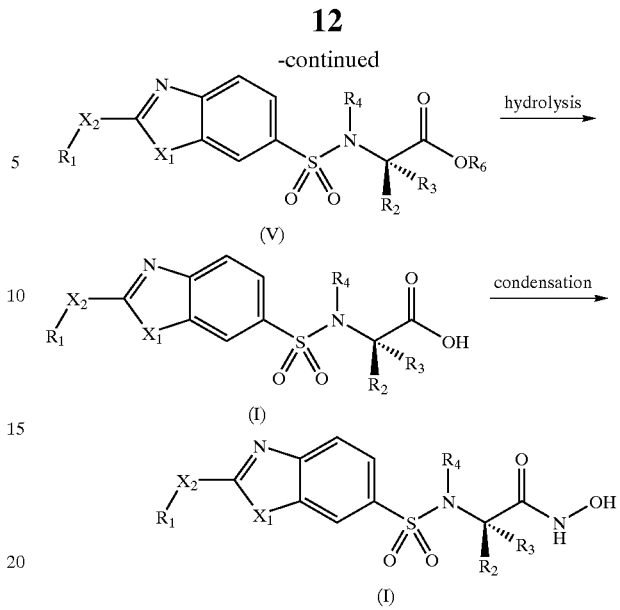

wherein,

R$_1$, R$_3$, X$_1$ and X$_2$ are the same as defined in the general formula (I) above;

R$_6$ is a substituent used as a protecting group of amino acid, such as hydrogen, methyl, ethyl, t-butyl, benzyl, diphenylmethyl or silyl group; and, n is an integer of 0 to 4.

Process 2: In a case that R$_1$ have an aromatic Ring, or the carbon which is directly linked with X$_2$ is a secondary carbon or contains a hetero atom

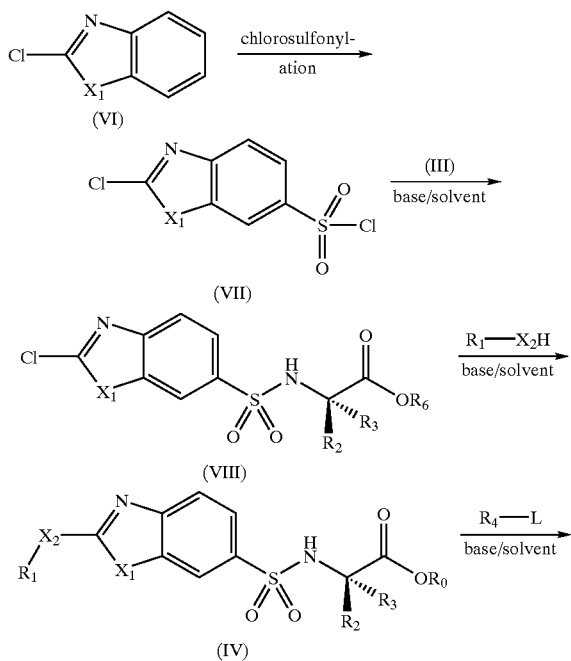

wherein,

R$_1$, R$_2$, R$_3$, R$_4$, X$_1$ and X$_2$ are the same as defined in the general formula (I) above; and, R$_6$ is a substituent used as a protecting group of amino acid, such as hydrogen, methyl, ethyl, t-butyl, benzyl, diphenylmethyl or silyl group.

Step 1: Synthesis of Sulfonylchloride

The compound (VI) is subjected to the chlorosulfonylation reaction to give a compound (VII).

Step 2: Synthesis of an Intermediate Compound (VIII)

An amino acid derivative (III) is reacted with the above compound (VII) in an organic solvent in the presence of a base to give an intermediate compound (VIII): The organic solvent includes almost all of non-protic solvents, preferably, dichloromethane or dichloroethane, and the base includes triethylamine or N-methylmorpholine.

Step 3: Substitution of the Intermediate Compound (VIII) with R$_1$—X$_2$H

The intermediate compound (VIII) is reacted with R$_1$—X$_2$H at a temperature of 70 to 80° C. in an organic solvent in the presence of a base to give an intermediate compound (IV): The organic solvent preferably includes MeCN, THF or DMF, and the base preferably includes K$_2$CO$_3$ or NaHCO$_3$.

Step 4: Introduction of R$_4$

The intermediate compound (IV) is reacted with R$_4$-L (L:reactive leaving group) in an organic solvent in the presence of a base to give an intermediate compound (V): The organic solvent preferably includes DMF, THF or MeCN, and the base includes K$_2$CO$_3$, NaHCO$_3$, t-BuOH, NaH, etc.

Step 5: Deprotection of Intermediate Compound (V)

A protecting group of amino acid, R$_6$, is removed from the intermediate compound (V) by the hydrolysis in the presence of a base or an acid or by subjecting in various conditions of H2/Pd—C, KF, etc. to give the compound of the general formula (I): The base preferably includes NaOH, KOH, LiOH, K$_2$CO$_3$, etc. and the acid preferably includes HCl, CF$_3$CO$_2$H, etc. In the case that R$_6$ is silyl group, it is removed by heating the intermediate compound (V) in the presence of F$^-$ of HF, KF, TBAF, etc. or methanol. Optionally, a condensation reaction with hydroxylamine is carried out generally by activating the acid of intermediate compound (V), and reacting with hydroxylamine. The activation of the acid can be made by acid chloride method, mixed anhydride method, active ester method, etc. (see: J. Med. Chem., 40: 2525–2532, 1997; J. Med. Chem., 41:640–649, 1998).

The present invention is further illustrated in the following examples, which should not be taken to limit the scope of the invention.

EXAMPLE 1

Preparation of 2-n-butylthio-6-benzthiazolsulfonyl Chloride 2-mercaptobenzthiazol (83.4 g, 0.5 mol) was dispersed in 100 mL of methanol, and added a solution containing 24 g of NaOH in 50 mL of $H_2O$. When 2-mercaptobenzthiazol was completely dissolved, n-butylbromide (54 mL, 0.5 mol) was added and the reaction solution was refluxed for 12 hours. Then, methanol was removed from the solution under reduced pressure and 300 mL of ethylacetate was added to the solution which was then washed with $H_2O$ and 1M $K_2CO_3$ in a sequential order. The separated organic solution was dried over $MgSO_4$ and then distilled under reduced pressure to give about 100 g of pure 2-n-butylthio-6-benzthiazol (89%), which was subsequentially transferred to a flask of 500 mL without further purification and cooled down to a temperature of 0° C. Chlorosulfonic acid (130 g, 2.5 equi.) was slowly added into the flask. The reaction solution was reacted for 24 hours at about 110° C. When starting material was completely exhausted, the reaction solution was cooled down to room temperature (RT) and stirred vigorously after adding ice water. Then, the solid product was obtained by filtering. The filtered solid was treated with ethylacetate (300 mL) followed by stirring for 1 hour. The undissolved solid was filtered and washed with ethylacetate to give 2-n-butylthio-6-benzthiazolsulfonic acid (30 g). The filtrated ethylacetate solution was treated with 5 g of activated carbon and $MgSO_4$ and stirred for 1 hour. Then, the ethylacetate solution was filtered on activated carbon and $MgSO_4$ again and dried under reduced pressure to remove the solvent, to give the titled compound, 2-n-butylthio-6-benzthiazolsulfonyl chloride (about 60 g) in a solid form. The titled compound was treated with n-hexane (150 mL), followed by stirring for 1 hour. After filtering, pure 2-n-butylthio-6-benzthiazolsulfonyl chloride (55 g) was obtained. A 30 mL of $SOCl_2$ as solvent and as reagent was added to 2-n-butylthio-6-benzthiazolsulfonic acid (30 g) obtained above. The reaction solution was refluxed for 5 hours, dried under reduced pressure, and then, treated with $H_2O$. The solid product was obtained by filtering. The solid was stirred with ethylacetate (100 mL) for 1 hour. The ethylacetate solution was treated with 5 g of activated carbon and $MgSO_4$ and stirred for 1 hour. The solution after filtering on activated carbon and $MgSO_4$ was dried under reduced pressure to remove the solvent, to give the titled compound, 2-n-butylthio-6-benzthiazolsulfonyl chloride (about 30 g) in a solid form. The compound was purified with n-hexane as described above, to give a pure 2-n-butylthio-6-benzthiazolsulfonyl chloride (25 g). Consquently, about 80 g of titled compound (about 56%) was prepared by two processes.

$^1$H NMR (300 MHz, $CDCl_3$): δ 1.1 (t, 3H), 1.5 (m, 2H), 1.8 (m, 2H), 3.4 (t, 2H), 8.0 (dd, 2H), 8.45 (s, 1H)

EXAMPLE 2

Preparation of 2-n-methylthio-6-benzthiazolsulfonyl Chloride

The titled compound, 2-n-methylthio-6-benzthiazolsulfonyl chloride was prepared in a similar manner as in Example 1, except for employing iodomethane.

$^1$H NMR (300 MHz, $CDCl_3$): δ 2.8 (s, 3H), 7.9 (dd, 2H), 8.2 (s, 1H)

EXAMPLE 3

Preparation of 2-n-ethylthio-6-benzthiazolsulfonyl Chloride

The titled compound, 2-n-ethylthio-6-benzthiazolsulfonyl chloride was prepared in a similar manner as in Example 1, except for employing bromoethane.

$^1$H NMR (300 MHz, $CDCl_3$): δ 1.5 (t, 3H), 3.4 (q, 2H), 7.85 (dd, 2H), 8.25 (s, 1H)

EXAMPLE 4

Preparation of 2-n-propylthio-6-benzthiazolsulfonyl Chloride

The titled compound, 2-n-propylthio-6-benzthiazolsulfonyl chloride was prepared in a similar manner as in Example 1, except for employing 1-bromopropane.

$^1$H NMR (300 MHz, $CDCl_3$): δ 1.1 (t, 3H), 1.9 (m, 2H), 3.4 (t, 2H), 8.0 (dd, 2H), 8.4 (s, 1H)

EXAMPLE 5

Preparation of 2-n-pentylthio-6-benzthiazolsulfonyl Chloride

The titled compound, 2-n-pentylthio-6-benzthiazolsulfonyl chloride was prepared in a similar manner as in Example 1, except for employing 1-bromopentane.

$^1$H NMR (300 MHz, $CDCl_3$): δ 0.95 (t, 3H), 1.4 (m, 4H), 1.9 (p, 2H), 3.4 (t, 2H), 7.9 (dd, 2H), 8.3 (s, 1H)

EXAMPLE 6

Preparation of 2-n-hexylthio-6-benzthiazolsulfonyl Chloride

The titled compound, 2-n-hexylthio-6-benzthiazolsulfonyl chloride was prepared in a similar manner as in Example 1, except for employing 1-bromohexane.

$^1$H NMR (300 MHz, $CDCl_3$): δ 0.9 (t, 3H), 1.35 (m, 4H), 1.5 (m, 2H), 1.85 (p, 2H), 3.4 (t, 2H), 8.0 (dd, 2H), 8.45 (s, 1H)

EXAMPLE 7

Preparation of 2-n-heptylthio-6-benzthiazolsulfonyl Chloride

The titled compound, 2-n-heptylthio-6-benzthiazolsulfonyl chloride was prepared in a similar manner as in Example 1, except for employing 1-bromoheptane.

$^1$H NMR (300 MHz, $CDCl_3$): δ 0.87 (t, 3H), 1.27 (m, 6H), 1.5 (m, 2H), 1.83 (p, 2H), 3.38 (t, 2H), 7.85 (dd, 2H), 8.24 (s, 1H)

EXAMPLE 8

Preparation of 2-n-octylthio-6-benzthiazolsulfonyl Chloride

The titled compound, 2-n-octylthio-6-benzthiazolsulfonyl chloride was prepared in a similar manner as in Example 1, except for employing 1-bromooctane.

$^1$H NMR (300 MHz, $CDCl_3$): δ 0.82 (t, 3H), 1.22 (m, 8H), 1.38 (m, 2H), 1.73 (m, 2H), 3.31 (t, 2H), 7.68 (dd, 2H), 8.22 (s, 1H)

EXAMPLE 9

Preparation of 2-n-dodecylthio-benzthiazolsulfonyl Chloride

The titled compound, 2-n-dodecylthio-6-benzthiazolsulfonyl chloride was prepared in a similar manner as in Example 1, except for employing 1-bromododecane.

$^1$H NMR (300 MHz, $CDCl_3$): δ 0.86 (t, 3H), 1.27 (m, 18), 1.8 (m, 2H), 3.4 (t, 2H), 8.0 (dd, 2H), 8.45 (s, 1H)

EXAMPLE 10
Preparation of 2-cyclohexylmethylthio-6-benzthiazolsulfonyl Chloride The titled compound, 2-cyclohexylmethylthio-6-benzthiazolsulfonyl chloride was prepared in a similar manner as in Example 1, except for employing cyclohexylmethylbromide.

$^1$H NMR (300 MHz, CDCl$_3$): δ 1.0 (m, 6H), 1.7(m, 3H), 1.9 (bd, 2H), 2.1 (m, 1H), 3.3 (d, 2H), 7.8 (dd, 2H), 8.25 (s,1H)

EXAMPLE 11
Preparation of 2-(3-cyclohexyl-1-propylthio)-6-benzthiazolsulfonyl Chloride The titled compound, 2-(3-cyclohexyl-1-propylthio)-6-benzthiazolsulfonyl chloride was prepared in a similar manner as in Example 1, except for employing 3-cyclohexyl-1-propylbromide.

$^1$H NMR (300 MHz, CDCl$_3$): δ 0.9 (m, 2H), 1.25 (m, 4H), 1.37 (m, 2H), 1.7 (m, 5H), 1.85 (m, 2H), 3.35 (t, 2H), 7.85 (dd, 2H), 8.25 (s, 1H)

EXAMPLE 12
Preparation of 2-n-propylthio-6-benzoxazolsulfonyl Chloride

The titled compound, 2-n-propylthio-6-benzoxazolsulfonyl chloride was prepared in a similar manner as in Example 1, except for employing 2-mercaptooxazol instead of 2-mercaptobenzthiazol as starting material and 1-bromopropane as halide.

$^1$H NMR (300 MHz, CDCl$_3$): δ 1.1 (t, 3H), 1.9 (m, 2H), 3,3 (t, 3H), 7.8(d, 1H), 8.1 (d, 1H), 8.2 (s, 1H)

EXAMPLE 13
Preparation of 2-chloro-6-benzthiazole Sulfonyl Chloride 2-chloro-6-benzthiazole (1.7 g, 10 mmol) was cooled down to 0° C. and treated with chlorosulfonic acid (3.3 mL) slowly. Then, the reaction solution was subjected at a temperature of 120° C. for 24 hours. When starting material was entirely exhausted, the reaction solution was cooled down to room temperature (RT) and stirred vigorously after adding ice water. Then, the product was extracted with ethylacetate. The organic phase was washed with H$_2$O, treated with 5 g of activated carbon and MgSO$_4$ and stirred for 1 hour. After removal of activated carbon and MgSO$_4$ by filtration, the filtrated solution was dried under reduced pressure to remove the solvent, to give the titled compound, 2-chloro-6-benzthiazolsulfonyl chloride. The compound was purified on silica gel chromatography by elution with n-hexane, to prepare the titled compound, 2-chloro-6-benzthiazolsulfonyl chloride (1.88 g, 70%) in a liquid form.

$^1$H NMR (300 MHz, CDCl$_3$): δ 7.9 (d, 1H), 8.0 (d, 1H), 8.3 (s, 1H)

EXAMPLE 14
Preparation of (2R)-3-methyl-2-[(2-methylthiobenzthiazol-6-sulfonyl)amino]butanoic Acid (D)-valine methylester hydrochloride (0.2 g, 1.19 mmol) was dispersed in dichloromethane (3 mL) and cooled down to 0° C. The reaction solution was treated with triethylamine (0.5 mL) and dichloromethane solution in which 2-n-methylthio-6-benzthiazolsulfonyl chloride (0.33 g, 1.0 equi.) prepared in Example 2 was dissolved in dichloromethane (2 mL) while maintaining the temperature of 0° C. When starting material was exhausted after 5 hours, the organic phase was washed with 1N HCl, dried over MgSO$_4$, distilled under reduced pressure and dried under vacuum, to prepare (2R)-3-methyl-2-[(2-methylthiobenzthiazol-6-sulfonyl)amino]butanoic acid methylester (0.35 g, 75%).

$^1$H NMR (300 MHz, CDCl$_3$): δ 0.88 (d, 3H), 0.95 (d, 3H), 2.0 (m, 1H), 2.8 (s, 3H), 3.4 (s, 3H), 3.8 (m, 1H), 5.2 (d, 1H), 7.9 (dd, 2H), 8.2 (s, 1H)

(2R)-3-methyl-2-[(2-methylthiobenzthiazol-6-sulfonyl)amino]butanoic acid methylester (0.35 g, 0.9 mmol) was dissolved in THF/H$_2$O (2 mL/2 mL), and added LiOH (0.16 g, 5 equi.). After the reaction soluton was refluxed for 6 hours, the solution was distilled under reduced pressure and treated with 1N HCl. The product was extracted with ethylacetate (10 mL). The separated organic phase was washed with NaCl solution, dried over MgSO$_4$, distilled under reduced pressure and dried under vacuum, to prepare the titled compound, (2R)-3-methyl-2-[(2-methylthiobenzthiazol-6-sulfonyl)amino]butanoic acid (54 mg, 23%).

$^1$H NMR (300 MHz, CDCl$_3$): δ 0.87 (d, 3H), 1.0 (d, 3H), 2.1 (m, 1H), 2.8 (s, 1H), 3,72 (m, 1H), 5,5 (d, 1H), 7.9 (m, 2H), 8.3 (s, 1H)

EXAMPLE 15
Preparation of (2R)-N-hydroxy-3-methyl-2-[(2-methylthiobenzthiazol-6-sulfonyl)amino]butyric Amide (2R)-3-methyl-2-[(2-methylthiobenzthiazol-6-sulfonyl)amino]butanoic acid (54 mg, 0.15 mmol) prepared in Example 14 was dissolved in dichloromethane (2 mL) and cooled down to 0° C., and added oxalylchloride (0.04 mL, 3 equi.) and DMF of catalytic amount. The reaction solution was subjected at room temperature for 3 hours. Then, the reaction solution was distilled and dried under reduced pressure to remove the solvent. And then, (2R)-3-methyl-2-[(2-methylthiobenzthiazol-6-sulfonyl) amino]butanoic chloride thus obtained was dissolved in THF (1 mL). Hydroxylamine hydrochloride (0.11 g, 10 equi.) and NaHCO$_3$ (0.15 g, 12 equi.) were dissolved in THF/H$_2$O (1 mL/1 ml) and cooled down to 0° C. The above acid chloride THF solution was slowly added to hydroxylamine solution while maintaining the temperature of 0° C. The solvent was removed from the reaction solution after 1 hour. Then, the product was extracted with ethylacetate (5 mL) and washed with H$_2$O and 0.1N HCl, dried over MgSO$_4$, distilled under reduced pressure and dried under vacuum, to prepare the titled compound, (2R)-N-hydroxy-3-methyl-2-[(2-methylthiobenzthiazol-6-sulfonyl)amino]butyric amide(50 mg, 90%).

$^1$H NMR (300 MHz, CDCl$_3$): δ 0.85 (d, 6H), 2.0 (m, 1H), 2.82 (s, 3H), 3.5 (m, 1H), 6,6 (d, 1H), 7.9 (s, 2H), 8.3 (s, 1H), 10.5 (bs, 1H)

EXAMPLE 16
Preparation of (2R)-3-methyl-2-[(ethylthio benzthiazol-6-sulfonyl)amino]butanoic Acid Using 2-n-ethylthio-6-benzthiazolsulfonyl chloride prepared above, the titled compound, (2R)-3-methyl-2-[(ethylthiobenzthiazol-6-sulfonyl)amino]butanoic acid was prepared in a similar manner as in Example 14.

$^1$H NMR (300 MHz, CDCl$_3$): δ 0.87 (d, 3H), 0.95 (d, 3H), 1.5 (t, 3H), 2.0 (m, 1H), 3.4 (q, 2H), 3.41 (s, 3H), 3.8 (m, 1H), 5.2 (d, 1H), 7.85 (dd, 2H), 8.25 (s, 1H)

EXAMPLE 17
Preparation of (2R)-N-hydroxy-3-methyl-2-[(2-ethylthiobenzthiazol-6 sulfonyl) amino]butyric Amide Using (2R)-3-methyl-2-[(2-ethylthiobenzthiazol-6-sulfonyl)amino]butanoic acid prepared in Example 16, the titled compound was prepared in a similar manner as in Example 15.

$^1$H NMR (300 MHz, DMSO-d$_6$): δ 0.72 (m, 6H), 1.4 (t, 3H), 1.75 (m, 1H), 3.30 (q, 2H), 7.77 (d, 1H), 7.93 (d, 1H), 8.05 (d, 1H), 8.4 (s, 1H), 8.7 (s, 1H), 10.5 (s, 1H)

EXAMPLE 18

The following titled compounds were prepared by the same process or slightly modified process depending on the properties of starting materials as described in Example 14 or 15.

Example 18-1
(2R)-3-methyl-2-[(2-n-propylthiobenzthiazol-6-sulfonyl)amino]butanoic Acid $^1$H NMR (300 MHz, CDCl$_3$): δ 0.9 (d, 3H), 1.0 (d, 3H), 1.1 (t, 3H), 1.86 (m, 2H), 2.1 (m, 1H), 3.3 (t, 2H), 3.8 (m, 1H), 5.3 (d, 1H), 7.85 (m, 2H), 8.3 (s, 1H)

Example 18-2
(2R)-N-hydroxy-3-methyl-2-[(2-n-propylthio benzthiazol-6-sulfonyl)amino]butyric Amide $^1$H NMR (300 MHz, CDCl$_3$): δ 0.8 (m, 6H), 1.1 (t, 3H), 1.87 (m, 2H), 2.0 (m, 1H), 3.36 (t, 2H), 3.5 (m, 1H), 5.5 (m, 1H), 7.87 (m, 2H), 8.3 (s, 1H), 9.5 (b, 1H)

Example 18-3
(2R)-3-methyl-2-[(2-n-butylthiobenz thiazol-6-sulfonyl)amino]butanoic Acid $^1$H NMR (300 MHz, CDCl$_3$): δ 0.9 (d, 3H), 0.98 (d, 3H), 1.0 (t, 3H), 1.53 (m, 2H), 1.83 (m, 2H), 2.1 (m, 1H), 3.33 (t, 2H), 3.83 (m, 1H), 5.3 (d, 1H), 7.86 (m, 2H), 8.3 (s, 1H)

Example 18-4
(2R)-N-hydroxy-3-methyl-2-[(2-n-butylthio benzthiazol-6-sulfonyl)amino]butyric Amide $^1$H NMR (300 MHz, CDCl$_3$): δ 0.8 (m, 6H), 1.0 (t, 3H), 1.5 (m, 2H), 1.8 (m, 2H), 2.05 (m, 1H), 3.4 (t, 2H), 3.6 (s, 1H), 5.7 (s, 1H), 7.9 (d, 2H), 8.3 (s, 1H), 9.3 (b, 1H)

Example 18-5
(2R)-3-methyl-2-[(2-n-pentylthiobenz-thiazol-6-sulfonyl)amino]butanoic Acid $^1$H NMR (300 MHz, CDCl$_3$): δ 0.9 (t, 3H), 0.91 (d, 3H), 1.01 (d, 3H), 1.43 (m, 4H), 1.84 (p, 2H), 2.1 (m, 1H), 3.3 (t, 2H), 3.8 (m, 1H), 5.3 (d, 1H), 7.8 (m, 2H), 8.3 (s, 1H)

Example 18-6
(2R)-N-hydroxy-3-methyl-2-[(2-n-pentylthiobenzthiazol-6-sulfonyl)amino]butyric Amide $^1$H NMR (300 MHz, DMSO-d$_6$): δ 0.71 (m, 6H), 0.86 (t, 3H), 1.36 (m, 4H), 1.76 (m, 3H), 3.35 (q, 2H), 7.8 (d, 2H),7.93 (d, 1H), 8.0 (d, 1H), 8.4 (s, 1H), 8.7 (s, 1H), 10.4 (s, 1H)

Example 18-7
(2R)-3-methyl-2-[(2-n-hexylthiobenzthiazol-6-sulfonyl)amino]butanoic Acid $^1$H NMR (300 MHz, CDCl$_3$): δ 0.9 (m, 6H), 1.0 (d, 3H), 1.33 (m, 4H), 1.48 (m, 2H), 1.83 (m, 2H), 2.12 (m, 1H), 3.33 (t, 2H), 3.83 (m, 1H), 5.18 (d, 1H), 7.86 (q, 2H), 8.28 (s, 1H)

Example 18-8
(2R)-N-hydroxy-3-methyl-2-[(2-n-hexylthiobenzthiazol-6-sulfonyl)amino]butyric Amide $^1$H NMR (300 MHz, DMSO-d$_6$): δ 0.72 (m, 6H), 0.85 (t, 3H), 1.3 (m, 4H), 1.45 (m, 2H), 1.8 (m, 3H), 7.7 (d, 1H),7.9 (d, 1H), 8.1 (s, 1H), 8.4 (s, 1H), 8.7 (s, 1H), 10.5 (s, 1H)

Example 18-9
(2R)-3-methyl-2-[(2-n-heptylthiobenzthiazol-6-sulfonyl)amino]butanoic acid $^1$H NMR (300 MHz, CDCl$_3$): δ 0.9 (m, 6H), 1.0 (d, 3H), 1.3 (m, 6H), 1.5 (m, 2H), 1.8 (m, 2H), 2.1 (m, 1H), 3.32 (t, 2H), 3.8 (m, 1H), 5.2 (d, 1H), 7.9 (m, 2H), 8.3 (s, 1H)

Example 18-10
(2R)-N-hydroxy-3-methyl-2[(2-n-heptylthiobenzthiazol-6-sulfonyl)amino]butyric Amide $^1$H NMR (300 MHz, CDCl$_3$): δ 0.8 (m, 9H), 1.27 (m, 6H), 1.45 (m, 2H), 1.7 (m, 2H), 1.9 (m, 2H), 3.34 (m, 2H), 3.5 (m, 1H), 6.5 (bd, 1H), 7.3 (d, 1H), 7.8 (s, 2H), 8.3 (s, 1H), 10.4 (s, 1H)

Example 18-11
(2R)-3-methyl-2-[(2-n-octylthio benzthiazol-6-sulfonyl)amino]butanoic Acid $^1$H NMR (300 MHz, CDCl$_3$): δ 0.9 (m, 6H), 1.0 (d, 3H), 1.3 (m, 8H), 1.5 (m, 2H), 1.8 (p, 2H), 2.1 (m, 1H), 3.3 (t, 2H), 4.75 (m, 1H), 5.2 (d, 1H), 7.86 (m, 2H), 8.28 (s, 1H)

Example 18-12
(2R)-N-hydroxy-3-methyl-2-[(2-n-octylthiobenzthiazol-6-sulfonyl)amino]butyric Amide $^1$H NMR (300 MHz, CDCl$_3$): δ 0.7~0.9 (m, 9H), 1.3 (m, 8H), 1.5 (m, 2H), 1.8 (m, 2H), 2.0 (m, 1H), 3.4 (t, 2H),3.5 (m, 1H), 5.5 (d, 1H), 7.9 (m, 2H), 8.3 (s, 1H), 10.1 (bs, 1H)

Example 18-13
(2R)-3-methyl-2-[(2-n-dodecylthiobenzthiazol-6-sulfonyl)amino]butanoic Acid $^1$H NMR (300 MHz, CDCl$_3$): δ 0.9 (m, 6H), 1.0 (d, 3H), 1.26 (m, 14H), 1.5 (m, 2H), 1.8 (p, 2H), 2.1 (m, 1H), 3.3 (t, 2H), 4.8 (m, 1H), 5.2 (d, 1H), 7.85 (m, 2H), 8.27 (s, 1H)

Example 18-14
(2R)-N-hydroxy-3-methyl-2-[(2-n-dodecyl thiobenzthiazol-6-sulfonyl)amino]butyric Amide $^1$H NMR (300 MHz, CDCl$_3$): δ 0.85 (m, 9H), 1.26 (m, 14H), 1.5 (m, 2H),1.8 (m, 2H), 2.0 (m, 1H), 3.37 (t, 2H), 3.6 (bs, 1H), 6.4 (d, 1H), 7.9 (s, 2H), 8.2 (s, 1H), 8.4 (s, 1H), 10.4 (s, 1H)

Example 18-15
(2R)-3-methyl-2-[(2-cyclohexylmethylthiobenzthiazol-6-sulfonyl)amino]butanoic Acid $^1$H NMR (300 MHz, CDCl$_3$): δ 0.9 (d, 3H), 1.0 (d, 3H), 1.0~1.3 (m, 5H), 1.7 (m, 4H), 1.9 (m, 2H), 2.1 (m, 1H), 3.22 (d, 2H), 3.8 (m, 1H), 5.4 (d, 1H), 7.85 (m, 2H), 8.27 (s, 1H)

Example 18-16
(2R)-N-hydroxy-3-methyl-2-[(2-cyclohexylmethylthiobenzthiazol-6-sulfonyl)amino]butyric Amide $^1$H NMR (300 MHz, CDCl$_3$): δ 0.85 (m, 6H), 1.1 (m, 2H), 1.27 (m, 3H), 1.78 (m, 4H), 1.95 (m, 3H), 3.3 (d, 2H), 3.6 (m, 1H), 6.4 (d, 1H), 7.86 (s, 2H), 8.3 (s, 1H), 10.3 (s, 1H)

Example 18-17
(2R)-3-methyl-2-[(2-(1-cyclohexyl-3 propyl) thiobenzthiazol-6-sulfonyl)amino]butanoic Acid $^1$H NMR (300 MHz, CDCl$_3$): δ 0.9 (m, 5H), 1.0 (d, 3H), 1.3 (m, 4H), 1.5 (m, 2H), 1.7 (m, 5H), 1.84 (m, 2H), 2.2 (m, 1H), 3.3 (t, 2H), 3.8 (m, 1H), 5.2 (d, 1H), 7.9 (m, 2H), 8.27 (s, 1H)

Example 18-18
(2R)-N-hydroxy-3-methyl-2-[(2-(1-cyclohexyl-3-propyl) thiobenzthiazol-6-sulfonyl)amino]butyric Amide $^1$H NMR(300 MHz, DMSO-d$_6$): δ 0.8 (m, 6H), 0.9 (m, 2H), 1.3 (m, 6H), 1.7 (m, 5H), 1.85 (m, 3H), 3.55 (t, 2H), 7.9 (d, 1H), 8.0 (d, 1H), 8.2 (d, 1H), 8.5 (s, 1H), 8.8 (s, 1H), 10.5 (s, 1H)

EXAMPLE 19
Preparation of (2R)-3-methyl-2-[(2-propylthiobenzoxazol-6-sulfonyl)amino]butanoic Acid (D)-valine methylester hydrochloride (0.2 g, 1.19 mmol) was dispersed in dichloromethane (3 mL) and cooled down to 0° C., and triethylamine (0.37 mL, 3 equi.) was added. The dichloromethane solution containing 2-n-propylthiobenzoxazol-6-sulfonyl chloride (0.26 g, 1.0 equi.) prepared in the above Example and dichloromethane (2 mL) was also added while maintaining the temperature of 0° C. When starting material was exhausted after 5 hours, the organic phase was washed with 1N HCl, dried over $MgSO_4$, distilled under reduced pressure and dried under vacuum, to give (2R)-3-methyl-2-[(2-propylthiobenzoxazol-6-sulfonyl)amino] butanoic acid methylester(0.31 g, 67%).

$^1$H NMR (300 MHz, $CDCl_3$): δ 0.86 (d, 3H), 0.95 (d, 3H), 1.1 (t, 3H), 1.87 (m, 2H), 2.05 (m, 1H), 3.32 (t, 2H), 3.43 (s, 3H), 3.78 (m, 1H), 5.15 (d, 1H), 7.64 (d, 1H), 7.76 (d, 1H), 7.8 (s, 1H)

(2R)-3-methyl-2-[(2-propylthiobenzthiazol-6-sulfonyl) amino]butanoic acid methylester (0.19 g, 0.48 mmol) was dissolved in $THF/H_2O$ (2 mL/2 mL), and LiOH (0.10 g, 5 equi.) was added. After reflux for 6 hours, the reaction solution was distilled under reduced pressure and treated with 1N HCl. The product was extracted with ethylacetate (10 mL). The separated organic phase was washed with NaCl solution, dried over $MgSO_4$, distilled under reduced pressure and dried under vacuum to prepare the titled compound, (2R)-3-methyl-2-[(2-propylthiobenzoxazol-6-sulfonyl)amino]butanoic acid (0.14 g, 77%).

$^1$H NMR (300 MHz, $CDCl_3$): δ 0.87 (d, 3H), 0.97 (d, 3H), 1.22 (t, 3H), 1.9 (m, 2H), 2.1 (m, 1H), 3.5 (q, 2H), 3.65 (m, 1H), 5.7 (d, 1H), 7.1 (d, 1H), 7.65 (m, 2H), 11,7 (s, 1H)

EXAMPLE 20
Preparation of (2R)-N-hydroxy-3-methyl-2-[(2-propylthiobenzoxasol-6-sulfonyl)amino]butyric Amide (2R)-3-methyl-2-[(2-propylthiobenzoxazol-6-sulfonyl) amino]butanoic acid (112 mg, 0.3 mmol) prepared in Example 19 was dissolved in dichloromethane (2 mL) and cooled down to 0° C., and, oxalylchloride (0.08 mL, 3 equi.) and DMF of catalytic amount were added. After the reaction was completed, the reaction solution was distilled under reduced pressure to remove the solvent and dried under reduced pressure. Then, (2R)-3-methyl-2-[(2-propylthiobenzoxazol-6-sulfonyl)amino]butanoic chloride thus obtained was dissolved in THF (1 mL). Hydroxylamine hydrochloride (0.21 g, 10 equi.) and $NaHCO_3$ (0.303 g, 12 equi.) was dissolved in $THF/H_2O$ (2 mL/2 mL) and cooled down to 0° C. to prepare a hydroxylamine solution. Then, acid chloride THF solution was slowly added to the hydroxylamine solution while maintaining the temperature of 0° C. After 1 hour, the solvent was removed from the reaction solution. Then, the product was extracted with ethylacetate (5 mL), washed with $H_2O$ and 0.1N HCl and dried over $MgSO_4$. The dried material was distilled under reduced pressure and vacuum-dried to prepare the titled compound, (2R)-N-hydroxy-3-methyl-2-[(2-propylthiobenzoxazol-6-sulfonyl)amino]butyric amide (100 mg, 85%).

$^1$H NMR(300 MHz, DMSO-$d_6$): δ 0.82 (m, 9H), 1.8 (m, 2H), 2.1 (m, 1H), 3.32 (t, 2H), 4.0 (m, 1H), 7.25 (d, 1H), 7.63 (m, 2H), 7.94 (d, 1H), 8.76 (s, 1H), 10.5 (s, 1H)

EXAMPLE 21
Preparation of (2R)-3-methyl-2-[(2-chlorobenzthiazol-6-sulfonyl)amino]butanoic Acid Methylester (D)-valine methylester hydrochloride (0.33 g, 2.0 mmol) was dispersed in dichloromethane (5 mL) and cooled down to 0° C. 2-Chloro-6-benzthiazolsulfonyl chloride (0.5 g, 1.0 equi.) prepared in Example 13 was dissolved in dichloromethane (3 mL) to give a dichloromethane solution. Triethylamine (0.83 mL, 3 equi.) and the dichloromethane solution were added while maintaining the temperature of 0° C. When starting material was exhausted after 5 hours, the organic phase was washed with 1N HCl, dried over $MgSO_4$ and distilled under reduced pressure. Then, the product was eluted and purified on silica gel chromatography using ethylacetate/n-hexane (1/3) solvent to prepare the titled compound, (2R)-3-methyl-2-[(2-chlorobenzthiazol-6-sulfonyl)amino] butanoic acid methylester (0.65 g, 90%).

$^1$H NMR (300 MHz, $CDCl_3$): δ 0.87 (d, 3H), 0.96 (d, 3H), 2.0 (m, 1H), 3.4 (s, 3H), 3.8 (m, 1H), 5.3 (bd, 1H), 7.9 (d, 1H), 8.0 (d, 1H), 8.33 (s, 1H).

EXAMPLE 22
Preparation of (2R)-3-methyl-2-[(2-phenylthiobenzthiazol-6-sulfonyl)amino]butanoic Acid Methylester (2R)-3-methyl-2-[(2-chlorobenzthiazol-6-sulfonyl) amino]butanoic acid methylester (0.154 mg, 0.44 mmol) prepared in a similar manner as in Example 20 was dissolved in MeCN (3 mL) and added solid $K_2CO_3$ (0.1 mg, 1.6 equi.). Thiophenol (0.055 mL, 1.2 equi.) was also added and the reaction solution was refluxed for 3 hours. When starting material was disappeared, $H_2O$/ethylacetate (5 mL/10 mL) was added for extraction of product. The extracted product in organic phase was washed with NaCl solution, dried over $MgSO_4$ and distilled under reduced pressure. The extracted product was crystallized with n-hexane/ethylacetate (3/1) solution to prepare the titled compound, (2R)-3-methyl-2-[(2-phenylthiobenzthiazol-6-sulfonyl)amino]butanoic acid methylester (190 mg, 99%).

$^1$H NMR (300 MHz, $CDCl_3$): δ 0.87 (d, 3H), 0.95 (d, 3H), 2.0 (m, 1H), 3.4 (s, 3H), 3.76 (m, 1H), 5.13 (d, 1H), 7.56 (m, 3H), 7.8 (m, 3H), 8.0 (d, 1H), 8.17 (s, 1H)

EXAMPLE 23

Example 23-1
Preparation of Derivative by Employing Thiophenol Derivative as Starting Material The following derivatives were prepared in a similar manner as in Example 22, except for employing thiophenol derivative as starting material.

(2R)-3-methyl-2-[(2-(4-methylphenyl)thiobenzthiazol-6-sulfonyl)amino]butanoic acid methylester (400 mg, 89%)

(2R)-3-methyl-2-[(2-(4-methoxyphenyl)thiobenzthiazol-6-sulfonyl)amino]butanoic acid methylester (420 mg, 89%)

(2R)-3-methyl-2-[(2-(4-bromophenyl)thiobenzthiazol-6-sulfonyl)amino]butanoic acid methylester (430 mg, 85%)

(2R)-3-methyl-2-[(2-(4-chlorophenyl)thiobenzthiazol-6-sulfonyl)amino]butanoic acid methylester(424 mg, 90%)

(2R)-3-methyl-2-[(2-(4-fluorophenyl)thiobenzthiazol-6-sulfonyl)amino]butanoic acid methylester (430 mg, 94%)

(2R)-3-methyl-2-[(2-(4-n-butylphenyl)thiobenzthiazol-6-sulfonyl)amino]butanoic acid methylester (260 mg, 80%)

Example 23-2
Preparation of Derivative by Employing Phenol Derivative as Starting Material The (2R)-3-methyl-2-[(2-phenoxybenzthiazol-6-sulfonyl)amino]butanoic acid methylester was prepared in a similar manner as in Example 22, except for employing phenol derivative as starting material.

$^1$H NMR (300 MHz, $CDCl_3$): δ 0.9 (d, 3H), 1.0 (d, 3H), 2.1 (m, 1H), 3.4 (s, 3H), 3.8 (m, 1H), 5.1 (d, 1H), 7.3 (m, 1H), 7.4 (d, 2H), 7.5 (d, 2H), 7.8 (m, 2H), 8.2 (s, 1H)

Example 23-3
Preparation of Derivative by Employing Benzylthiol Derivative as Starting Material The following compounds were prepared in a similar manner as in Example 22, except for employing benzylthiol derivative as starting material.

(2R)-3-methyl-2-[(2-(4-methoxyphenyl)methylthiobenzthiazol-6-sulfonyl)amino]butanoic acid methylester (1.5 g, 75%)

$^1$H NMR (300 MHz, CDCl$_3$): δ 0.87 (d, 3H), 0.95 (d, 3H), 2.04 (m, 1H), 3.37 (s, 3H), 3.8 (s, 3H), 4.6 (s, 2H), 5.2 (d, 1H), 6.86 (d, 2H), 7.37 (d, 2H), 7.85(d, 1H), 7.9 (d, 1H), 8.2 (s, 1H)

(2R)-3-methyl-2-[(2-benzylthiobenzthiazol-6-sulfonyl)amino]butanoic acid methylester (310 mg, 75%)

(2R)-3-methyl-2-[(2-(4-chlorophenyl)methylthiobenzthiazol-6-sulfonyl)amino]butanoic acid methylester (400 mg, 83%)

Example 23-4
Preparation of Derivative by Employing Benzylalkylthiol Derivative as Starting Material The (2R)-3-methyl-2[(2-(3-phenylethylthio)benzthiazol-6-sulfonyl)amino]butanoic acid methylester (320 mg, 75%) was prepared in a similar manner as in Example 22, except for employing benzalkylthiol derivative as starting material.

Example 23-5
Preparation of Derivative by Employing Aliphatic Cyclicthiol Derivative as Starting Material The (2R)-3-methyl-2-[(2-cyclopentylthiobenzthiazol-6-sulfonyl)amino]butanoic acid methylester (214 mg, 50%) was prepared in a similar manner as in Example 22, except for employing aliphatic cyclicthiol derivative as starting material.

Example 23-6

Preparation of Derivative by Employing Haloalkylthiol Derivative as Starting Material The (2R)-3-methyl-2-[(2-(3-chloro-1-propylthio)benzthiazol-6-sulfonyl)amino]butanoic acid methylester (240 mg, 55%) was prepared in a similar manner as in Example 22, except for employing haloalkylthiol derivative as starting material.

EXAMPLE 24
Preparation of (2R)-3-methyl-2-[(2-(4-methylphenyl)thiobenzthiazol-6-sulfonyl) amino]butanoic Acid and Derivative (2R)-3-methyl-2-[(2-((4-methylphenyl)thiobenzthiazol-6-sulfonyl)amino]butanoic acid methylester (0.3 g, 0.66 mmol) prepared in Example 23 was dissolved in THF/H$_2$O (2 mL/2 mL). LiOH (0.14 g, 5 equi.) was added and the reaction solution was refluxed for 6 hours. Then, the solution was distilled under reduced pressure and treated with 1N HCl. The organic phase containing product was extracted with ethylacetate (10 mL), washed with NaCl solution, dried over MgSO$_4$, distilled and dried under vacuum to prepare the compound, (2R)-3-methyl-2-[(2-(4-methylphenyl)thiobenzthiazol-6-sulfonyl)amino]butanoic acid (0.23 g, 80%).

$^1$H NMR (300 MHz, CDCl$_3$): δ 0.85 (d, 3H), 0.97 (d, 3H), 2.1 (m, 1H), 2.5 (s, 3H), 3.6 (m, 1H), 5.4 (d, 1H), 7.34 (d, 2H), 7.62(d, 2H), 7.86 (m, 2H), 8.16 (s, 1H)

The following final materials were prepared under the above hydrolysis condition by employing material prepared in Example 23.

Example 24-1
(2R)-3-methyl-2-[(2-phenylthiobenzthiazol-6-sulfonyl)amino]butanoic Acid $^1$H NMR (300 MHz, CDCl$_3$): δ 0.86 (d, 3H), 0.95 (d, 3H), 2.0 (m, 1H), 3.6 (m, 1H), 5.3 (d, 1H), 7.56 (m, 3H), 7.8 (m, 3H), 8.0 (d, 1H), 8.17 (s, 1H)

Example 24-2
(2R)-3-methyl-2-[(2-(4-methoxyphenyl) thiobenzthiazol-6-sulfonyl)amino]butanoic Acid $^1$H NMR (300 MHz, CDCl$_3$): δ 0.92 (d, 3H), 1.0 (d, 3H), 2.1 (m, 1H), 3.7 (m, 1H), 3.9 (s, 3H), 5.3 (d, 1H), 7.0 (d, 2H), 7.6 (d, 2H), 7.8 (s, 2H), 8.17 (s, 1H)

Example 24-3
(2R)-3-methyl-2-[(2-(4-bromophenyl)thiobenzthiazol-6-sulfonyl)amino]butanoic Acid $^1$H NMR (300 MHz, CDCl$_3$): δ 0.8 (bm, 6H), 2.1 (bm, 1H), 3.7 (m, 1H), 7.6 (dd, 4H), 7.8 (s, 2H), 8.2 (s, 1H)

Example 24-4
(2R)-3-methyl-2-[(2-(4-chlorophenyl)thio benzthiazol-6-sulfonyl)amino]butanoic Acid $^1$H NMR (300 MHz, CDCl$_3$): δ 0.8 (d, 3H), 0.92 (d, 3H), 2.1 (m, 1H), 3.6 (m, 1H), 5.5 (d, 1H), 7.1 (d, 2H), 7.6 (d, 2H), 7.8 (m, 2H), 8.2 (s, 1H)

Example 24-5
(2R)-3-methyl-2-[(2-(4-fluorophenyl)thio benzthiazol-6-sulfonyl)amino]butanoic Acid $^1$H NMR (300 MHz, CDCl$_3$): δ 0.9 (d, 3H), 1.0 (d, 3H), 2.1 (m, 1H), 3.8 (m, 1H), 5.25 (d, 1H), 7.24 (d, 2H), 7.72 (m, 2H), 7.87 (m, 2H), 8.20 (s, 1H)

Example 24-6
(2R)-3-methyl-2-[(2-((4-n-butylphenyl)thio benzthiazol-6-sulfonyl)amino]butanoic Acid $^1$H NMR (300 MHz, CDCl$_3$): δ 0.9~1.0 (m, 9H), 1.4 (m, 2H), 1.6 (m, 2H), 2.1 (m, 2H), 2.7 (t, 2H), 3.7 (m, 1H), 5.3 (d, 1H), 7.34 (d, 2H), 7.60 (d, 2H), 7.85 (m, 2H), 8.18 (s, 1H)

Example 24-7
(2R)-3-methyl-2-[(2-phenoxybenzthiazol-6-sulfonyl)amino]butanoic Acid $^1$H NMR (300 MHz, CDCl$_3$): δ 0.9 (d, 3H), 1.0 (d, 3H), 2.1 (m, 1H), 3.8 (m, 1H), 5.2 (d, 1H), 7.6 (m, 3H), 7.75 (d, 2H), 7.9 (m, 2H), 8.2 (s, 1H)

Example 24-8
(2R)-3-methyl-2-[(2-(4-methoxyphenyl)methylthiobenzthiazol-6-sulfonyl)amino]butanoic Acid $^1$N NMR (300 MHz, CDCl$_3$): δ 0.88 (d, 3H), 1.0 (d, 3H), 2.1 (m, 1H), 3.8 (s, 3H), 4.53 (s, 2H), 5.24 (d, 1H), 6.87 (d, 2H), 7.35 (d, 2H), 7.87 (dd, 2H), 8.27 (s, 1H)

Example 24-9
(2R)-3-methyl-2-[(2-benzylthiobenzthiazol-6-sulfonyl)amino]butanoic Acid $^1$H NMR (300 MHz, CDCl$_3$): δ 0.88 (d, 3H), 1.0 (d, 3H), 2.1 (m, 1H), 3.8 (m, 1H), 4.58 (s, 2H), 5.25 (d, 1H), 7.33 (m, 3H), 7.45 (m, 2H), 7.87 (dd, 2H), 8.28 (s, 1H)

Example 24-10
(2R)-3-methyl-2-[(2-(4-chlorophenyl)methylthiobenzthiazol-6-sulfonyl)amino]butanoic Acid $^1$H NMR (300 MHz, CDCl$_3$): δ 0.88 (d, 3H), 1.0 (d, 3H), 2.1 (m, 1H), 3.8 (m, 1H), 4.56 (s, 2H), 5.2 (d, 1H), 7.3 (d, 1H), 7.4 (d, 1H), 7.88 (dd, 2H), 8.28 (s, 1H)

Example 24-11
(2R)-3-methyl-2-[(2-(3-phenylethylthio) benzthiazol-6-sulfonyl)amino]butanoic Acid $^1$H NMR (300 MHz, CDCl$_3$): δ 0.88 (d, 3H), 0.98 (d, 3H), 2.1 (m, 1H), 3.13 (t, 2H), 3.56 (t, 2H), 3.8 (m, 1H), 5.25 (d, 1H), 7.28 (m, 3H), 7.32 (m, 2H), 7.86 (m, 2H), 8.27 (s, 1H)

Example 24-12
(2R)-3-methyl-2-[(2-cyclopentylthiobenzthiazol-6-sulfonyl)amino]butanoic Acid $^1$H NMR (300 MHz, CDCl$_3$): δ 0.91 (d, 3H), 1.0 (d, 3H), 1.77 (m, 8H), 2.3 (m, 1H), 3.8 (m, 1H), 4.05 (m, 1H), 5.2 (d, 1H), 7.86 (m, 2H), 8.28 (s, 1H)

Example 24-13
(2R)-3-methyl-2-[(2-(3-chloro-propylthio) benzthiazol-6-sulfonyl)amino]butanoic Acid $^1$H NMR (300 MHz, CDCl$_3$): δ 0.89 (d, 3H), 1.0 (d, 3H), 1.8 (m, 2H), 2.3 (m, 1H), 3.55 (t, 2H), 3.75 (t, 2H), 3.9 (m, 1H), 5.2 (d, 1H), 7.8 (m, 2H), 8.28 (s, 1H)

EXAMPLE 25
Preparation of (2R)-N-hydroxy-3-methyl-2-[(2-((4-methylphenyl)thiobenzthiazol-6-sulfonyl)amino]butyric Amide and its Derivatives (2R)-3-methyl-2-[(2-((4-methylphenyl)thiobenzthiazol-6-sulfonyl)amino]butanoic acid (84 mg, 0.19 mmol) prepared in Example 24 was dissolved in dichloromethane (2 mL) and cooled down to 0° C. Then, oxalylchloride (0.05 mL, 3 equi.) and DMF of catalytic amount were added. After reaction for 3 hours at RT, the reaction solution was distilled under reduced pressure to remove the solvent and dried under reduced pressure again to prepare (2R)-3-methyl-2-[(2-((4-methylphenyl)thiobenzthiazol-6-sulfonyl)amino]butanoic chloride. Then, the compound was dissolved in THF (1 mL) Hydroxylamine hydrochloride (0.13 g, 10 equi.) and NaHCO$_3$ (0.194 g, 12 equi.) were dissolved in THF/H$_2$O (2 mL/2 mL) and cooled down to 0° C. to give a hydroxylamine solution. Acid chloride THF solution was slowly added to hydroxylamine solution while maintaining the temperature of 0° C. After 1 hour, the solvent was removed from the reaction solution. Then, the product was extracted with ethylacetate(5 mL), washed with H$_2$O and 0.1N HCl, dried over MgSO$_4$, distilled under reduced pressure and vacuum-dried finally to prepare the titled compound, (2R)-N-hydroxy-3-methyl-2-[(2-((4-methylphenyl) thiobenzthiazol-6-sulfonyl)amino]butyric amide (80 mg, 92%).

$^1$H NMR (300 MHz, DMSO-d$_6$): δ 0.7 (m, 6H), 1.7 (m, 1H), 2.4 (s, 3H), 3.2 (m, 1H), 7.41 (d, 2H), 7.7 (d, 2H), 7.8 (d, 1H), 7.9 (d, 1H), 8.0 (d, 1H), 8.3 (s, 1H), 8.7 (s, 1H), 10.5 (s, 1H)

The following compounds were prepared under the condition of the above chlorination and hydroxyamine hydrochloride (10 equi.) and NaHCO$_3$ (12 equi.) by employing the acid prepared in Example 24.

Example 25-1
(2R)-N-hydroxy-3-methyl-2-[(2-phenylthiobenzthiazol-6-sulfonyl)amino]butane Amide $^1$H NMR (300 MHz, CDCl$_3$): δ 0.83 (m, 6H), 2.0 (m, 1H), 3.53 (m, 1H), 6.4 (m, 1H), 7.3 (s, 1H), 7.56 (m, 3H), 7.76 (m, 2H), 7.89 (m, 2H), 8.2 (s, 1H), 10.3 (s, 1H)

Example 25-2
(2R)-N-hydroxy-3-methyl-2-[(2-((4-methoxyphenyl) thiobenzthiazol-6-sulfonyl) amino]butyric Amide $^1$H NMR (300 MHz, DMSO-d$_6$): δ 0.7 (m, 6H), 1.7 (m, 1H), 3.2 (m, 1H), 3.84 (s, 3H), 7.15 (d, 2H), 7.75 (m, 3H), 7.88 (d, 1H), 8.0 (m, 1H), 8.3 (s, 1H), 8.73 (s, 1H), 10.5 (s, 1H)

Example 25-3
(2R)-N-hydroxy-3-methyl-2-[(2-((4-bromophenyl) thiobenzthiazol-6-sulfonyl) amino]butyric Amide $^1$H NMR(300 MHz, DMSO-d$_6$): δ 0.73 (m, 6H), 1.7 (m, 1H), 3.24 (m, 1H), 7.16 (d, 2H), 7.60 (d, 2H), 7.84 (d, 1H), 7.9 (s, 2H), 8.73 (s, 1H), 10.4 (s, 1H)

Example 25-4
(2R)-N-hydroxy-3-methyl-2-[(2-((4-chlorophenyl) thiobenzthiazol-6-sulfonyl)amino]butyric Amide $^1$H NMR (300 MHz, DMSO-d$_6$): δ 0.73 (m, 6H), 1.7 (m, 1H), 3.24 (m, 1H), 7.18 (d, 2H), 7.64 (d, 2H), 7.87 (d, 1H), 7.95 (s, 2H), 8.75 (s, 1H), 10.47 (s, 1H)

Example 25-5
(2R)-N-hydroxy-3-methyl-2-[(2-((4-fluorophenyl) thiobenzthiazol-6-sulfonyl)amino]butyric Amide $^1$H NMR (300 MHz, DMSO-d$_6$): δ 0.74 (m, 6H), 1.7 (m, 1H), 3.3 (m, 1H), 7.19 (d, 2H), 7.65 (m, 2H), 7.92 (d, 1H), 7.96 (s, 2H), 8.76 (m, 1H), 10.47 (s, 1H)

Example 25-6
(2R)-N-hydroxy-3-methyl-2-[(2-((4-n-butylphenyl) thiobenzthiazol-6-sulfonyl)amino]butyric Amide $^1$H NMR (300 MHz, CDCl$_3$): δ 0.8 (m, 6H), 0.94 (t, 3H), 1.4 (m, 2H), 1.6 (m, 3H), 2.7 (t, 2H), 3.5 (bs, 1H), 6.1 (bs, 1H), 7.32 (d, 2H), 7.63 (d, 2H), 7.8 (s, 2H), 8.1 (s, 1H), 10.1 (bs, 1H)

Example 25-7
(2R)-N-hydroxy-3-methyl-2-[(2-phenoxybenzthiazol-6-sulfonyl)amino]butyric Amide (120 mg, 72%)

Example 25-8
(2R)-N-hydroxy-3-methyl-2-[(2-(4-methoxyphenyl) methylthiobenzthiazol-6-sulfonyl)amino]butyric Amide $^1$H NMR (300 MHz, CDCl$_3$): δ 0.85 (m, 6H), 1.9 (m, 1H), 3.55 (m, 1H), 3.78 (s, 3H), 4.58 (s, 2H), 6.4 (d, 1H), 6.87 (d, 2H), 7.36 (m, 3H), 7.89 (m, 2H), 8.29 (s, 1H), 10.3 (bs, 1H)

Example 25-9
(2R)-N-hydroxy-3-methyl-2-[(2-benzylthiobenzthiazol-6-sulfonyl)amino]butyric Amide $^1$H NMR (300 MHz, CDCl$_3$): δ 0.82 (m, 6H), 1.22 (m, 1H), 3.5 (m, 1H), 4.6 (s, 2H), 6.2 (m, 1H), 7.3 (m, 3H), 7.4 (m, 2H), 7.86 (m, 2H), 8.26 (s, 1H), 10.2 (s, 1H)

Example 25-10
(2R)-N-hydroxy-3-methyl-2-[(2-(4-chlorophenyl) methylthiobenzthiazol-6-sulfonyl) amino]butyric Amide $^1$H NMR (300 MHz, DMSO-d$_6$): δ 0.72 (m, 6H), 1.7(m, 1H), 3.2 (m, 1H), 4.7 (s, 2H), 7.38 (d, 2H), 7.53 (d, 2H), 7.82 (d, 1H), 7.95 (d, 1H), 7.98 (d, 1H), 8.7 (s, 1H), 10.5 (s, 1H)

Example 25-11
(2R)-N-hydroxy-3-methyl-2-[(2-(3-phenylethylthio) benzthiazol-6-sulfonyl)amino]butyric Amide $^1$H NMR (300 MHz, CDCl$_3$): δ 0.75 (d, 3H), 0.81(d, 3H), 1.8 (m, 1H), 3.13 (t, 2H), 3.58 (m, 1H), 3.62 (t, 3H), 5.8 (bs, 1H), 7.28 (m, 5H), 7.9 (m, 2H), 8.3 (s, 1H)

Example 25-12
(2R)N-hydroxy-3-methyl-2-[(2-cyclopentylthiobenzthiazol-6-sulfonyl)amino]butyric Amide $^1$H NMR (300 MHz, DMSO-d$_6$): δ 0.72 (m, 6H), 1.68 (m, 9H), 3.3 (m, 1H), 4.1 (m, 1H), 7.77 (d, 1H), 7.92 (d, 1H), 8.0 (m, 1H), 8.4 (s, 1H), 8.74 (s, 1H), 10.5 (s, 1H)

EXAMPLE 26

Preparation of (2R)-3-methyl-2-[(ethylthio-6-benzthiazolsulfonyl)benzylamino]butanoic Acid Methylester and Other Derivatives (2R)-3-methyl-2-[(2-ethylthiobenzthiazol-6-sulfonyl) amino]butanoic acid methylester (0.16 g, 0.376 mmol) prepared in a similar manner as in Example 14 was dissolved in DMF (1 mL). $K_2CO_3$ (150 mg, 3 equi.) and benzylbromide (0.056 mL, 1.3 equi.) were added at RT. After stirring the reaction solution for 1 hour at RT, ethylacetate (5 mL) and $H_2O$ were added to afford the phase separation, when starting material was exhausted. The separated organic phase was washed with $H_2O$ for several times, dried over $MgSO_4$ and distilled under reduced pressure to prepare the titled compound, (2R)-3-methyl-2-[(ethylthio-6-benzthiazolsulfonyl)benzylamino]butanoic acid methylester (180 mg, 100%).

$^1$H NMR (300 MHz, $CDCl_3$): δ 0.82 (d, 6H), 1.51 (t, 3H), 2.0 (m, 1H), 3.36 (s, 3H), 3.38 (q, 2H), 4.23 (d, 1H), 4.6 (dd, 2H), 7.21 (m, 3H), 7.33 (m, 2H), 7.76 (d, 1H), 7.83 (d, 1H), 8.0 (s, 1H)

Example 26-1
(2R)-3-methyl-2-[(methylthio-6-benzthiazolsulfonyl) benzylamino]butanoic Acid Methylester $^1$H NMR (300 MHz, $CDCl_3$): δ 0.83 (d, 6H), 2.0 (m, 1H), 2.82 (s, 3H), 3.35 (s, 3H), 4.23 (d, 1H), 4.6 (dd, 2H), 7.2 (m, 3H), 7.25(m, 2H), 7.8 (dd, 2H), 8.0 (s, 1H)

Example 26-2
(2R)-3-methyl-2-[(n-propylthio-6-benzthiazolsulfonyl) benzylamino]butanoic Acid Methylester $^1$H NMR (300 MHz, $CDCl_3$): δ 0.82 (d, 6H), 1.1 (t, 3H), 1.87 (q, 2H), 2.0 (m, 1H), 3.36 (m, 5H), 4.23 (d, 1H), 4.6 (dd, 2H), 7.22 (m, 3H), 7.33 (m, 2H), 7.78 (dd, 2H), 8.0 (s, 1H)

Example 26-3
(2R)-3-methyl-2-[(n-propylthio-6-benzoxazolsulfonyl) benzylamino]butanoic Acid Methylester $^1$H NMR (300 MHz, $CDCl_3$): δ 0.82 (m, 6H), 1.1. (t, 3H), 1.89 (q, 2H), 1.9 (m, 1H), 3.32 (t, 2H), 3.38 (s, 3H), 4.23 (d, 1H), 4.6 (dd, 2H), 7.22 (m, 3H), 7.34 (m, 2H), 7.64 (dd, 2H), 7.78 (s, 1H)

Example 26-4
(2R)-3-methyl-2-[(n-butylthio-6-benzthiazolsulfonyl) benzylamino]butanoic Acid Methylester $^1$H NMR (300 MHz, $CDCl_3$): δ 0.82 (d, 6H), 0.98 (t, 3H), 1.5 (m, 2H), 1.82(m, 2H), 2.0(m, 1H), 3.35 (s, 3H), 3.38 (q, 2H), 4.23 (d, 1H), 4.6 (dd, 2H), 7.22 (m, 3H), 7.33 (m, 2H), 7.8 (dd, 2H), 8.0 (s, 1H)

Example 26-5
(2R)-3-methyl-2-[(n-pentylthio-6-benzthiazolsulfonyl) benzylamino]butanoic Acid Methylester $^1$H NMR (300 MHz, $CDCl_3$): δ 0.82 (d, 6H), 0.93 (t, 3H), 1.45 (m, 4H), 1.85 (p, 2H), 1.95 (m, 1H), 3.35 (s, 3H), 3.37 (t, 2H), 4.22 (d, 1H), 4.65 (dd, 2H), 7.22 (m, 3H), 7.33 (m, 2H), 7.79 (dd, 2H), 8.0 (s, 1H)

Example 26-6
(2R)-3-methyl-2-[(n-hexylthio-6-benzthiazolsulfonyl) benzylamino]butanoic Acid Methylester $^1$H NMR (300 MHz, $CDCl_3$): δ 0.82 (d, 6H), 0.9 (t, 3H), 1.33 (m, 4H), 1.5 (m, 2H), 1.8 (p, 2H), 2.0 (m, 1H), 3.35 (s, 3H), 3.37 (t, 2H), 4.2 (d, 1H), 4.6 (dd, 2H), 7.2 (m, 3H), 7.3 (m, 2H), 7.8 (dd, 2H), 8.0 (s, 1H)

Example 26-7
(2R)-3-methyl-2-[(n-octylthio-6-benzthiazolsulfonyl) benzylamino]butanoic Acid Methylester $^1$H NMR (300 MHz, $CDCl_3$): δ 0.82 (d, 6H), 0.88 (t, 3H), 1.3(m, 8H), 1.5 (m, 2H), 1.85 (p, 2H), 2.0 (m, 1H), 3.35 (s, 3H), 3.37 (t, 2H), 4.23 (d, 1H), 4.6 (dd, 2H), 7.22 (m, 3H), 7.33 (m, 2H), 7.8 (dd, 2H), 8.0 (s, 1H)

Example 26-8
(2R)-3-methyl-2-[(n-dodecylthio-6-benzthiazolsulfonyl) benzylamino]butanoic Acid Methylester $^1$H NMR (300 MHz, $CDCl_3$): δ 0.82 (d, 6H), 0.85 (t, 3H), 1.26 (m, 14H), 1.5 (m, 2H), 1.8 (p, 2H), 2.0 (m, 1H), 3.35 (s, 3H), 3.37 (t, 2H), 4.23 (d, 1H), 4.6 (dd, 2H), 7.22 (m, 3H), 7.33 (m, 2H), 7.8 (dd, 2H), 8.0 (s, 1H)

EXAMPLE 27

Preparation of (2R)-3-methyl-2-[(ethylthio-6-benzthiazolsulfonyl)benzylamino]butanoic Acid and Other Derivatives (2R)-3-methyl-2-[(ethylthio-6-benzthiazolsulfonyl) benzylamino]butanoic acid methylester (180 mg, 0.376 mmol) prepared in Example 26 was dissolved in $THF/H_2O$ (2 mL/2 mL), and LiOH (0.08 g, 5 equi.) was added. After reflux for 6 days, the reaction solution was distilled under reduced pressure and treated with 1N HCl, and ethylacetate (10 mL) was added to extract the product. The separated organic phase containing product was washed with NaCl solution, dried over $MgSO_4$ and distilled under reduced pressure. The remaining material was purified on silica gel chromatography using ethylacetate/n-hexane (1/1) and ethylacetate/dichloromethane/acetate (1/1/trace amount) as solvent and dried under vacuum to prepare the titled compound, (2R)-3-methyl-2-[(ethylthio-6-benzthiazolsulfonyl)benzylamino]butanoic acid (0.1 g, 57%).

$^1$H NMR (300 MHz, $CDCl_3$): δ 0.82 (d, 3H), 0.90 (d, 3H), 1.5 (t, 3H), 2.0 (m, 1H), 3.33 (q, 2H), 4.24 (d, 1H), 4.63 (dd, 2H), 7.21 (m, 3H), 7.35 (m, 2H), 7.79 (m, 2H), 8.0 (s, 1H)

Example 27-1
(2R)-3-methyl-2-[(hydroxy-6-benzthiazolsulfonyl) benzylamino]butanoic Acid $^1$H NMR (300 MHz, $CDCl_3$): δ 0.83 (d, 3H), 0.91 (d, 3H), 2.0 (m, 1H), 4.1 (d, 1H), 4.6 (m, 2H), 7.2 (m, 3H), 7.3 (m, 2H), 7.6 (m, 2H), 7.8 (s, 1H)

Example 27-2
(2R)-3-methyl-2-[(n-propylthio-6-benzthiazolsulfonyl) benzylamino]butanoic Acid $^1$H NMR (300 MHz, $CDCl_3$): δ 0.8 (d, 3H), 0.9 (d, 3H), 1.1 (t, 3H), 1.8 (q, 2H), 2.0 (m, 1H), 3.3 (t, 2H), 4.25 (d, 1H), 4.6 (dd, 2H), 7.2 (m, 3H), 7.37 (m, 2H), 7.75 (s, 2H), 8.0 (s, 1H)

Example 27-3
(2R)-3-methyl-2-[(n-butylthio-6-benzthiazolsulfonyl) benzylamino]butanoic Acid $^1$H NMR (300 MHz, $CDCl_3$): δ 0.82 (d, 3H), 0.9 (d, 3H), 0.97 (t, 3H), 1.65 (m, 2H), 1.8 (p, 2H), 2.0 (m, 1H), 3.31 (t, 2H), 4.23 (d, 1H), 4.6 (dd, 2H), 7.22 (m, 3H), 7.35 (m, 2H), 7.78 (s, 2H), 8.0 (s, 1H)

Example 27-4
(2R)-3-methyl-2-[(n-pentylthio-6-benzthiazolsulfonyl) benzylamino]butanoic Acid $^1$H NMR (300 MHz, $CDCl_3$): δ 0.82 (d, 3H), 0.92 (m, 6H), 1.4 (m, 4H), 1.8 (p, 2H), 2.0 (m, 1H), 3.32 (t, 2H), 4.23 (d, 1H), 4.6 (dd, 2H), 7.2 (m, 3H), 7.35 (m, 2H), 7.8 (s, 2H), 8.0 (s, 1H)

Example 27-5
(2R)-3-methyl-2-[(n-hexylthio-6-benzthiazolsulfonyl) benzylamino]butanoic Acid $^1$H NMR (300 MHz, CDCl$_3$): δ 0.82 (d, 3H), 0.9 (m, 6H), 1.33 (m, 4H), 1.45 (m, 2H), 1.79 (p, 2H), 2.0 (m, 1H), 3.3 (t, 2H), 4.23 (d, 1H), 4.6 (dd, 2H), 7.2 (m, 3H), 7.35 (m, 2H), 7.78 (s, 2H), 8.06 (s, 1H)

Example 27-6
(2R)-3-methyl-2-[(n-octylthio-6-benzthiazolsulfonyl) benzylamino]butanoic Acid $^1$H NMR (300 MHz, CDCl$_3$): δ 0.82 (d, 3H), 0.9 (m, 6H), 1.3 (m, 8H), 1.5 (m, 2H), 1.8 (p, 2H), 2.0 (m, 1H), 3.3 (t, 2H), 4.23 (d, 1H), 4.6 (dd, 2H), 7.2 (m, 3H), 7.37 (m, 2H), 7.78 (s, 2H), 8.06 (s, 1H)

Example 27-7
(2R)-3-methyl-2-[(n-dodecylthio-6-benzthiazolsulfonyl) benzylamino]butanoic acid $^1$H NMR (300 MHz, CDCl$_3$): δ 0.82 (d, 3H), 0.87 (m, 6H), 1.26 (m, 14H), 1.5 (m, 2H), 1.8 (p, 2H), 2.0 (m, 1H), 3.3 (t, 2H), 4.2 (d, 1H), 4.6 (dd, 2H), 7.2 (m, 3H), 7.38 (m, 2H), 7.8 (s, 2H), 8.05 (s, 1H)

EXAMPLE 28
Preparation of (2R)-N-hydroxy-3-methyl-2-[(ethylthio-6-benzthiazolsulfonyl) benzylamino]butyric Amide and Other Derivatives (2R)-3-methyl-2-[(ethylthio-6-benzthiazolsulfonyl) benzylamino]butanoic acid (50 mg, 0.108 mmol) prepared in Example 27 was dissolved in dichloromethane (2 mL) and cooled down to 0° C. Oxalylchloride (0.094 mL, 10 equi.) and DMF of catalytic amount were added. Then, the reaction solution was reacted for 3 hours at RT. And then, the solution was distilled and dried under reduced pressure to prepare (2R)-3-methyl-2-[(2-ethylthio-6-benzthiazolsulfonyl) benzylamino]butanoic chloride. The compound was dissolved in in THF (1 mL) to give acid chloride THE solution. Hydroxyamine hydrochloride salt (0.08 g, 10 equi.) and NaHCO$_3$ (0.11 g, 12 equi.) were dissolved in THF/H$_2$O (2 mL/2 mL) and cooled down to 0° C. Acid chloride THF solution was slowly added to hydroxyamine solution while maintaining the temperature of 0° C. After 1 hour, the solvent was removed from the reaction solution. The product was extracted with ethylacetate (5 mL), washed with H$_2$O and 0.1N HCl, dried over MgSO$_4$, distilled under reduced pressure and vacuum-dried to prepare the titled compound, (2R)-N-hydroxy-3-methyl-2-[(ethylthio-6-benzthiazolsulfonyl)benzylamino]butyric amide (52 mg, 100%).

$^1$H NMR (300 MHz, DMSO-d$_6$): δ 0.57 (d, 3H), 0.84 (d, 3H), 1.5 (t, 3H), 2.2 (m, 1H), 3.36 (q, 2H), 3.8 (d, 1H), 4.55 (dd, 2H), 7.2 (m, 3H), 7.3 (m, 2H), 7.6 (s, 1H), 7.75 (s, 1H), 7.9 (s, 2H), 9.4 (s, 1H)

Example 28-1
(2R)-N-hydroxy-3-methyl-2-[(n-propylthio-6-benzthiazolsulfonyl)benzylamino]butyric Amide $^1$H NMR (300 MHz, CDCl$_3$): δ 0.59 (d, 3H), 0.82 (d, 2H), 1.1 (t, 3H), 1.87 (m, 2H), 2.2 (m, 1H), 3.33 (t, 2H), 3.88 (d, 2H), 4.61 (dd, 2H), 7.18 (m, 3H), 7.31 (m, 2H), 7.62 (d, 1H), 7.7 (d, 1H), 7.85 (s, 1H), 9.5 (s, 1H)

Example 28-2
(2R)-N-hydroxy-3-methyl-2-[(n-butylthio-6-benzthiazolsulfonyl)benzylamino]butyric Amide $^1$H NMR (300 MHz, DMSO-d$_6$): δ 0.72 (t, 6H), 0.91 (t, 3H), 1.4 (m, 2H), 1.7 (m, 2H), 1.9 (m, 1H), 3.37 (t, 2H), 3.8 (d, 1H), 4.7 (s, 2H), 7.15 (m, 3H), 7.35 (m, 2H), 7.8 (dd, 2H), 8.2 (s, 1H), 8.9 (s, 1H), 10.7 (s, 1H)

Example 28-3
(2R)-N-hydroxy-3-methyl-2-[(n-pentylthio-6-benzthiazolsulfonyl)benzylamino]butyric Amide $^1$H NMR (300 MHz, CDCl$_3$): δ 0.75 (d, 3H), 0.86 (d, 3H), 0.93 (t, 3H), 1.43 (m, 4H), 1.8 (p, 2H), 2.1 (m, 1H), 3.36 (t, 2H), 3.95 (d, 1H), 4.7 (s, 2H), 7.15 (m, 3H), 7.31 (m, 2H), 7.74 (dd, 2H), 7.88 (s, 1H), 10.5 (s, 1H)

Example 28-4
(2R)-N-hydroxy-3-methyl-2-[(n-hexylthio-6-benzthiazolsulfonyl)benzylamino]butyric Amide $^1$H NMR (300 MHz, CDCl$_3$): δ 0.49 (d, 3H), 0.85 (d, 3H), 0.91 (t, 3H), 1.35 (m, 4H), 1.57 (m, 2H), 1.8 (p, 2H), 2.2 (m, 1H), 3.37 (t, 2H), 3.75 (d, 1H), 4.58 (dd, 2H), 7.24 (m, 3H), 7.33 (m, 2H), 7.67 (d, 1H), 7.83 (d, 1H), 7.9 (s, 1H), 9.0 (s, 1H)

Example 28-5
(2R)-N-hydroxy-3-methyl-2-[(n-octylthio-6-benzthiazolsulfonyl)benzylamino]butyric Amide $^1$H NMR (300 MHz, CDCl$_3$): δ 0.54 (d, 3H), 0.88 (m, 6H), 1.32 (m, 8H), 1.5 (m, 2H), 1.8 (p, 2H), 2.25 (m, 1H), 3.36 (t, 2H), 3.85 (d, 1H), 3.6 (dd, 1H), 7.2 (m, 3H), 7.31 (m, 2H), 7.65 (d, 1H), 7.85 (d, 1H), 7.92 (s, 1H), 9.2 (s, 1H)

Example 28-6
(2R)-N-hydroxy-3-methyl-2-[(n-dodecylthio-6-benzthiazolsulfonyl)benzylamino]butyric Amide $^1$H NMR (300 MHz, CDCl$_3$): δ 0.52 (d, 3H), 0.85 (m, 6H), 1.26 (m, 16H), 1.5 (m, 2H), 1.8 (p, 2H), 0.25 (m, 1H), 3.35 (t, 2H), 3.8 (d, 1H), 4.6 (dd, 2H), 7.22 (m, 3H), 7.31 (m, 2H), 7.65 (d, 1H), 7.85 (d, 1H), 7.9 (s, 1H), 9.2 (s, 1H)

EXAMPLE 29
Preparation of (2R)-2-[(2-n-pentylthiobenzthiazol-6-sulfonyl)amino]propionic Acid and Other Derivatives (D)-alaninemethylester hydrochloride (0.2 g, 1.43 mmol) was dispersed in dichloromethane (3 mL) and cooled down to 0° C. 2-n-pentylthio-6-benzthiazolsulfonyl chloride (0.39 g, 1.0 equi.) prepared in the above Example was dissolved in dichloromethane (2 mL). Triethylamine (0.6 mL, 3 equi.) and the dichloromethane solution prepared above were added while maintaining the temperature of 0° C. When starting material was disappeared after 5 hours, the organic phase was washed with 1N HCl solution, dried over MgSO$_4$, distilled under reduced pressure and vacuum-dried to prepare the titled compound, (2R)-2-[(2-n-pentylthiobenzthiazol-6-sulfonyl) amino]propionic acid methylester (0.4 g, 69%).

$^1$H NMR (300 MHz, CDCl$_3$): δ 0.94 (t, 3H), 1.41 (d, 3H), 1.42 (m, 4H), 1.86 (p, 2H), 3.39 (t, 2H), 3.52 (s, 3H), 4.05 (p, 1H), 5.31 (d, 1H), 7.91 (dd, 2H), 8.28 (s, 1H)

(2R)-2-[(2-n-pentylthiobenzthiazol-6-sulfonyl) amino] propionic acid methylester (0.22 g, 0.547 mmol) was dissolved in THF/H$_2$O (2 mL/2 mL) and treated with LiOH (0.115 g, 5 equi.). After reflux for 6 hours, the reaction solution was distilled under reduced pressure to remove the solvent and treated with 1N HCl solution, and ethylacetate (10 mL) was added to extract product. Then, the separated organic phase was washed with NaCl solution, dried over MgSO$_4$, distilled under reduced pressure and vacuum-dried to prepare the titled compound, (2R)-2-[(2-n-pentylthiobenzthiazol-6-sulfonyl)amino]propionic acid (0.2 mg, 94%).

$^1$H NMR (300 MHz, CDCl$_3$): δ 0.92 (t, 3H), 1.45 (m, 7H), 1.83 (p, 2H), 3.35 (t, 3H), 4.04 (p, 1H), 5.45 (d, 1H), 7.86 (m, 2H), 8.28 (s, 1H)

The following titled compounds were prepared by employing other sulfonyl chloride instead of 2-n-pentylthio-6-benzthiazolsulfonyl chloride used in the above process.

Example 29-1
(2R)-2-[(2-n-hexylthiobenzthiazol-6-sulfonyl)amino] propionic Acid $^1$H NMR (300 MHz, CDCl$_3$): δ 0.90 (t, 3H), 1.34 (m, 4H), 1.45 (m, 5H), 1.83 (p, 2H), 3.32 (m, 2H), 4.05 (p, 1H), 5.4 (d, 1H), 7.86 (m, 2H), 8.29 (s, 1H)

Example 29-2
(2R)-2-[(2-(cyclohexylmethylthio) benzthiazol-6-sulfonyl)amino]Propionic Acid $^1$H NMR (300 MHz, CDCl$_3$): δ 1.10 (m, 2H), 1.24 (m, 3H), 1.45 (d, 3H), 1.80 (m, 4H), 1.95 (d, 2H), 3.26 (d, 2H), 4.06 (m, 1H), 5.45 (d, 1H), 7.88 (m, 2H), 8.30 (s, 1H)

EXAMPLE 30

The following titled compounds were prepared in a similar manner as in Example 29, except for employing such amino acids as (D)-phenylalanine, (D)-methionine, (D)-leucine, (D)-aspartic acid, (D)-glutamic acid, (D)-tryptophan methylester and (±)-2-amino-2-methyl-3-phenylpropionic acid ethylester.

Example 30-1
(2R)-2-[(2-n-pentylthiobenzthiazol-6-sulfonyl)amino]-3-phenylpropionic Acid $^1$H NMR (300 MHz, CDCl$_3$): δ 0.93 (t, 3H), 1.40 (m, 4H), 1.83 (p, 2H), 3.12 (dd, 1H), 3.12 (dd, 1H), 3.33 (t, 2H), 4.2 (m, 1H), 5.2 (d, 1H), 7.08 (m, 2H), 7.18 (m, 3H), 7.75 (dd, 2H), 8.07 (s, 1H)

Example 30-2

(2R)-2-[(2-n-hexylthiobenzthiazol-6-sulfonyl)amino]-3-phenylpropionic Acid $^1$H NMR (300 MHz, CDCl$_3$): δ 0.90 (t, 3H), 1.33 (m, 4H), 1.55 (m, 2H), 1.82 (p, 2H), 2.99 (dd, 1H), 3.15 (dd, 1H), 3.34 (t, 2H), 4.25 (m, 1H), 5.2 (d, 1H), 7.09 (m, 2H), 7.2 (m, 3H), 7.71 (d, 1H), 7.79 (d, 1H), 8.07 (s, 1H)

Example 30-3
(2R)-2-[(2-(cyclohexylmethylthio) benzthiazol-6-sulfonyl)amino]-3-phenylpropionic Acid $^1$H NMR (300 MHz, CDCl$_3$): δ 1.09 (m, 2H), 1.25 (m, 3H), 1.71 (m, 4H), 1.93 (d, 2H), 3.0 (dd, 1H), 3.11 (dd, 1H), 3.27 (d, 2H), 4.15 (m, 1H), 5.6 (d, 1H), 7.15 (m, 5H), 7.74 (dd, 2H), 8.08 (s, 1H)

Example 30-4
(2R)-4-methylthio-2-[(2-n-pentylthiobenzthiazol-6-sulfonyl)amino]butyric Acid $^1$H NMR (300 MHz, CDCl$_3$): δ 0.93 (t, 3H), 1.40 (m, 4H), 1.83 (m, 2H), 1.9 (m, 1H), 2.06 (s, 3H), 2.1 (m, 1H), 2.57 (m, 2H), 3.32 (t, 2H), 4.2 (m, 1H), 5.5 (d, 1H), 7.87 (m, 2H), 8.30 (s, 1H)

Example 30-5
(2R)-4-methylthio-2-[(2-n-hexylthiobenzthiazol-6-sulfonyl)amino]butyric Acid $^1$H NMR (300 MHz, CDCl$_3$): δ 0.92 (t, 3H), 1.33 (m, 4H), 1.5 (m, 2H), 1.83 (m, 2H), 1.9 (m, 1H), 2.06 (s, 3H), 2.1 (m, 1H), 2.55 (m, 2H), 3.32 (t, 2H), 4.15 (m, 1H), 5.47 (d, 1H), 7.88 (m, 2H), 8.30 (s, 1H)

Example 30-6
(2R)-4-methylthio-2-[(2-(cyclohexylmethylthio) benzthiazol-6-sulfonyl)amino]butyric Acid $^1$H NMR (300 MHz, CDCl$_3$): δ 1.15 (m, 2H), 1.24 (m, 3H), 1.74 (m, 4H), 1.90 (m, 3H), 2.06 (s, 1H), 2.1 (m, 1H), 2.57 (m, 2H), 3.22 (d, 2H), 4.2 (m, 1H), 5.54 (d, 1H), 7.87 (m, 2H), 8.3 (s, 1H)

Example 30-7
(2R)-4-methyl-2-[(2-n-pentylthiobenzthiazol-6-sulfonyl)amino]valeric Acid $^1$H NMR (300 MHz, CDCl$_3$): δ 0.93 (m, 9H), 1.4 (m, 4H), 1.5 (m, 2H), 1.83 (p, 3H), 3.33 (t, 2H), 4.0 (m, 1H), 5.18 (d, 1H), 7.87 (m, 2H), 8.28 (s, 1H)

Example 30-8
(2R)-4-methyl-2-[(2-n-hexylthiobenzthiazol-6-sulfonyl)amino]valeric Acid $^1$H NMR (300 MHz, CDCl$_3$): δ 0.91 (m, 9H), 1.34 (m, 4H), 1.54 (m, 4H), 1.84 (m, 3H), 3.33 (t, 2H), 4.0 (m, 1H), 5.1 (m, 1H), 7.86 (m, 2H), 8.28 (s, 1H)

Example 30-9
(2R)-2-[(2-pentylthiobenzthiazol-6-sulfonyl)amino] succinic Acid $^1$H NMR (300 MHz, CDCl$_3$): δ 1.90 (t, 3H), 1.26 (m, 2H), 1.45 (m, 2H), 1.79 (p, 2H), 2.9 (dd, 1H), 3.1 (dd, 1H), 3.37 (t, 2H), 4.15 (m, 1H), 6.1 (d, 1H), 7.9 (s, 2H), 8.3 (s, 1H)

Example 30-10
(2R)-2-[(2-hexylthiobenzthiazol-6-sulfonyl)amino]succinic Acid $^1$H NMR (300 MHz, CDCl$_3$): δ 0.9 (t, 3H), 1.3 (m, 4H), 1.5 (m, 2H), 1.75 (p, 2H), 2.9 (dd, 1H), 3.1 (dd, 1H), 3.3 (t, 2H), 4.2 (m, 1H), 6.7 (d, 1H), 7.83 (s, 2H), 8.23 (s, 1H)

Example 30-11
(2R)-2-[(2-pentylthiobenzthiazol-6-sulfonyl)amino]glutaric Acid $^1$H NMR (300 MHz, CDCl$_3$): δ 0.93 (t, 3H), 1.41 (m, 4H), 1.84 (m, 3H), 2.15 (m, 1H), 2.45 (m, 2H), 3.36 (t, 2H), 3.95 (m, 1H), 5.9 (d, 1H), 7.87 (s, 1H), 8.28 (s, 1H)

Example 30-12
(2R)-2-[(2-hexylthiobenzthiazol-6-sulfonyl)amino]glutaric Acid $^1$H NMR (300 MHz, DMSO-d$_6$): δ 0.86 (t, 3H), 1.30 (m, 4H), 1.45 (m, 2H), 1.75 (m, 2H), 1.9 (m, 1H), 2.1 (m, 1H), 2.4 (m, 2H), 3.32 (t, 2H), 3.85 (m, 1H), 5.8 (m, 1H), 7.83 (s, 2H), 8.24 (s, 1H)

Example 30-13
(2R)-2-[(2-pentylthiobenzthiazol-6-sulfonyl)amino]-3-(1H-indole-3-yl) Propionic Acid $^1$H NMR (300 MHz, DMSO-d$_6$): δ 0.86 (t, 3H), 1.36 (m, 4H), 1.76 (m, 2H), 2.8 (dd, 1H), 3.1 (dd, 1H), 3.37 (t, 2H), 3.87 (m, 1H), 6.78 (t, 1H), 6.90 (t, 1H), 7.04 (s, 1H), 7.14 (m, 2H), 7.53 (d, 1H), 7.69 (d, 1H), 8.13 (s, 1H), 8.3 (d, 1H), 10.74 (s, 1H)

Example 30-14
(±)-2-[(2-n-hexylthiobenzthiazol-6-sulfonyl)amino]-2-methyl-3-phenylpropionic Acid $^1$H NMR (300 MHz, CDCl$_3$): δ 0.9 (t, 3H), 1.34 (m, 4H), 1.48 (m, 5H), 1.8 (p, 2H), 3.1 (d, 1H), 3.3 (d, 1H), 3.35 (t, 1H), 5.45 (s, 1H), 7.27 (m, 5H), 7.85 (s, 2H), 8.0 (s, 1H), 8.2 (s, 1H)

EXAMPLE 31

Preparation of (2R)-N-hydroxy-2-[(2-n-pentylthiobenzthiazol-6-sulfonyl)amino]Propionamide (2R)-2-[(2-n-pentylthiobenzthiazol-6-sulfonyl) amino] propionic acid (190 mg, 0.49 mmol) prepared in Example 29 was dissolved in dichloromethane (2 mL) and cooled down to 0° C. Oxalylchloride (0.17 mL, 4 equi.) and DMF of catalytic amount were added and the reaction solution was refluxed for 3 hours at RT. Then, the solution was distilled under reduced pressure to remove the solvent and dried under reduced pressure to give (2R)-2-[(2-n-pentylthiobenzthiazol-6-sulfonyl)amino]propionic chloride. And then, the compound was dissolved in THF (2 mL) to obtain acid chloride THF solution. Hydroxyamine hydrochloride salt (0.34 g, 10 equi.) and $NaHCO_3$ (0.49 g, 12 equi.) was dissolved in $THF/H_2O$ (1 mL/1 mL) and cooled down to 0° C. Acid chloride THF solution was slowly added to hydroxyamine solution at 0° C., and the solvent was removed after 1 hour. Then, the product was extracted with ethylacetate (5 mL), washed with $H_2O$ and 0.1N HCl, dried over $MgSO_4$, distilled and vacuum-dried to prepare the titled compound, (2R)-N-hydroxy-2-[(2-n-pentylthiobenzthiazol-6-sulfonyl)amino] propion amide (190 mg, 97%).

$^1H$ NMR (300 MHz, $CDCl_3$): δ 0.93 (s, 3H), 1.23 (m, 3H), 1.43 (m, 4H), 1.86 (p, 2H), 3.37 (t, 2H), 3.85 (m, 1H), 6.6 (m, 1H), 7.88 (s, 1H), 8.29 (s, 1H), 10.2 (s, 1H)

EXAMPLE 32

Preparation of Various Hydroxamic Acids

The following hydroxamic acids were produced in a similar manner as in Example 31 by employing various acid derivatives prepared in Examples 29 and 30.

Example 32-1

(2R)-N-hydroxy-2-[(2-n-hexylthio benzthiazol-6-sulfonyl)amino]propionamide $^1H$ NMR (300 MHz, $CDCl_3$): δ 0.89 (t, 3H), 1.23 (m, 3H), 1.33 (m, 4H), 1.49 (m, 2H), 1.85 (m, 2H), 3.37 (t, 2H), 4.9 (m, 1H), 6.55 (d, 1H), 7.88 (m, 2H), 8.3 (s, 1H), 10.2 (s, 1H)

Example 32-2

(2R)-N-hydroxy-2-[(2-(cyclohexylmethylthio)benzthiazol-6-sulfonyl)amino]propionamide $^1H$ NMR (300 MHz, $CDCl_3$): δ 1.06~1.28 (m, 8H), 1.76 (m, 4H), 2.0 (m, 2H), 3.24 (d, 2H), 3.9 (m, 1H), 6.2 (s, 1H), 7.87 (s, 2H), 8.3 (s, 1H)

Example 32-3

(2R)-N-hydroxy-2-[(2-n-pentylthiobenzthiazol-6-sulfonyl)amino]-3-phenylpropion Amide $^1H$ NMR (300 MHz, $CDCl_3$): δ 0.93 (t, 3H), 1.5 (m, 4H), 1.8 (p, 2H), 2.8(dd, 1H), 3.05(dd, 1H), 3.37 (t. 2H), 4.0 (m, 1H), 6.3 (m, 1H), 7.0 (m 5H), 7.6 (d, 1H), 7.7 (d, 1H), 7.93 (s, 1H), 10.1 (s, 1H)

Example 32-4

(2R)-N-hydroxy-2-[(2-n-hexylthiobenzthiazol-6-sulfonyl)amino]-3-phenylpropionamide $^1H$ NMR (300 MHz, $CDCl_3$): δ 0.88 (t, 3H), 1.33 (m, 4H), 1.47 (m, 2H), 1.81 (m, 2H), 2.8 (m, 1H), 3.0 (m, 1H), 3.34 (t, 2H), 4.0 (m, 1H), 6.5 (m, 1H), 6.98 (s, 5H), 7.66 (dd, 2H), 7.89 (s, 1H), 10.2 (s, 1H)

Example 32-5

(2R)-N-hydroxy-2-[(2-(cyclohexylmethylthio)benzthiazol-6-sulfonyl)amino]-3-phenylpropionamide $^1H$ NMR (300 MHz, $CDCl_3$): δ 1.2 (m, 5H), 1.7 (m, 4H), 1.93 (m, 2H), 2.85 (m, 1H), 3.1 (m, 1H), 3.3 (d, 2H), 3.95 (m, 1H), 5.55 (s, 1H), 6.86 (m, 2H), 7.0 (m, 3H), 7.55 (d, 1H), 7.75 (d, 1H), 7.9 (s, 1H)

Example 32-6

(2R)-N-hydroxy-4-methylthio-2-[(2-n-pentylthiobenzthiazol-6-sulfonyl)amino]butyric Amide $^1H$ NMR (300 MHz, $CDCl_3$): δ 0.92 (t, 3H), 1.41 (m, 4H), 1.81 (m, 2H), 1.9~2.1 (m, 7H), 3.35 (m, 2H), 3.9 (s, 1H), 6.7 (m, 1H), 7.86 (s, 2H), 8.3 (s, 1H), 10.1 (s, 1H)

Example 32-7

(2R)-N-hydroxy-4-methylthio-2-[(2-n-hexylthiobenzthiazol-6-sulfonyl)amino]butyric Amide $^1H$ NMR (300 MHz, $CDCl_3$): δ 0.9 (t, 3H), 1.3 (m, 4H), 1.5 (m, 2H), 1.83 (m, 3H), 2.0 (s, 3H), 2.1 (m, 1H), 2.35 (m, 2H), 3.37 (t, 2H), 4.0 (d, 1H), 6.6 (d, 1H), 7.89 (m, 2H), 8.3 (s, 1H), 10.2 (s, 1H)

Example 32-8

(2R)-N-hydroxy-4-methylthio-2-[(2-(cyclohexylmethylthio)benzthiazol-6-sulfonyl)amino]butyric Amide $^1H$ NMR (300 MHz, $CDCl_3$): δ 1.1 (m, 2H), 1.23 (m, 3H), 1.73 (m, 9H), 1.91 (m, 4H), 2.32 (d, 2H), 4.0 (d, 1H), 6.2 (d, 1H), 7.9 (M, 2H), 8.31 (s, 1H), 9.4 (s, 1H)

Example 32-9

(2R)-N-hydroxy-4-methyl-2-[(2-n-pentylthiobenzthiazol-6-sulfonyl)amino]valeric Amide $^1H$ NMR (300 MHz, $CDCl_3$): δ 0.64 (m, 3H), 0.87 (m, 6H), 1.4~1.8 (m, 9H), 3.31 (t, 2H), 3.8 (d, 1H), 6.4 (d, 1H), 7.8 (s, 2H), 8.3 (s, 1H), 1 10.4 (s, 1H)

Example 32-10

(2R)-N-hydroxy-4-methyl-2-[(2-n-hexyl-thiobenzthiazol-6-sulfonyl)amino]valeric Amide $^1H$ NMR (300 MHz, $CDCl_3$): δ 0.64~0.87 (m, 9H), 1.3~1.78 (m, 9H), 3.32 (m, 2H), 3.8 (m, 1H), 6.3 (m, 1H), 7.83 (s, 2H), 8.23 (s, 1H), 10.2 (s, 1H)

EXAMPLE 33

Preparation of (2R)-2-[(2-n-pentylthiobenzthiazol-6-sulfonyl)benzylamino] propionic Acid and Other Derivatives (2R)-2-[(2-n-pentylthiobenzthiazol-6-sulfonyl) amino] propionic acid methylester (131 mg, 0.325 mmol) prepared in Example 29 was dissolved in DMF (1 ml). $K_2CO_3$ (135 mg, 3 equi.) and benzylbromide (0.05 mL, 1.3 equi.) were added at RT, and stirred for 1 hour at RT. When starting material was exhausted, ethylacetate (5 mL) and $H_2O$ were added to afford the phase separation. The separated organic phase was washed with $H_2O$ for several times, dried over $MgSO_4$, distilled under reduced pressure to prepare the titled compound, (2R)-2-[(2-n-pentylthiobenzthiazol-6-sulfonyl) benzylamino] propionic acid methylester (160 mg, 100%).

$^1H$ NMR (300 MHz, $CDCl_3$): δ 0.93 (t, 3H), 1.31 (d, 3H), 1.45 (m, 4H), 1.85 (p, 2H), 3.38 (t, 2H), 3.42 (s, 3H), 4.58 (dd, 2H), 4.68 (q, 1H), 7.26 (m, 5H), 7.84 (dd, 2H), 8.18 (s, 1H)

The above prepared (2R)-2-[(2-n-pentylthiobenzthiazol-6-sulfonyl)benzylamino] propionic acid methylester (146 mg, 0.296 mmol) was dissolved in $THF/H_2O$ (1 mL/1 mL). LiOH(62 mg, 5 equi.) was added and the reaction solution was refluxed for 5 to 7 days until starting material was disappeared. After the reaction was completed, the reaction solution was distilled under reduced pressure and treated with 1N HCl solution, and ethylacetate (5 mL) was added. The separated organic phase containing extracted product was washed with NaCl solution, dried over MgSO$_4$ and distilled under reduced pressure. The remaining material after distillation was purified on silica gel chromatography using ethylacetate/n-hexane (1/1) and ethylacetate/dichloromethane/acetate (1/1/trace amount) as solvent. The purified compound was dried under vacuum to prepare the titled compound, (2R)-2-[(2-n-pentylthiobenzthiazol-6-sulfonyl)benzylamino] propionic acid (142 mg, 100%).

$^1$H NMR (300 MHz, CDCl$_3$): δ 0.94 (t, 3H), 1.38~1.45 (m, 7H), 1.83 (p, 2H), 3.35 (t, 2H), 4.42 (d, 1H), 4.65 (m, 2H), 7.28 (m, 5H), 7.87 (m, 2H), 8.20 (s, 1H)

The following titled compounds were prepared by hydrolysis of n-benzyl intermediates, which were obtained by introducing benzyl group to nitrogen of amide of various methylesters as starting material prepared analogously as in Example 29, in a similar manner as above under LiOH/THF/H$_2$O condition.

Example 33-1

(2R)-2-[(2-(cyclohexylmethylthio) benzthiazol-6-sulfonyl) benzylamino]propionic Acid $^1$H NMR (300 MHz, CDCl$_3$): δ 1.0~1.28 (m, 5H), 1.37 (d, 3H), 1.78 (m, 4H), 1.9 (d, 2H), 3.23 (d, 2H), 4.35 (d, 1H), 4.65 (m, 2H), 7,26 (m, 5H), 7.85 (m, 2H), 8.17 (s, 1H)

Example 33-2

(2R)-2-[(2-n-pentylthiobenzthiazol-6-sulfonyl)benzylamino]-3-phenylpropionic Acid $^1$H NMR (300 MHz, CDCl$_3$): δ 0.92 (t, 3H), 1.38 (m, 4H), 1.83 (p, 2H), 2.3 (m, 2H), 2.9 (m, 1H), 3.33 (t, 2H), 4.5 (dd, 2H), 5.9 (s, 1H), 7.0 (m, 10H), 7.73 (dd, 2H), 8.0 (s, 1H)

Example 33-3

(2R)-2-[(2-(cyclohexylmethylthio) benzthiazol-6-sulfonyl)benzylamino]-3-phenylpropionic Acid $^1$H NMR (300 MHz, CDCl$_3$): δ 1.24 (m, 5H), 1.74 (m, 4H), 1.9 (m, 2H), 2.4 (m, 2H), 2.9 (m, 1H), 3.2 (d, 2H), 4.4 (dd, 2H), 4.8 (m, 1H), 7.0 (m, 2H), 7.2 (m, 8H), 7.7 (dd, 2H), 8.0 (s, 1H)

Example 33-4

(2R)-4-methylthio-2-[(2-n-pentylthiobenzthiazol-6-sulfonyl)benzylamino]butyric Acid $^1$H NMR (300 MHz, CDCl$_3$): δ 0.93 (t, 1H), 1.4 (m, 4H), 1.7 (m, 2H), 1.8 (s, 1H), 2.1 (m, 2H), 2.3 (m, 2H), 3.3 (t, 2H), 4.3 (d, 1H), 4.7 (m, 2H), 7.3 (m, 5H), 7.86 (s, 1H), 8.3 (s, 1H)

Example 33-5

(2R)-4-methyl-2-[(2-n-pentylthiobenzthiazol-6-sulfonyl)benzylamino]valeric Acid $^1$H NMR (300 MHz, CDCl$_3$): δ 0.55 (d, 3H), 0.85 (d, 3H), 0.93 (t, 3H), 1.47 (m, 7H), 1.83 (p, 2H), 3.34 (t, 2H), 4.4 (d, 1H), 4.6 (m, 1H), 4.72 (d, 1H), 7.26 (m, 3H), 7.37(m, 2H), 7.84 (m, 2H), 8.18 (s, 1H)

EXAMPLE 34

Preparation of (2R)-N-hydroxy-2-[(2-n-pentylthiobenzthiazol-6-sulfonyl)benzylamino]propion Amide and Other Derivatives (2R)-2-[(2-n-pentylthiobenzthiazol-6-sulfonyl)benzylamino]propionic acid (157 mg, 0.328 mmol) prepared in Example 33 was dissolved in dichloromethane (2 mL) and cooled down to 0° C. Oxalylchloride (0.114 mL, 10 equi.) and DMF of catalytic amount were added and the reaction solution was refluxed for 3 hours at RT. After reaction, the solution was distilled under reduced pressure to remove the solvent and dried under reduced pressure to give (2R)-3-methyl-2-[(2-methylthiobenzthiazol-6-sulfonyl)amino] butanoic chloride. The compound was then dissolved in THF (1 mL) to obtain acid chloride THF solution. Hydroxyamine hydrochloride salt (0.23 g, 10 equi.) and NaHCO$_3$ (0.33 g, 12 equi.) were dissolved in THF/H$_2$O (3 mL/3 mL) and cooled down to 0° C. to give a hydroxyamine solution. The above acid chloride THF solution was slowly added to the hydroxyamine solution at 0° C. After 1 hour, the solvent was removed from the reaction solution. Then, the product was extracted with ethylacetate 10 mL), washed with H$_2$O and 0.1N HCl, dried over MgSO$_4$, distilled under reduced pressure and vacuum-dried to prepare the titled compound, (2R)-N-hydroxy-2-[(2-n-pentylthiobenzthiazol-6-sulfonyl)benzylamino]propionamide (163 mg, 100%).

$^1$H NMR (300 MHz, DMSO-d$_6$): δ 0.93 (t, 3H), 1.23 (m, 3H), 1.3 (m, 4H), 1.85 (p, 2H), 3.38 (t, 2H), 4.3 (d, 1H), 4.5 (m, 1H), 4.7 (d, 1H), 7.28 (m, 5H), 7.8 (dd, 2H), 8.2 (s, 1H), 9.0 (s, 1H)

Using various N-benzylsulfonyl acid derivatives as a starting material obtained in Example 33, the following titled compounds were prepared by applying the above method under the condition of oxalylchloride/hydroxyamine hydrochloride/NaHCO$_3$/THF/H$_2$O.

Example 34-1

(2R)-N-hydroxy-2-[(2-(cyclohexylmethylthio)benzthiazol-6-sulfonyl)benzylamino]propionamide $^1$H NMR (300 MHz, CDCl$_3$): δ 1.26 (m, 8H), 1.74 (m, 4H), 1.9 (m, 2H), 3.28 (d, 2H), 4.2 (d, 1H), 4.4 (m, 1H), 4.6 (d, 1H), 7.3 (m, 5H), 7.8 (dd, 2H), 8.1 (s, 1H), 9.0 (s, 1H)

Example 34-2

(2R)-N-hydroxy-2-[(2-n-pentylthiobenzthiazol-6-sulfonyl)benzylamino]-3-phenylpropionamide $^1$H NMR (300 MHz, CDCl$_3$): δ 0.94 (t, 3H), 1.3 (m, 4H), 1.86 (p, 2H), 2.7 (dd, 1H), 3.2 (dd, 1H), 3.4 (t, 2H), 4.6 (dd, 2H), 6.8 (m, 2H), 7.0 (m, 3H), 7.3 (m, 5H), 7.7 (d, 1H), 7.8 (d, 1H), 7.9 (s, 1H), 9.0 (s, 1H)

Example 34-3

(2R)-N-hydroxy-4-methylthio-2-[(2-n-pentylthiobenzthiazol-6-sulfonyl) benzylamino]butyric Amide $^1$H NMR (300 MHz, CDCl$_3$): δ 0.9 (t, 3H), 1.3 (m, 7H), 1.8 (m, 3H), 2.2 (m, 2H), 3.38 (t, 2H), 4.3 (d, 1H), 4.6 (m, 2H), 7.29 (m, 5H), 7.8 (dd, 2H), 8.1 (s, 1H), 9.1 (s, 1H)

Example 34-4

(2R)-N-hydroxy-4-methyl-2-[(2-n-pentylthiobenzthiazol-6-sulfonyl)benzylamino]valeric Amide $^1$H NMR (300 MHz, CDCl$_3$): δ 0.64 (dd, 6H), 0.93 (t, 3H), 1.26 (m, 1H), 1.4 (m, 5H), 1.8 (m, 3H), 3.83 (t, 2H), 4.4 (m, 2H), 4.65 (d, 1H), 7.28 (m, 5H), 7.7 (d, 1H), 7.82 (d, 1H), 8.0 (s, 1H), 9.1 (s, 1H)

EXAMPLE 35

Preparation of (±)-diethyl-1-[(2-(n-butylthio)benzthiazol-6-sulfonyl) amino]-2-phenylethyl-phosphonate and Other Derivatives Diethyl 1-amino-2-phenylethylphosphonate (0.14 g, 0.5442 mmol) prepared by the conventionally known method was dispersed in dichloromethane (3 mL) and cooled down to 0° C., and triethylamine (0.08 mL, 1.1 equi.) was added. 2-n-butylthio-6-benzthiazolsulfonyl chloride (0.184 g, 1.05 equi.) prepared in the above Example was dissolved in dichloromethane (2 mL) to give a dichloromethane solution. The dichloromethane solution was added while maintaining the temperature of 0° C. After 5 hours, when starting material was exhausted, the organic phase was washed with 1N HCl, dried over MgSO$_4$, distilled under reduced pressure and dried under vacuum to prepare the titled compound, diethyl-1-[(2-(n-butylthio)benzthiazol-6-sulfonyl)amino]-2-phenylethylphosphonate (0.206 g, 70%).

Using 2-n-hexylthio-6-benzthiazolsulfonyl chloride (0.25 g, 1.05 equi.) and 2-(cyclohexylmethylthio)-6-benzthiazolsulfonyl chloride (0.177 g, 1.05 equi.) prepared by the same method as above, the following titled compounds were prepared.

Example 35-1
(±)-diethyl-1-[(2-(n-hexylthio) benzthiazol-6-sulfonyl)amino]-2-phenylethylphosphonate $^1$H NMR (300 MHz, CDCl$_3$): δ 0.89 (t, 3H), 1.35 (t, 10H), 1.50 (m, 2H), 1.83 (p, 2H), 2.75 (m, 1H), 3.1 (m, 1H), 3.36 (t, 2H), 4.07 (m, 4H), 4.25 (m, 1H), 6.85 (d, 1H), 6.95 (m, 5H), 7.65 (dd, 2H), 7.86 (s, 1H)

Example 35-2
(±)-diethyl-1-[(2-(n-butylthio) benzthiazol-6-sulfonyl)amino]-2-phenylethylphosphonate $^1$H NMR (300 MHz, CDCl$_3$): δ 0.99 (t, 3H), 1.3 (q, 6H), 1.53 (h, 2H), 1.83 (p, 2H), 2.82 (m, 1H), 3.1 (m, 1H), 3.39 (d, 2H), 4.10 (m, 4H), 4.25 (m, 1H), 6.65 (d, 1H), 6.97 (m, 5H), 7.68 (dd, 2H), 7.87 (s, 1H)

Example 35-3
(±)-diethyl-1-[(2-(cyclohexylmethylthio) benzthiazol-6-sulfonyl)amino]-2-phenylethylphosphonate $^1$H NMR (300 MHz, CDCl$_3$): δ 1.1 (m, 2H), 1.26 (m, 9H), 1.71 (m, 4H), 1.93 (d, 2H), 2.83 (m, 1H), 3.11 (m, 1H), 3.28 (d, 2H), 4.09 (m, 4H), 4.27 (m, 1H), 6.78 (d, 1H), 6.93 (m, 5H), 7.67 (dd, 2H), 7.86 (s, 1H)

EXAMPLE 36
Preparation of (±)-1-[(2-(n-butylthio) benzthiazol-6-sulfonyl)amino]-2-phenylethyl Phosphonic Acid and Other Derivatives (±)-Diethyl-1-[(2-(n-butylthio)benzthiazol-6-sulfonyl)amino]-2-phenylethylphosphonate (0.1 g, 0.184 mmol) prepared in Example 35 was dissolved in anhydrous dichloromethane (3 mL) under the anhydrous nitrogen. Then, bromotrimethylsilane (0.24 mL, 10 equi.) was added at 0° C. in the presence of nitrogen and the reaction temperature was slowly elevated to the room temperature, followed by stirring for 12 hours. When starting material was exhausted, the solvent was dried under reduced pressure and crystallized with cold water to give a solid compound which was then filtered. The compound thus obtained was washed with H$_2$O several times and dried under reduced pressure to prepare the titled compound, (±)-1-[(2-(n-butylthio)benzthiazol-6-sulfonyl)amino]-2-phenylethylphosphonic acid (80 mg, 90%).

$^1$H NMR (300 MHz, CDCl$_3$): δ 1.0 (t, 3H), 1.53 (m, 2H), 1.85 (m, 2H), 2.7 (m, 1H), 3.0 (m, 1H), 3.4 (t, 2H), 4.0 (m, 1H), 6.9 (m, 5H), 7.67 (m, 2H), 7.8 (s, 1H)

The following titled compounds were prepared in a similar manner as above, except for employing (±)-diethyl-1-[(2-(n-hexylthio)benzthiazol-6-sulfonyl)amino]-2-phenylethylphosphonate (0.05 g, 0.087 mmol) and (±)-diethyl-1-[(2-(cyclohexylmethylthio)benzthiazol-6-sulfonyl)amino]-2-phenylethylphosphonate (0.05 g, 0.0858 mmol) prepared in Example 35 as starting materials.

Example 36-1
(±)-1-[(2-(n-hexylthio)benzthiazol-6-sulfonyl)amino]-2-phenylethylphosphonic Acid $^1$H NMR (300 MHz, CDCl$_3$): δ 0.91 (t, 3H), 1.35 (m, 4H), 1.50 (m, 2H), 1.89 (p, 2H), 2.7 (m, 1H), 3.0 (m, 1H), 3.4 (t, 2H), 4.0 (m, 1H), 6.88 (m, 5H), 7.5 (d, 1H), 7.68 (d, 1H), 7.7 (s, 1H)

Example 36-2
(±)-1-[(2-(cyclohexylmethylthio) benzthiazol-6-sulfonyl)amino]-2-phenylethylphosphonic Acid $^1$H NMR (300 MHz, CDCl$_3$): δ 1.17 (m, 2H), 1.28 (m, 3H), 1.79 (m, 4H), 1.95 (d, 2H), 2.7 (m, 1H), 3.1 (m, 1H), 3.33 (d, 2H), 4.09 (m, 1H), 6.86 (m, 5H), 7.6 (d, 1H), 7.73 (d, 1H), 7.83 (s, 1H)

EXAMPLE 37
(2R)-N-[2-(n-pentylthiobenzthiazol-6-sulfonyl)]-2-methylcarboxylpyrrolidine (D)-proline methylester hydrochloride (0.29 g, 1.75 mmol) was dispersed in dichloromethane (3 mL) and cooled down to 0° C., and triethylamine (0.73 mL, 3 equi.) was added. 2-n-pentylthio-6-benzthiazolsulfonyl chloride (0.35 g, 1.0 equi.) prepared in Example 2 was dissolved in dichloromethane (2 mL) to give a dichloromethane solution. Then, the dichloromethane solution was added while maintaining the temperature of 0° C. After starting material was exhausted (about 5 hours), the organic phase was washed with 1N HCl, dried over MgSO$_4$, distilled under reduced pressure and dried under vacuum to prepare (2R)-N-[2-(n-pentylthiobenzthiazol-6-sulfonyl)]-2-methylcarboxylpyrrolidine (0.17 g, 23%).

$^1$H NMR (300 MHz, CDCl$_3$): δ 0.93 (t, 3H), 1.45 (m, 4H), 1.84 (m, 3H), 2.0 (m, 3H), 3.37 (t, 3H), 3.5 (m, 1H), 3.7 (s, 3H), 4.4 (t, 1H), 7.9 (m, 2H), 8.3 (s, 1H)

EXAMPLE 38
(2R)-N-[2-(n-pentylthiobenzthiazol-6-sulfonyl)]-2-pyrrolidylcarboxylic Acid (2R)-N-[2-(n-pentylthiobenzthiazol-6-sulfonyl)]-2-methylcarboxylpyrrolidine (0.17 g, 0.4 mmol) prepared in Example 37 was dissolved in THF/H$_2$O (2 mL/2 mL), and added LiOH (0.083 g, 5 equi.). After reacting with reflux for 6 hours, the solution was distilled under reduced pressure and treated with 1N HCl, and extracted with ethylacetate (10 mL). The extracted product was washed with NaCl solution, dried over MgSO$_4$, distilled under reduced pressure and dried under vacuum to prepare the titled compound, (2R)-N-[2-(n-pentylthiobenzthiazol-6-sulfonyl)]-2-pyrrolidylcarboxylic acid (160 mg, 97%).

$^1$H NMR (300 MHz, CDCl$_3$): δ 0.93 (t, 3H), 1.45 (m, 4H), 1.82 (m, 3H), 1.83 (m, 2H), 2.15 (m, 1H), 3.3 (m, 1H), 3.38 (t, 2H), 3.6 (m, 1H), 4.35 (m, 1H), 7.95 (dd, 2H), 8.3 (s, 1H)

EXAMPLE 39
(2R)-N-[2-(n-hexylthiobenzthiazol-6-sulfonyl)]-2-pyrrolidylcarboxylic Acid $^1$H NMR (300 MHz, CDCl$_3$): δ 0.90 (t, 3H), 1.33 (m, 4H), 1.49 (m, 2H), 1.8 (m, 3H), 1.87 (m, 2H), 2.2 (m, 1H), 3.3 (q, 1H), 3.38 (t, 2H), 3.6 (m, 1H), 4.3 (m, 1H), 7.95 (dd, 2H), 8.3 (s, 1H)

EXAMPLE 40
Preparation of (3R)-1,2,3,4-tetrahydro-N-[2-(n-pentylthiobenzthiazol-6-sulfonyl)]-3-isoquinolinecarboxylic Acid (3R)-1,2,3,4-Tetrahydro-3-isoquinolinecarboxylic acid (0.2 g, 1 mmol) prepared by the conventionally known method was dispersed in dichloromethane (3 mL) and cooled down to 0° C., and triethylamine (0.4 mL, 3 equi.) was added. 2-n-pentylthio-6-benzthiazolsulfonyl chloride (0.26 g, 1.0 equi.) prepared in Example 2 was dissolved in dichloromethane (2 mL) to give a dichloromethane solution. Then, the dichloromethane solution was added while maintaining the temperature of 0° C. After starting material was exhausted(about 5 hours), the solution was treated with 1N HCl solution and then, the organic phase was washed with NaCl solution, dried over $MgSO_4$, distilled under reduced pressure and dried under vacuum to prepare the titled compound, (3R)-1,2,3,4-tetrahydro-N-[2-(n-pentylthiobenzthiazol-6-sulfonyl)]-3-isoquinolinecarboxylic acid (0.3 g, 63%).

$^1$H NMR (300 MHz, $CDCl_3$): δ 0.92 (t, 3H), 1.4 (m, 4H), 1.83 (m, 2H), 3.18 (d, 2H), 3.35 (t, 2H), 4.6 (dd, 2H), 5.0 (t, 1H), 7.15 (m, 4H), 7.83 (m, 2H), 8.25 (s, 1H)

EXAMPLE 41

Preparation of (±)-1,2,3,4-tetrahydro-N-[2-(n-pentylthiobenzthiazol-6-sulfonyl)]-3-methyl-3-isoquinolinecarboxylic Acid Methylester (±)-1,2,3,4-tetrahydro-3-methyl-3-isoquinolinecarboxylic acid methylester (0.16 g, 0.78 mmol) prepared by the conventionally known method was dispersed in dichloromethane(3 mL) and cooled down to 0° C., and triethylamine (0.73 mL, 3 equi.) was added. 2-n-pentylthio-6-benzthiazolsulfonyl chloride (0.35 g, 1.0 equi.) prepared in Example 2 was dissolved in dichloromethane (2 mL) to give a dichloromethane solution. Then, the dichloromethane solution was added while maintaining the temperature of 0° C. After starting material was exhausted(about 5 hours), the organic phase was washed with 1N HCl, dried over $MgSO_4$, distilled under reduced pressure and dried under vacuum, to prepare the titled compound, (±)-1,2,3,4-tetrahydro-N-[2-(n-pentylthiobenzthiazol-6-sulfonyl)]-3-methyl-3-isoquinolinecarboxylic acid methylester (0.17 g, 23%).

$^1$H NMR (300 MHz, $CDCl_3$): δ 0.93 (t, 3H), 1.45 (m, 4H), 1.58 (s, 3H), 1.84 (m, 2H), 2.88 (d, 1H), 3.25 (d, 1H), 3.36 (t, 2H), 3.80 (s, 3H), 4.4 (dd, 2H), 7.2 (m, 4H), 7.89 (m, 2H), 8.3 (s, 1H)

EXAMPLE 42

Preparation of (±)-1,2,3,4-tetrahydro-N-[2-(n-pentylthiobenzthiazol-6-sulfonyl)]-3-methyl-3-isoquinolinecarboxylic Acid (±)-1,2,3,4-tetrahydro-N-[2-(n-pentylthiobenzthiazol-6-sulfonyl)]-3-methyl-3-isoquinolinecarboxylic acid methylester (0.17 g, 0.337 mmol) was dissolved in $THF/H_2O$ (2 mL/2 mL), and LiOH (0.071 g, 5 equi.) was added. After the reaction soluton was reacted with reflux for 6 hours, the solvent was distilled under reduced pressure and treated with 1N HCl, and extracted with ethylacetate (10 mL). The material thus extracted was washed with NaCl solution, dried over $MgSO_4$, distilled under reduced pressure and dried under vacuum to prepare the titled compound, (±)-1,2,3,4-tetrahydro-N-[2-(n-pentylthiobenzthiazol-6-sulfonyl)]-3-methyl-3-isoquinolinecarboxylic acid (100 mg, 60%).

$^1$H NMR (300 MHz, $CDCl_3$): δ 0.93 (t, 3H), 1.45 (m, 4H), 1.64 (s, 3H), 1.84 (m, 2H), 2.96 (d, 1H), 3.31 (d, 1H), 3.37 (t, 2H), 4.4 (dd, 2H), 7.0 (d, 4H), 7.20 (m, 3H), 7.91 (m, 2H), 8.33 (s, 1H)

EXAMPLE 43

Preparation of (3S)-4-(2-cyclohexylmethylthiobenzthiazol-6-sulfonyl)-2,2-dimethyl-tetrahydro-2H-1,4-thiazine-3-carboxylic Acid (3S)-2,2-dimethyl-tetrahydro-2H-1,4-thiazine-3-carboxylic acid (0.93 g, 5.31 mmol) prepared by the conventionlly known method (see: WO 9720824) was dissolved in DMF (7 mL). DBU (0.95 mL, 1.2 equi.) was added and the reaction solution was stirred for 1 hour at RT. Then, dimethylthexylsilyl chloride (1.15 mL, 1.1 equi.) was added and the reaction solution was stirred for 5 hours at RT. The reaction solution was added to ice water/hexane:t-butylmethylether (7 mL:7 mL) solution, followed by weak shaking. The organic phase was dried over $MgSO_4$, distilled under reduced pressure and dried under a vacuum to give (3S)-dimethylthexylsilyl-2,2-dimethyl-tetrahydro-2H-1,4-thiazine-3-carboxylate (1.5 g) in a liquid form. It was dissolved in EDC (15 mL) and cooled down to 0° C. N-methylmorpholine (0.62 mL, 1.2 equi.) was added, followed by stirring for 30 minutes. 2-cyclohexylmethylthio-6-benzthiazolsulfonyl chloride (1.7 g, 1 equi.) was dissolved in EDC (5 mL) and then, the solution was added to the reaction mixture. After starting material was exhausted, the product was extracted with ethylacetate (10 mL). The material thus extracted was washed with NaCl solution, dried over $MgSO_4$, distilled under reduced pressure and dried under vacuum to give (3S)-4-(2-cyclohexylmethylthiobenzthiazol-6-sulfonyl)-2,2-dimethyl-tetrahydro-2H-1,4-thiazine-3-carboxylic acid dimethylthexylsilyl ester. The compound was dissolved in methanol (20 mL) and the solution was refluxed for 6 hours. Then, the solvent was distilled under reduced pressure and the pH was adjusted to 2 with 2N HCl, and extracted with ethylacetate (10 mL). The material thus extracted was dried over $MgSO_4$, distilled under reduced pressure and dried under vacuum. A remaining mixture was purified on silica gel chromatography by elution with ethylacetate/hexane (1/5) to give the titled compound, (3S)-4-(2-cyclohexylmethylthiobenzthiazol-6-sulfonyl)-2,2-dimethyltetrahydro-2H-1,4-thiazine-3-carboxylic acid (1.08 g, 40%).

$^1$H NMR (300 MHz, $CDCl_3$): δ 1.1 (m, 2H), 1.25 (m, 4H), 1.37 (s, 3H), 1.64 (s, 3H), 1.74 (m, 3H), 1.9 (m, 2H), 2.5 (d, 1H), 3.15 (m, 1H), 3.21 (d, H), 3.7(m, 1H), 4.12 (m, 1H), 4.47 (s, 1H), 7.74(d, 1H), 7.84 (d, 1H), 8.2 (s, 1H)

EXAMPLE 44

Preparation of (3S)-4-[2-(n-butylthiobenzthiazol-6-sulfonyl)]-2,2-dimethyl-tetrahydro-2H-1,4-thiazine-3-carboxylic Acid $^1$H NMR (300 MHz, $CDCl_3$): δ 0.98 (t, 3H), 1.38 (s, 3H), 1.53 (m, 2H), 1.65 (s, 3H), 1.82 (m, 2H), 2.5 (d, 1H), 3.15 (m, 1H), 3.33 (t, 2H), 3.7 (m, 1H), 4.1 (d, 1H), 4.5 (s, 1H), 7.75 (d, 1H), 7.87 (d, 1H), 8.2 (s, 1H)

EXAMPLE 45

Preparation of (3S)-4-[2-(n-hexylthiobenzthiazol-6-sulfonyl)]-2,2-dimethyl-tetrahydro-2H-1,4-thiazine-3-carboxylic Acid $^1$H NMR (300 MHz, $CDCl_3$): δ 0.92 (t, 3H), 1.38 (m, 4H), 1.39 (s, 3H), 1.50 (m, 2H), 1.67 (s, 3H), 1.82 (m, 2H), 2.5 (d, 1H), 3.2 (m, 1H), 3.31 (t, 2H), 3.75 (m, 1H), 4.16 (d, 1H), 4.5 (s, 1H), 7.77 (d, 1H), 7.89 (d, 1H), 8.22 (s, 1H)

EXAMPLE 46
Preparation of (2R)-N-hydroxy-1-[2-(n-pentylthiobenzthiazol-6-sulfonyl)]-2-pyrrolidylcarboxylamide (2R)-N-[2-(n-pentylthiobenzthiazol-6-sulfonyl)]-2-pyrrolidylcarboxylic acid (0.16 g, 0.39 mmol) prepared in Example 38 was dissolved in dichloromethane (2 mL) and cooled down to 0° C. Oxalylchloride (0.1 mL, 3 equi.) and DMF of catalytic amount was added, and reacted for 3 hours at RT. Then, the reaction solution was distilled under reduced pressure to remove solvent and dried under reduced pressure. And then, the remaining material was dissolved in THF (1 mL). Hydroxylamine hydrochloride (0.27 g, 10 equi.) and $NaHCO_3$ (0.39 g, 12 equi.) were dissolved in $THF/H_2O$ (2 mL/2 mL) and cooled down to 0° C. The acid chloride/THF solution thus obtained was slowly added to hydroxylamine solution while maintaining the temperature of 0° C. After 1 hour, the solvent was removed from the reaction solution. The product was extracted with ethylacetate (5 mL) and then, washed with $H_2O$ and 0.1N HCl, dried over $MgSO_4$, distilled under reduced pressure and dried under vacuum to prepare the titled compound, (2R)-N-hydroxy-1-[2-(n-pentylthiobenzthiazol-6-sulfonyl)]-2-pyrrolidylcarboxylic acid (0.14 g, 84%).

$^1$H NMR (300 MHz, $CDCl_3$): δ 0.93 (t, 3H), 1.43 (m, 4H), 1.6 (m, 2H), 1.8 (m, 4H), 2.2 (m, 1H), 3.2 (m, 1H), 3.37 (t, 2H), 3.6 (m, 1H), 4.2 (d, 1H), 7.94 (dd, 2H), 8.3 (s, 1H), 9.5 (s, 1H)

EXAMPLE 47
Preparation of (2R)-N-hydroxy-1-[2-(n-hexylthiobenzthiazol-6-sulfonyl)]-2-pyrrolidyl-carboxylamide $^1$H NMR (300 MHz, $CDCl_3$): δ 0.9 (t, 3H), 1.33 (m, 4H), 1.45 (m, 2H), 1.6 (m, 2H), 1.8 (m, 3H), 2.2 (m, 1H), 3.2 (m, 1H), 3.38 (t, 2H), 3.6 (m, 1H), 4.2 (d, 1H), 7.94 (dd, 2H), 8.3 (s, 1H), 9.5 (s, 1H)

EXAMPLE 48
Preparation of (3R)-N-hydroxy-1,2,3,4-tetrahydro-2-[2-(n-pentylthiobenzthiazol-6-sulfonyl)]-3-isoquinolinecarboxylamide (3R)-1,2,3,4-tetrahydro-2-[2-(n-pentylthiobenzthiazol-6-sulfonyl)]-3-isoquinolinecarboxylic acid (0.2 g, 0.42 mmol) prepared in Example 40 was dissolved in dichloromethane (2 mL) and cooled down to 0° C. Oxalylchloride (0.11 mL, 3 equi.) and DMF of catalytic amount was added, and reacted for 3 hours at RT. Then, the reaction solution was distilled under reduced pressure to remove solvent and dried under reduced pressure. And then, the remaining material was dissolved in THF (1 mL). Hydroxylamine hydrochloride (0.29 g, 10 equi.) and $NaHCO_3$ (0.42 g, 12 equi.) were dissolved in $THF/H_2O$ (2 mL/2 mL) and cooled down to 0° C. The acid chloride/THF solution thus obtained was slowly added to hydroxylamine solution while maintaining the temperature of 0° C. After 1 hour, the solvent was removed from the reaction solution. The product was extracted with ethylacetate (5 mL) and then, washed with $H_2O$ and 0.1N HCl, dried over $MgSO_4$, distilled under reduced pressure and dried under vacuum to prepare (3R)-N-hydroxy-1,2,3,4-tetrahydro-2-[2-(n-pentylthio-benzthiazol-6-sulfonyl)]-3-isoquinolinecarboxylamide (0.2 g, 99%).

$^1$H NMR (300 MHz, $CDCl_3$): δ 0.92 (t, 3H), 1.41 (m, 4H), 1.8 (m, 2H), 2.65 (m, 1H), 3.15 (m, 1H), 3.35 (t, 2H), 4.5 (m, 3H), 7.09 (m, 4H), 7.8 (dd, 2H), 8.16 (s, 1H), 9.4 (s, 1H)

EXAMPLE 49
Preparation of (±)-N-hydroxy-1,2,3,4-tetrahydro-2-[2-(n-pentylthiobenzthiazol-6-sulfonyl)]-3-methyl-3-isoquinolinecarboxylamide $^1$H NMR (300 MHz, $CDCl_3$): δ 0.93 (t, 3H), 1.40 (m, 4H), 1.65 (s, 3H), 1.83 (m, 2H), 2.85 (d, 1H), 3.24 (d, 1H), 3.38 (t, 2H), 4.42 (d, 1H), 4.55 (d, 1H), 7.24 (m, 4H), 7.87 (m, 2H), 8.28 (s, 1H), 8.8 (s, 1H)

EXAMPLE 50
Preparation of (3S)-N-hydroxy-4-(2-cyclohexylmethylthiobenzthiazol-6-sulfonyl)-2,2-dimethyl-tetrahydro-2H-1,4-thiazine-3-carboxylamide (3S)-4-(2-cyclohexylmethylthiobenzthiazol-6-sulfonyl)-2,2-dimethyl-tetrahydro-2H-1,4-thiazine-3-carboxylic acid (0.84 g, 1.68 mmol) prepared in Example 43 was dissolved in dichloromethane (2 mL) and cooled down to 0° C. Oxalylchloride (0.44 mL, 3 equi.) and DMF of catalytic amount were added, and reacted for 3 hours at RT. Then, the reaction solution was distilled under reduced pressure to remove solvent and dried under reduced pressure. And then, the remaining material was dissolved in THF (1 mL). Hydroxylamine hydrochloride (1.17 g, 10 equi.) and $NaHCO_3$ (1.69 g, 12 equi.) were dissolved in $THF/H_2O$ (2 mL/2 mL) and cooled down to 0° C. The acid chloride/THF solution thus obtained was slowly added to hydroxylamine solution while maintaining the temperature of 0° C. After 1 hour, the solvent was removed from the reaction solution. The product was extracted with ethylacetate (5 mL) and then, washed with $H_2O$ and 0.1N HCl, dried over $MgSO_4$, distilled under reduced pressure and dried under vacuum to prepare the titled compound, (3R)-N-hydroxy-1,2,3,4-tetrahydro-2-[2-(n-pentylthiobenzthiaz ol-6-sulfonyl)]-3-isoquinolinecarboxylamide (0.87 g, 100%).

$^1$H NMR (300 MHz, $CDCl_3$): δ 1.22 (m, 5H), 1.28 (s, 3H), 1.58 (s, 3H), 1.74 (m, 4H), 1.9 (d, 2H), 2.45 (d, 1H), 3.1 (m, 1H), 3.28 (d, 2H), 3.8 (m, 2H), 4.3 (s, 1H), 7.77 (d, 1H), 7.87 (d, 1H), 8.21 (s,1H), 10.8 (s, 1H)

EXAMPLE 51
Preparation of (3S)-N-hydroxy-4-[2-(n-butylthiobenzthiazol-6-sulfonyl)]-2,2-dimethyl-tetrahydro-2H-1,4-thiazine-3-carboxylamide $^1$H NMR (300 MHz, $CDCl_3$): δ 0.98 (t, 3H), 1.29 (s, 3H), 1.53 (m, 4H), 1.60 (s, 3H), 1.83 (m, 2H), 2.5 (d, 1H), 3.2 (m, 2H), 3.38 (t, 2H), 4.1 (d, 1H), 4.6 (s, 1H), 7.1 (s, 1H), 7.8 (d, 1H), 7.9 (d, 1H), 8.23 (s, 1H), 9.7 (s, 1H)

EXAMPLE 52
Preparation of (3S)-N-hydroxy-4-[2-(n-hexylthiobenzthiazol-6-sulfonyl)]-2,2-dimethyl-tetrahydro-2H-1,4-thiazine-3-carboxylamide $^1$H NMR (300 MHz, $CDCl_3$): δ 0.93 (t, 3H), 1.26 (s, 3H), 1.35 (m, 4H), 1.5 (m, 2H), 1.58 (s, 3H), 1.9 (m, 2H), 2.5 (d, 1H), 3.1 (m, 1H), 3.37 (m, 3H), 3.78 (t, 2H), 4.0 (d, 1H), 4.53 (s, 1H), 7.8 (dd, 2H), 8.2 (s, 1H), 9.9 (s, 1H)

EXAMPLE 53
(±)-methyl 2-amino-3-(4-biphenyl)propionate Hydrochloride

Sodium (0.624 g, 27 mmol) was completely dissolved in absolute ethanol and diethyl acetamidomalonate (5.9 g, 27 mmol) was added in a solid form, followed by stirring for 1 hour. And then, 4-phenylbenzyl chloride (5 g, 24.67 mmol) and KI (0.1 equi.) was added and a reaction was accomplished at a temperature of 50–60° C. for 12 hours. After starting material, 4-phenylbenzyl chloride was completely exhausted, the solvent was distilled under reduced pressure and extracted with water/ethylacetate (100 mL/100 mL). The separated organic phase was washed with 1N HCl, dried over anhydrous MgSO$_4$, dried under reduced pressure to prepare acetamido (4-biphenylmethyl)malonic acid diethylester (9.1 g, 96%).

$^1$H NMR (300 MHz, DMSO-d$_6$): δ 1.19 (t, 6H), 1.98 (s, 3H), 3.48 (s, 2H), 4.19 (q, 4H), 7.07 (d, 2H), 7.48 (d, 2H), 7.65 (m, 5H), 8.17 (s, 1H)

5N-NaOH (5 mL, 1.05 equi.) was added to acetamido (4-biphenylmethyl)malonic acid diethylester (9.1 g, 23.73 mmol) and hydrolyzed at RT. Then, the solvent was removed from the reaction solution and impurities was removed by adding ethylacetate (20 mL). And then, the solid product was obtained by filtering, washed several times with water and dried under reduced pressure to give 2-ethylcarboxy-2-acetylamino-3-(4-biphenyl) propionic acid (6.7 g, 79%).

$^1$H NMR (300 MHz, DMSO-d$_6$): δ 1.17 (t, 3H), 1.95 (s, 3H), 3.48 (dd, 2H), 4.13 (q, 2H), 7.07 (d, 2H), 7.34 (t, 1H), 7.45 (t, 2H), 7.61 (dd, 4H), 7.91 (s, 1H)

2-Ethylcarboxy-2-acetylamino-3-(4-biphenyl) propionic acid (6.7 g, 18 mmol) was dissolved in toluene (40 mL) and reacted with reflux for 6 hours to complete decarboxylation. After starting material was exhausted, the solvent was removed from the reaction soluton. The remaining material was redissolved in ethylacetate (50 mL), washed with a saturated NaHCO$_3$ (20 mL), dried over anhydrous MgSO$_4$, dried under reduced pressure to parepare 2-acetylamino-3-(4-biphenyl)propionic acidethylester (4.4 g, 79%).

$^1$H NMR (300 MHz, CDCl$_3$): δ 1.28 (t, 3H), 2.0 (s, 3H), 3.16 (d, 2H), 4.21 (q, 2H), 4.91 (q, 1H), 5.97 (d, 1H), 7.18~7.71 (m, 9H)

2-Acetylamino-3-(4-biphenyl)propionic acidethylester (4.4 g, 14.1 mmol) was added to 6N—HCl solution and reacted with reflux for 12 hours. Then, the solution was cooled down to RT and filtered to obtain a solid which was then washed with water and dried under reduced pressure finally to prepare 2-amino-3-(4-biphenyl)propionic acid hydrochloride (3.2 g, 82%).

$^1$H NMR (300 MHz, DMSO-d$_6$): δ 3.05 (dd, 1H), 3.20 (dd, 1H), 3.84 (t, 1H), 7.37 (m, 3H), 7.47 (t, 2H), 7.65 (m, 4H)

2-Amino-3-(4-biphenyl)propionic acid hydrochloride (3.2 g, 11.6 mmol) was dissolved in methanol and cooled down at 0° C. And, thionyl chloride (4.53 mL, 5 equi.) was slowly added and the temperature was elevated to RT. And then, the solution was stirred for 12 hours and the solvent was removed from the solution to give a solid, which was dispersed in diisopropyl ether, stirred for 1 hour and filtered, finally to prepare methyl 2-amino-3-(4-biphenyl)propionate hydrochloride (3.3 g, 98%).

$^1$ H NMR (300 MHz, DMSO-d$_6$): δ 3.14 (t, 2H), 3.72 (s, 3H), 4.37 (t, 1H), 7.37 (m, 3H), 7.47 (t, 2H), 7.66 (m, 4H), 8.41 (bs, 2H)

EXAMPLE 54

(±)-2-Amino-3-(2-phenylthiazole-4-yl) propionic Acid Dihydrochloride

The titled compound, 2-amino-3-(2-phenylthiazole-4-yl) propionic acid dihydrochloride (0.52 g, 20%) was prepared in a similar manner as in Example 14, except for employing diethyl acetamidomalonate (1.76 g, 8.1 mmol) and 2-phenylthiazole-5-methylchloride (1.54 g, 7.35 mmol).

$^1$H NMR (300 MHz, DMSO-d$_6$): δ 2.72 (m, 2H), 4.35 (m, 1H), 7.50 (m, 4H), 7.95 (m, 2H), 8.30 (bs, 2H)

EXAMPLE 55

(±)-2-amino-3-(imidazo[1,2-a]pyridine-3-yl) propionic acid Trihydrochloride

The titled compound, 2-amino-3-(imidazo[1,2-a] pyridine-3-yl)propionic acid trihydrochloride (1.38 g, 22%), was prepared in a similar manner as in Example 14, except for employing diethyl acetamidomalonate (4.78 g, 22 mmol) and imidazo[1,2-a]pyridine-3-methylchloride (3.33 g, 20 mmol).

$^1$H NMR (300 MHz, DMSO-d$_6$): δ 3.5 (m, 2H), 4.48 (t, 1H), 7.49 (m, 1H), 7.96 (m, 2H), 8.28 (s, 1H), 8.98 (d, 1H)

EXAMPLE 56

(±)-2-amino-4-phenylbutyric Acid Methylester Hydrochloride

Sodium (0.515 g, 1.1 equi.) was completely dissolved in absolute ethanol and N-(t-butoxycarbonylamino)malonic acid diethylester (5.6 g, 20.37 mmol) was added, followed by stirring for 1 hour. Then, phenethyl bromide (3.06 mL, 1.1 equi.) and KI (0.1 equi.) were added and reacted at a temperature of 50–60° C. for 12 hours. After starting material, phenethyl bromide, was completely exhausted, the solvent was distilled under reduced pressure and the product was extracted with water/ethylacetate (100 mL/100 mL). Then, the separated organic phase was washed with 1N HCl, dried over anhydrous MgSO$_4$ and dried under reduced pressure to give N-(t-butoxycarbonyl)amino-2-phenethylmalonic acid diethylester. Without purification, both of the two esters were hydrolyzed with 5N—NaOH aqueous solution (5 equi.) and the compound was decarbonated in 1,4-dioxane, finally to prepare 2-N-(t-butoxycarbonyl) amino-4-phenylbutyric acid (4.18 g, 75%).

$^1$H NMR (300 MHz, CDCl$_3$): δ 1.45 (s, 9H), 1.98 (m, 1H), 2.19 (m, 1H), 2.72 (t, 2H), 4.0 (m, 1H), 4.35 (m, 1H), 5.0 (bs, 1H), 7.19 (m, 3H), 7.29 (m, 2H)

2-N-(t-butoxycarbonyl)amino-4-phenylbutyric acid (4.18 g, 15 mmol) was dissolved in methanol and cooled down to 0° C. and thionyl chloride (5.9 mL, 5 equi.) was slowly added. Then, the temperature was elevated to RT and the solution was stirred for 12 hours. The solvent was removed from the solution to give a solid product, which was then dispersed in diisopropyl ether, stirred for 1 hour and filtered, finally to prepare 2-amino-4-phenylbutyric acid methylester hydrochloride (2.9 g, 85%).

$^1$H NMR (300 MHz, D$_2$O): δ 2.15 (m, 2H), 2.66 (m, 2H), 3.72 (s, 3H), 4.04 (t, 1H), 7.18 (m, 3H), 7.27 (m, 2H)

EXAMPLE 57

(±)-2-amino-5-phenylvaleric Acid Methylester

Sodium (0.49 g, 1.1 equi.) was completely dissolved in absolute ethanol and N-(t-butoxycarbonylamino)malonic acid diethylester (5.33 g, 19.35 mmol) was added in a solid form, followed by stirring for 1 hour. Then, phenylpropyl bromide (3.23 mL, 1.1 equi.) and KI (0.1 equi.) were added and reacted at a temperature of 50–60° C. for 12 hours. After starting material, phenylpropyl bromide, was completely exhausted, the solvent was distilled under reduced pressure and the product was extracted with water/ethylacetate (100 mL/10 mL). Then, the separated organic phase was washed with 1N HCl, dried over anhydrous MgSO$_4$ and dried under reduced pressure to give 2-N-(t-butoxycarbonyl)amino-5-phenylvaleric acid (4.5 g, 80%). Without purification, both of the two esters were hydrolyzed with 5N—NaOH aqueous solution (5 equi.) and the compound was decarbonated in 1,4-dioxane to prepare 2-N-(t-butoxycarbonyl)amino-5-phenylvaleric acid (4.5 g, 80%).

$^1$H NMR (300 MHz, CDCl$_3$): δ 1.43 (s, 9H), 1.68 (m, 3H), 1.90 (m, 1H), 2.63 (m, 2H), 3.96 (m, 1H), 4.34 (m, 1H), 4.97 (m, 1H), 7.18 (m, 3H), 7.28 (m, 2H)

2-N-(t-butoxycarbonyl)amino-5-phenylvaleric acid (4.5 g, 15.48 mmol) was dissolved in methanol and cooled down to 0° C., and thionyl chloride (6 mL, 5 equi.) was slowly added. Then, the temperature was elevated to RT and the solution was stirred for 12 hours. The solvent was removed from the solution to give a solid product, which was then dispersed in diisopropyl ether, stirred for 1 hour and filtered, finally to prepare 2-amino-5-phenylvaleric acid methylester hydrochloride (3.2 g, 85%).

$^1$H NMR (300 MHz, D$_2$O): δ 1.6 (m, 2H), 1.83 (m, 2H), 2.58 (t, 2H), 3.72 (s, 3H), 4.02 (t, 1H), 7.16 (m, 3H), 7.26 (m, 2H)

EXAMPLE 58

(D)-3-(4-allyloxyphenyl)-2-aminopropionic Acid Methylester Hydrochloride (D)-N-t-Butylcarboxytyrosine methylester (5.6 g, 19 mmol) was dissolved in acetone (69 mL). K$_2$CO$_3$ (3.92 g, 1.5 equi.) and KI (0.314 g, 0.1 equi.) were added to the solution and then, allyl bromide (1.7 mL, 1.2 equi.) was slowly added. Then, the reaction solution was refluxed for 12 hours. After starting material was completely exhausted, the solvent was distilled under reduced pressure and the product was extracted with water/ethylacetate (100 mL/100 mL). The organic phase was washed with water, dried over anhydrous MgSO$_4$ and dried under reduced pressure to give (D)-3-(4-allyloxyphenyl)-2-(N-t-butylcarboxy) aminopropionic acid methylester (6 g, 95%). Without purification, the compound was dissolved in ethylacetate (50 mL) and cooled down to 0° C. and then, passed through by anhydrous HCl (5 equi.) gas. After leaving to stand at RT for 5 hours, the solution was filtered to give a solid, which was then dried under reduced pressure finally to prepare (D)-3-(4-allyloxyphenyl)-2-aminopropionic acid methylester hydrochloride (3.9 g, 79%).

$^1$H NMR (300 MHz, D$_2$O): δ 3.13 (m, 2H), 3.74 (s, 3H), 4.30 (m, 1H), 4.53 (m, 2H), 5.22 (d, 1H), 5.33 (d, 1H), 6.04 (m, 1H), 6.92 (d, 2H), 7.13 (d, 2H)

EXAMPLE 59

(D)-3-(4-Propargyloxyphenyl)-2-aminopropionic Acid Methylester Hydrochloride (D)-N-t-butylcarboxytyrosine methylester (4.35 g, 14.7 mmol) was dissolved in acetone (60 mL). K$_2$CO$_3$ (3.04 g, 1.5 equi.) and KI (0.24 g, 0.1 equi.) were added to the solution and then, propargyl bromide (1.97 mL, 1.2 equi.) was slowly added. Then, the reaction solution was refluxed for 12 hours. After starting material was completely exhausted, the solvent was distilled under reduced pressure and the product was extracted with water/ethylacetate (100 mL/100 mL). The organic phase was washed with water, dried over anhydrous MgSO$_4$ and dried under reduced pressure to give (D)-3-(4-propargyloxyphenyl)-2-(N-t-butylcarboxy) aminopropionic acid methylester (4.9 g, 100%). Without purification, the compound was dissolved in ethylacetate (50 mL) and cooled down to 0° C. and then, passed through anhydrous HCl (5 equi.) gas. After leaving to stand at RT for 5 hours, the solution was filtered to give a solid, which was then dried under reduced pressure to prepare (D)-3-(4-propargyloxyphenyl)-2-aminopropionic acid methylester hydrochloride (3.78 g, 95%).

$^1$H NMR (300 MHz, D$_2$O): δ 2.83 (t, 1H), 3.16 (dd, 1H), 3.21 (dd, 1H), 3.73 (s, 3H), 4.28 (t, 1H), 6.97 (d, 2H), 7.24 (d, 2H)

EXAMPLE 60

(D)-3-(4-benzyloxyphenyl)-2-aminopropionic Acid Methylester Hydrochloride (D)-N-t-butylcarboxytyrosine methylester (1.46 g, 4.94 mmol) was dissolved in acetone (20 mL). K$_2$CO$_3$ (1.02 g, 1.5 equi.) and KI (0.082 g, 0.1 equi.) were added to the solution and then, benzyl bromide (0.7 mL, 1.2 equi.) was slowly added. Then, the reaction solution was refluxed for 12 hours. After starting material was completely exhausted, the solvent was distilled under reduced pressure and the product was extracted with water/ethylacetate (100 mL/100 mL). The organic phase was washed with water, dried over anhydrous MgSO$_4$ and dried under reduced pressure to give (D)-3-(4-benzyloxyphenyl)-2-(N-t-butylcarboxy) aminopropionic acid methylester (1.9 g, 100%). Without purification, the compound was dissolved in ethylacetate (20 mL) and cooled down to 0° C. and then, passed through anhydrous HCl (5 equi.) gas. After leaving to stand at RT for 12 hours, the solution was filtered to give a solid, which was then dried under reduced pressure to prepare (D)-3-(4-benzyloxyphenyl)-2-aminopropionic acid methylester hydrochloride (1.48 g, 93%).

$^1$H NMR (300 MHz, D$_2$O): δ 3.08 (dd, 1H), 3.14 (dd, 1H), 3.71 (s, 3H), 4.25 (t, 1H), 5.07 (s, 2H), 6.95 (d, 2H), 7.11 (d, 2H), 7.35 (m, 5H)

EXAMPLE 61

(D)-3-(4-(2-phenethyl)oxyphenyl)-2-aminopropionic Acid Methylester Hydrochloride (D)-N-t-butylcarboxytyrosine methylester (1.56 g, 5.35 mmol) was dissolved in acetone (20 mL). K$_2$CO$_3$ (1.11 g, 1.5 equi.) and KI (0.089 g, 0.1 equi.) were added to the solution and then, phenethyl bromide (0.88 mL, 1.2 equi.) was slowly added. Then, the reaction solution was refluxed for 48 hours. And then, the solvent was distilled under reduced pressure and the product was extracted with water/ethylacetate (40 mL/40 mL). The organic phase was washed with water, dried over anhydrous MgSO$_4$, and then, purified on silica gel chromatography using ethylacetate/n-hexane (1/4) and dried under reduced pressure to give (D)-3-(4-(2-phenethyl)oxyphenyl)-2-(N-t-butylcarboxy)aminopropionic acid methylester (1.28 g, 60%). The compound was dissolved in ethylacetate (20 mL) and cooled down to 0° C. and then, passed through anhydrous HCl (5 equi.) gas. After leaving to stand at RT for 12 hours, the solution was filtered to give a solid, which was then dried under reduced pressure finally to prepare (D)-3-(4-(2-phenethyl)oxyphenyl)-2-aminopropionic acid methylester hydrochloride (1.08 g, 100%).

$^1$H NMR (300 MHz, D$_2$O): δ 2.99 (t, 2H), 3.08 (dd, 1H), 3.13 (dd, 1H), 3.72 (s, 3H), 4.23 (t, 2H), 4.25 (t, 1H), 6.87 (d, 2H), 7.10 (d, 2H), 7.25 (m, 5H)

EXAMPLE 62

(D)-3-(4-(3-phenyl-1-propyl)oxyphenyl)-2-aminopropionic Acid Methylester Hydrochloride (D)-N-t-butylcarboxytyrosine methylester (1.51 g, 5.12 mmol) was dissolved in acetone (20 mL). K$_2$CO$_3$ (1.06 g, 1.5 equi.) and KI (0.085 g, 0.1 equi.) were added to the solution and then, 3-phenyl-1-propane bromide (0.93 mL, 1.2 equi.) was slowly added. Then, the reaction solution was refluxed for 24 hours. After starting material was completely exhausted, the solvent was distilled under reduced pressure and the product was extracted with water/ethylacetate (40 mL/40 mL). The organic phase was washed with water, dried over anhydrous MgSO$_4$ and dried under reduced pressure to give (D)-3-(4-(3-phenyl-1-propyl)oxyphenyl)-2-(N-t-butylcarboxy)aminopropionic acid methylester. Without purification, the compound was dissolved in ethylacetate (20 mL) and cooled down to 0° C. and then, passed through anhydrous HCl (5 equi.) gas. After leaving to stand at RT for 12 hours, the solution was filtered to give a solid, which was then dried under reduced pressure finally to prepare (D)-3-(4-(3-phenyl-1-propyl)oxyphenyl)-2-aminopropionic acid methylester hydrochloride (0.9 g, 50%).

$^1$H NMR (300 MHz, D$_2$O): δ 1.99 (p, 2H), 2.70 (t, 2H), 3.08 (dd, 1H), 3.13 (dd, 1H), 3.71 (s, 3H), 3.93 (t, 2H), 4.24 (t, 1H), 6.87 (d, 2H), 7.10 (d, 2H), 7.21 (m, 5H)

EXAMPLE 63
(D)-3-(4-(3-phthalimido-1-propyl)oxyphenyl)-2-aminopropionic Acid Methylester Hydrochloride (D)-N-t-butylcarboxytyrosine methylester (1.26 g, 4.28 mmol) was dissolved in acetone (20 mL). K$_2$CO$_3$ (0.89 g, 1.5 equi.) and KI (0.071 g, 0.1 equi.) were added to the solution and then, N-(3-bromopropyl)phthalimide(1.38 g, 1.2 equi.) was slowly added. Then, the reaction solution was refluxed for 12 hours. And then, the solvent was distilled under reduced pressure and the product was extracted with water/ethylacetate (40 mL/40 mL). The organic phase was washed with water, dried over anhydrous MgSO$_4$, and then, purified on silica gel chromatography using ethylacetate/n-hexane (1/2) and dried under reduced pressure to give (D)-3-(4-(3-phthalimido-1-propyl)oxyphenyl)-2-(N-t-butylcarboxy) aminopropionic acid methylester (1.34 g, 65%). The compound was dissolved in ethylacetate (20 mL) and cooled down to 0° C. and then, passed through anhydrous HCl (5 equi.) gas. After leaving to stand at RT for 12 hours, the solution was filtered to give a solid, which was then dried under reduced pressure finally to prepare (D)-3-(4-(3-phthalimido-1-propyl)oxyphenyl)-2-aminopropionic acid methylester hydrochloride (1.07 g, 92%).

$^1$H NMR (300 MHz, D$_2$O): δ 2.04 (p, 2H), 3.00 (dd, 1H), 3.09 (dd, 1H), 3.70(s, 3H), 3.76 (t, 2H), 4.01 (t, 2H), 4.19 (t, 1H), 6.56 (d, 2H), 6.96 (d, 2H), 7.70 (s, 4H)

EXAMPLE 64
(2R)-2-[(2-heptylthiobenzthiazol-6-sulfonyl) amino]-3-(4-allyloxy) Phenylpropionic Acid (D)-3-(4-allyloxyphenyl)-2-aminopropionic acid methylester hydrochloride (0.112 g, 0.41 mmol) prepared in Example 19 was dispersed in dichloromethane (10 mL) and cooled down to 0° C. and then, triethylamine (0.17 mL, 3 equi.) was added. 2-n-Heptylthio-6-benzthiazolsulfonyl chloride (0.180 g, 1.2 equi.) prepared in Example 7 was dissolved in dichloromethane (2 mL) to give a dichloromethane solution. Then, the dichloromethane solution was added while maintaining the temperature of 0° C. When starting material was disappeared after 5 hours, the organic phase was washed with 1N HCl solution, dried over anhydrous MgSO$_4$, distilled under reduced pressure and vacuum-dried to prepare (2R)-2-[(2-heptylthiobenzthiazol-6-sulfonyl)amino]-3-(4-allyloxy) phenylpropionic acid methylester (0.204 g, 88%).

$^1$H NMR (300 MHz, CDCl$_3$): δ 0.89 (t, 3H), 1.3 (m, 6H), 1.5 (m, 2H), 1.8(p, 2H), 2.96(dq, 2H), 3.36 (t, 2H), 3.48 (s, 3H), 4.15 (m, 1H), 4.46 (m, 2H), 5.18 (d, 1H), 5.27 (d, 1H), 5.43 (d, 1H), 6.05 (m, 1H), 6.74 (d, 2H), 6.94 (d, 2H), 7.71 (d, 1H), 7.85 (d, 1H), 8.11 (s, 1H)

(2R)-2-[(2-heptylthiobenzthiazol-6-sulfonyl)amino]-3-(4-allyloxy)phenylpropionic acid methylester (0.204 g, 0.36 mmol) was dissolved in THF/H$_2$O (2 mL/2 mL) and LiOH (0.076 g, 5 equi.) was added, and reacted with reflux for 12 hours. Then, the solution was distilled under reduced pressure and treated with 1N HCl. The product was extracted with ethylacetate (10 mL). The separated organic phase was washed with NaCl solution, dried over anhydrous MgSO$_4$, distilled under reduced pressure and dried under vacuum to prepare the titled compound, (2R)-2-[(2-heptylthiobenzthiazol-6-sulfonyl)amino]-3-(4-allyloxy) phenylpropionic acid (0.71 mg, 86%).

$^1$H NMR (300 MHz, CDCl$_3$): δ 0.85 (t, 3H), 1.28 (m, 6H), 1.45 (m, 2H), 1.80 (m, 2H), 2.87 (dd, 1H), 3.03 (dd, 1H), 3.31 (t, 2H), 4.16 (m, 1H), 4.40 (m, 2H), 5.25 (d, 1H), 5.37 (d, 1H), 5.77 (d, 1H), 6.01 (m, 1H), 6.66 (d, 2H), 6.97 (d, 2H), 7.71 (d, 1H), 7.79 (d, 1H), 8.04 (s, 1H), 8.96 (s, 1H)

Using (D)-3-(4-propargyloxyphenyl)-2-aminopropionic acid methylester hydrochloride obtained in Example 59, the following titled compound, (2R)-2-[(2-heptylthiobenzthiazol-6-sulfonyl)amino]-3-(4-propargyloxy)phenylpropionic acid, was prepared in a similar manner as aboves.

$^1$H NMR (300 MHz, CDCl$_3$): δ 0.89 (t, 3H), 1.29 (m, 6H), 1.48 (m, 2H), 1.83 (m, 2H), 2.53 (s, 1H), 2.91 (dd, 1H), 3.00 (dd, 1H), 3.35 (m, 2H), 4.2 (m, 1H), 4.63 (s, 2H), 5.30 (d, 1H), 6.79 (d, 2H), 7.0 (d, 2H), 7.70 (d, 1H), 7.81 (d, 1H), 8.10 (s, 1H)

Using (D)-3-(4-benzyloxyphenyl)-2-aminopropionic acid methylester hydrochloride obtained in Example 60, (2R)-2-[(2-heptylthiobenzthiazol-6-sulfonyl)amino]-3-(4-bentyloxyphenyl)propionic acid was prepared in a similar manner as aboves.

$^1$H NMR (300 MHz, CDCl$_3$): δ 0.9 (t, 3H), 1.30 (m, 6H), 1.44 (m, 2H), 1.83 (m, 2H), 2.96 (dd, 1H), 3.08 (dd, 1H), 3.33 (t, 2H), 4.25 (m, 1H), 5.0 (s, 1H), 5.1 (d, 1H), 6.8 (d, 2H), 7.0 (d, 2H), 7.43 (m, 5H), 7.73 (d, 1H), 7.83 (d, 1H), 8.11 (s, 1H)

Using (D)-3-(4-(2-phenethyl)oxyphenyl)-2-aminopropionic acid methylester hydrochloride obtained in Example 61, the following titled compound, (2R)-2-[(2-heptylthiobenzthiazol-6-sulfonyl)amino]-3-(4-(2-phenethyl)oxyphenyl)propionic acid, was prepared in a similar manner as aboves.

$^1$H NMR (300 MHz, CDCl$_3$): δ 0.9 (t, 3H), 1.26 (m, 6H), 1.45 (m, 2H), 1.83 (m, 2H), 2.9 (dd, 1H), 3.09 (m, 3H), 3.4 (m, 2H), 4.09 (t, 2H), 4.25 (m, 1H), 5.3 (d, 1H), 6.7 (d, 1H), 7.0 (d, 2H), 7.3 (m, 5H), 7.85 (dd, 2H), 8.12 (s, 1H)

Using (D)-3-(4-(3-phenyl-1-propyl)oxyphenyl)-2-aminopropionic acid methylester hydrochloride obtained in Example 62, the following titled compound, (2R)-2-[(2-heptylthiobenzthiazol-6-sulfonyl)amino]-3-(4-(3-phenyl-1-propyl)oxyphenyl)propionic acid, was prepared in a similar manner as aboves.

$^1$H NMR (300 MHz, CDCl$_3$): δ 0.85 (, 3H), 1.27 (m, 6H), 1.42 (m, 2H), 1.78 (m, 2H), 2.06 (m, 2H), 2.88 (dd, 1H), 3.02 (dd, 1H), 3.31 (t, 2H), 3.83 (t, 2H), 4.18 (m, 1H), 5.75 (d, 1H), 6.64 (d, 2H), 6.97 (d, 2H), 7.16 (m, 5H), 7.79 (dd, 2H), 8.06 (s, 1H), 8.85 (s, 1H)

Using (D)-3-(4-(3-phthalimido1-propyl)oxyphenyl)-2-aminopropionic acid methylester hydrochloride obtained in Example 63, the following titled compound, (2R)-2-[(2-heptylthiobenzthiazol-6-sulfonyl)amino]-3-(4-(3-phthalimido-1-propyl)oxyphenyl)propionic acid, was prepared in a similar manner as aboves.

$^1$H NMR (300 MHz, CDCl$_3$): δ 0.88 (t, 3H), 1.23 (m, 6H), 1.43 (m, 2H), 1.83 (m, 2H), 2.15 (m, 2H), 2.90 (m, 2H), 3.36 (t, 2H), 3.93 (m, 4H), 4.2 (m, 1H), 5.3 (d, 1H), 6.62 (d, 2H), 6.9 (d, 2H), 7.71 (m, 3H), 7.84 (m, 3H), 8.11 (s, 1H)

Using (±)-2-amino-4-phenylbutyric acid methylester hydrochloride synthesized in Example 56, the following titled compound, (±)-2-[(2-heptylthiobenzthiazol-6-sulfonyl)amino]-4-phenylbutyric acid, was prepared in a similar manner as aboves.

¹H NMR(300 MHz, CDCl₃): δ 0.9 (t, 3H), 1.30 (m, 6H), 1.46 (m, 2H), 1.82 (p, 2H), 2.0 (m, 1H), 2.17 (m, 1H), 2.72 (m, 2H), 3.32 (t, 2H), 4.0 (m, 1H), 5.32 (d, 1H), 7.0 (d, 2H), 7.25 (m, 3H), 7.85 (dd, 2H), 8.24 (s, 1H)

Using (±)-2-amino-5-phenylvaleric acid methylester hydrochloride obtained in Example 57, (±)-2-[(2-heptylthiobenzthiazol-6-sulfonyl)amino]-5-phenylvaleric acid was prepared in a similar manner as aboves.

¹H NMR (300 MHz, CDCl₃): δ 0.89 (t, 3H), 1.31 (m, 6H), 1.45 (m, 2H), 1.67 (m, 3H), 1.82 (m, 3H), 2.58 (m, 2H), 3.32 (t, 2H), 4.0 (m, 1H), 5.23 (d, 1H), 7.0 (d, 2H), 7.25 (m, 3H), 7.84 (dd, 2H), 8.26 (s, 1H)

EXAMPLE 65

(2R)-N-hydroxy-2-[(2-heptylthiobenzthiazol-6-sulfonyl)amino]-3-(4-allyloxy) Phenylpropionic Amide (2R)-2-[(2-heptylthiobenzthiazol-6-sulfonyl)amino]-3-(4-allyloxy)phenylpropionic acid (0.17 g, 0.31 mmol) prepared in Example 64 was dissolved in dichloromethane (2 mL) and cooled down to 0° C. Then, oxalylchloride (0.14 mL, 5 equi.) and DMF of catalytic amount were added. After reaction for 3 hours at RT, the reaction solution was distilled under reduced pressure to remove the solvent and dried under reduced pressure to give (2R)-2-[(2-heptylthiobenzthiazol-6-sulfonyl)amino]-3-(4-allyloxy) phenylpropionyl chloride which was then dissolved in THF (1 mL). Hydroxylamine hydrochloride (0.215 g, 10 equi.) and NaHCO₃ (0.260 g, 10 equi.) were dissolved in THF/H₂O (1 mL/1 mL) and cooled down to 0° C. The acid chloride/THF solution was slowly added to hydroxylamine solution while maintaining the temperature of 0° C. After 1 hour, the solvent was removed from the reaction solution. Then, the product was extracted with ethylacetate (5 mL), washed with H₂O and 0.1N HCl, dried over anhydrous MgSO₄, distilled under reduced pressure and vacuum-dried to prepare the titled compound, (2R)-N-hydroxy-2-[(2-heptylthiobenzthiazol-6-sulfonyl) amino]-3-(4-allyloxy) phenylpropionic amide (0.157 g, 90%).

¹H NMR (300 MHz, CDCl₃): δ 0.89 (t, 3H), 1.3 (m, 6H), 1.44 (m, 2H), 1.78 (m, 2H), 2.74 (m, 1H), 3.09 (m, 1H), 3.32 (t, 1H), 4.09 (s, 2H), 5.24 (d, 1H), 5.35 (d, 1H), 5.93 (m, 1H), 6.31 (d, 1H), 6.77 (m, 4H), 7.6 (m, 2H), 7.85 (s, 1H), 10.6 (s, 1H)

Using (2R)-2-[(2-heptylthiobenzthiazol-6-sulfonyl)amino]-3-(4-propargyloxy)phenylpropionic acid obtained in Example 64, the following titled compound, (2R)-N-hydroxy-2-[(2-heptylthiobenzthiazol-6-sulfonyl)amino]-3-(4-propargyloxy)phenylpropionic amide, was prepared in a similar manner as aboves.

¹H NMR (300 MHz, CDCl₃): δ 0.88 (t, 3H), 1.23 (m, 6H), 1.43 (m, 2H), 1.80 (m, 2H), 2.47 (d, 1H), 2.8 (m, 1H), 3.05 (m, 1H), 3.32 (t, 2H), 4.03 (m, 1H), 4.42 (s, 2H), 6.40 (d, 2H), 6.50 (m, 1H), 6.78 (d, 2H), 7.48 (d, 1H), 7.62 (d, 1H), 7.86 (s, 1H), 10.4 (s, 1H)

Using (2R)-2-[(2-heptylthiobenzthiazol-6-sulfonyl)amino]-3-(4-benzyloxyphenyl)propionic acid obtained in Example 64, (2R)-N-hydroxy-2-[(2-heptylthiobenzthiazol-6-sulfonyl)amino]-3-(4-benzyloxyphenyl)propionic amide was prepared in a similar manner as aboves.

¹H NMR(300 MHz, CDCl₃): δ 0.87 (t, 3H), 1.26 (m, 6H), 1.44 (m, 2H), 1.83 (m, 2H), 2.88 (dd, 1H), 3.18 (m, 3H), 4.12 (m, 1H), 4.75 (s, 2H), 6.44 (d, 2H), 7.0 (d, 2H), 7.3 (m, 5H), 7.65 (dd, 2H), 7.9 (s, 1H)

Using (2R)-2-[(2-heptylthiobenzthiazol-6-sulfonyl)amino]-3-(4-(2-phenylethyl)oxyphenyl)propionic acid obtained in Example 64, (2R)-N-hydroxy-2-[(2-heptylthiobenzthiazol-6-sulfonyl)amino]-3-(4-(2-phenylethyl)oxyphenyl)propionic amide was prepared in a similar manner as aboves.

¹H NMR (300 MHz, CDCl₃): δ 0.88 (t, 3H), 1.26 (m, 6H), 1.43 (m, 2H), 1.81 (m, 2H), 2.92 (dd, 1H), 3.07 (m, 2H), 3.3 (m, 1H), 3.37 (t, 2H), 3.96 (m, 2H) 4.1 (m, 1H), 5.2 (d, 1H), 6.4 (s, 1H), 6.7 (d, 2H), 6.93 (d, 2H), 7.29 (m, 5H), 7.73 (d, 1H), 7.81 (d, 1H), 7.93 (s, 1H), 8.1 (s, 1H)

Using (2R)-2-[(2-heptylthiobenzthiazol-6-sulfonyl)amino]-3-(4-(3-phenyl-1-propyl)oxyphenyl) propionic acid obtained in Example 64, (2R)-N-hydroxy-2-[(2-heptylthiobenzthiazol-6-sulfonyl)amino]-3-(4-(3-phenyl-1-propyl)oxyphenyl) propionic amide was prepared in a similar manner as aboves.

¹H NMR (300 MHz, CDCl₃): δ 0.85 (t, 3H), 1.23 (m, 6H), 1.42 (m, 2H), 1.74 (m, 2H), 2.01 (m, 2H), 2.75 (m, 1H), 3.21 (m, 3H), 3.74 (m, 2H), 4.1 (m, 1H), 6.4 (d, 2H), 6.8 (d, 2H), 7.66 (m, 5H), 8.0 (m, 3H)

Using (2R)-2-[(2-heptylthiobenzthiazol-6-sulfonyl)amino]-3-(4-(3-phthalimido-1-propyl)oxyphenyl)propionic acid obtained in Example 64, (2R)-N-hydroxy-2-[(2-heptylthiobenzthiazol-6-sulfonyl)amino]-3-(4-(3-phthalimido-1-propyl)oxyphenyl)propionic amide was prepared in a similar manner as aboves.

¹H NMR (300 MHz, CDCl₃): δ 0.88 (t, 3H), 1.3 (m, 6H), 1.43 (m, 2H), 1.77 (m, 2H), 2.05 (m, 2H), 2.77 (m, 3H), 3.0 (m, 1H), 3.31 (m, 2H), 3.72 (t, 2H), 4.05 (m, 1H), 6.05 (bs, 1H), 6.4 (d, 2H), 6.78 (d, 2H), 7.21 (m, 4H), 7.63 (dd, 2H), 7.9 (s, 1H), 10.1 (bs, 1H)

Using (±)-2-[(2-heptylthiobenzthiazol-6-sulfonyl)amino]-4-phenylbutyric acid obtained in Example 64, (±)-N-hydroxy-2-[(2-heptylthiobenzthiazol-6-sulfonyl)amino]-4-phenylbutyric amide was prepared in a similar manner as aboves.

¹H NMR (300 MHz, CDCl₃): δ 0.88 (t, 3H), 1.23 (m, 6H), 1.45 (m, 2H), 1.77 (m, 3H), 2.05 (m, 1H), 2.34 (m, 2H), 3.33 (t, 2H), 3.80 (bs, 1H), 6.8 (m, 2H), 6.9 (m, 3H), 7.8 (m, 2H), 8.2 (s, 1H), 10.2 (bs, 1H)

Using (±)-2-[(2-heptylthiobenzthiazol-6-sulfonyl)amino]-5-phenylvaleric acid obtained in Example 64, (±)-N-hydroxy-2-[(2-heptylthiobenzthiazol-6-sulfonyl)amino]-5-phenylvaleric amide was prepared in a similar manner as aboves.

¹H NMR (300 MHz, CDCl₃): δ 0.88 (t, 3H), 1.29 (m, 6H), 1.43 (m, 2H), 1.70 (m, 3H), 1.87 (m, 3H), 2.30 (m, 2H), 3.36 (t, 2H), 3.83 (bs, 1H), 6.5 (bs, 1H), 6.8 (m, 2H), 7.06 (m, 3H), 7.82 (m, 2H), 8.23 (s, 1H), 10.04 (bs, 1H)

EXAMPLE 66

(2R)-2-[(2-chlorobenzthiazol-6-sulfonyl) amino]-3-(4-(3-phthalimido-1-propyl) oxyphenyl)propionic Acid Methylester (D)-3-(4-(3-phthalimido-1-propyl)oxyphenyl)-2-aminopropionic acid methylester hydrochloride (0.49 g, 1.17 mmol) was dispersed in dichloromethane (5 mL) and cooled down to 0° C., and triethylamine (0.5 mL, 3 equi.) was added. 2-Chloro-6-benzthiazolsulfonyl chloride (0.38 g, 1.2 equi.) prepared in Example 13 was dissolved in dichloromethane (3 mL) to give a dichloromethane solution. Then, the dichloromethane solution was added while maintaining the temperature of 0° C. When starting material was exhausted after 1 hour, the organic phase was washed with 1N HCl, dried over anhydrous MgSO₄ and distilled under reduced pressure. Then, the product was purified on silica gel chromatography using ethylacetate/n-hexane (1/2) to prepare the titled compound, (2R)-2-[(2-chlorobenzthiazol-6-sulfonyl)amino]-3-(4-(3-phthalimido-1-propyl) oxyphenyl) propionic acid methylester (0.7 g, 97%).

¹H NMR (300 MHz, CDCl₃): δ 2.17 (m, 2H), 2.98 (m, 2H), 3.52 (s, 3H), 3.93 (m, 4H), 4.15 (m, 1H), 5.4 (d, 1H), 6.62 (d, 2H), 6.9 (d, 2H), 7.73 (m, 3H), 7.86 (m, 3H), 8.0 (s, 1H)

EXAMPLE 67

(2R)-2-[(2-(4-methoxyphenylthio)benzthiazol-6-sulfonyl) amino]-3-(4-(3-phthalimido-1-propyl)oxyphenyl)propionic Acid Methylester (2R)-2-[(2-Chlorobenzthiazol-6-sulfonyl)amino]-3-(4-(3-phthalimido-1-propyl)oxyphenyl)propionic acid methylester (0.24 g, 0.39 mmol) prepared in a similar manner as in Example 59 was dissolved in MeCN (3 mL). $K_2CO_3$ (0.081 g, 1.5 equi.) were added to the solution in a solid form and then, 4-methoxybenzthiol (0.053 mL, 1.1 equi.) was added and refluxed for 3 hours. After starting material was exhausted, water/ethylacetate (5 mL/10 mL) was added and the product was extracted with an organic solvent. The organic phase was washed with NaCl solution, dried over anhydrous $MgSO_4$, distilled under reduced pressure and then, purified on silica gel chromatography using ethylacetate/n-hexane (1/2) to prepare the titled compound, (2R)-2-[(2-(4-methoxyphenylthio)benzthiazol-6-sulfonyl) amino]-3-(4-(3-phthalimido-1-propyl)oxyphenyl)propionic acid methylester (0.2 g, 70%).

$^1$H NMR (300 MHz, $CDCl_3$): δ 2.13 (m, 2H), 2.91 (m, 2H), 3.42 (s, 3H), 3.85 (s, 3H), 3.93 (m, 4H), 4.0 (m, 1H), 5.27 (d, 1H), 6.57 (d, 2H), 6.85 (d, 2H), 7.0 (d, 2H), 7.62 (d, 2H), 7.68 (m, 3H), 7.81 (m, 3H), 8.0 (s, 1H)

EXAMPLE 68

(2R)-2-[(2-(4-methoxyphenylthio)benzthiazol-6-sulfonyl) amino]-3-(4-(3-phthalimido-1-propyl)oxyphenyl)propionic Acid (2R)-2-[(2-(4-Methoxyphenylthio)benzthiazol-6-sulfonyl)amino]-3-(4-(3-phthalimido-1-propyl)oxyphenyl) propionic acid methylester (0.196 g, 0.27 mmol) prepared in Example 61 was dissolved in $THF/H_2O$ (2 mL/2 mL), and LiOH(0.057 g, 5 equi.) was added and refluxed for 12 hours. Then, the reaction solution was distilled under reduced pressure to remove the solvent and treated with 1N HCl. The product was extracted with ethylacetate (10 mL). The separated organic phase was washed with NaCl solution, dried over anhydrous $MgSO_4$, distilled under reduced pressure and dried under vacuum to prepare the titled compound, (2R)-2-[(2-(4-methoxyphenylthio)benzthiazol-6-sulfonyl) amino]-3-(4-(3-phthalimido-1-propyl)oxyphenyl) propionic acid (0.15 g, 80%).

$^1$H NMR(300 MHz, MeOH-$d_4$): δ 2.09 (m, 2H), 2.6 (dd, 1H), 2.9 (dd, 1H), 3.87 (s, 3H), 3.95 (m, 4H), 4.0 (m, 1H), 6.25 (d, 1H), 6.51 (d, 2H), 6.87 (d, 2H), 7.12 (d, 2H), 7.55 (m, 5H), 7.71 (m, 3H), 7.95 (s, 1H)

EXAMPLE 69

Preparation of N-hydroxy-(2R)-3-methyl-2-[(2-n-hexylthiobenzthiazol-6-sulfonyl) ethoxycarbonylmethylamino]butyric Amide (2R)-3-Methyl-2-[(2-n-hexylthiobenzthiazol-6-sulfonyl) amino]butanoic acid (7.9 g, 0.018 mol) prepared in Example 18-7 was dissolved in acetone (100 mL) and the solution was added to diphenyldiazomethane (0.02 mole) acetone solution at RT. The reaction solution was stirred for 12 hours at RT, concentrated and crystallized with n-hexane to give 11.0 g (100%) of (2R)-3-methyl-2-[(2-n-hexylthiobenzthiazol-6-sulfonyl)amino]butanoic acid diphenylmethylester. (2R)-3-Methyl-2-[(2-n-hexylthiobenzthiazol-6-sulfonyl)amino] butanoic acid diphenylmethylester (1.0 g, 1.7 mmol) was dissolved in acetone (3 mL). $K_2CO_3$ (0.47 g, 2.0 equi.) and ethylbromoacetate (0.204 mL, 1.1 equi.) were added to the solution and then, the reaction solution was reacted at 50° C. for 12 hours. Then, the reaction solution was distilled under reduced pressure to remove the solvent and the product was extracted with water/ethylacetate. The organic phase was treated with anhydrous $MgSO_4$ to remove the solvent and give (2R)-3-methyl-2-[(2-n-hexylthiobenzthiazol-6-sulfonyl) ethoxycarbonylmethyl amino]butanoic acid diphenylmethylester (1.14 g, 100%). Without further purification, the compound was dissolved in $CH_2Cl_2$ (50 mL). Then, TFA (1.29 mL, 10.0 eq) and anisole (0.55 mL, 3 eq) were added and the reaction solution was subjected at PT for 2 hours. Then, the solvent was removed from the solution, which was then treated with n-hexane to give (2R)-3-methyl-2-[(2-n-hexylthiobenzthiazol-6-sulfonyl) ethoxycarbonylmethyl amino]butanoic acid (1.0 g). The product was dissolved in dichloromethane (25 ml) and the solution was cooled down to 0° C. Oxalylchloride (0.73 mL, 5 equi.) and DMF of catalytic amount were added, and reacted for 3 hours at RT. Then, the reaction solution was distilled under reduced pressure to remove solvent and dried under reduced pressure to give (2R)-3-methyl-2-[(2-n-hexylthiobenzthiazol-6-sulfonyl) ethoxycarbonylmethyl amino]butanoic acid chloride which was then dissolved in THF (20 mL). Hydroxylamine hydrochloride (1.16 g, 10 equi.) and $NaHCO_3$ (2.83 g, 12 equi.) were dissolved in $THF/H_2O$ (20 mL/20 mL) and cooled down to 0° C. to prepare hydroxylamine solution. The acid chloride/THF solution thus obtained was slowly added to the hydroxylamine solution. After 1 hour, the solvent was removed from the reaction solution. The product was extracted with ethylacetate (50 mL) and then, washed with $H_2O$ and 0.1N HCl and dried over $MgSO_4$ to prepare 1.23 g of N-hydroxy-(2R)-3-methyl-2-[(2-n-hexylthiobenzthiazol-6-sulfonyl)ethoxycarbonyl methylamino]butyric amide.

$^1$H NMR (300 MHz, MeOH-$d_4$): δ 0.84 (d, 3H), 0.93 (d, 3H), 1.37 (m, 6H), 1.52 (m, 6H), 1.86 (m, 2H), 2.1 (m, 1H), 3.3 (t, 2H), 4.3 (m, 5H), 2.09 (m, 2H), 2.6 (dd, 1H), 2.9 (dd, 1H), 3.87(s, 3H), 6.65 (bs, 1H), 7.97 (m, 2H), 8.37 (m, 1H), 9.33 (bs, 1H)

EXAMPLE 70

In vitro Inhibition on Gelatinase A (MMP-2)

The present test was accomplished by measuring the fluorescence intensity of a fluorescent material (7-methoxycoumarin-4-acetyl-Pro—Leu—Gly) produced from the cleavage of a fluorescent synthetic peptide substrate ((7-methoxycoumarin-4-acetyl-Pro—Leu—Gly—Leu-β-(2,4-dinitrophenylamino) Ala—Ala—Arg—$NH_2$ (Sigma Chem. Co. U.S.A.)) by gelatinase A (Boehringer Manneheim cat# 1782916, from human fibrosarcoma cells).

Enzymatic reaction employing a fluorescent synthetic substrate was accomplished by putting test compounds, TNBC buffer solution (25 mM Tris-HCl, pH 7.5, 0.1M NaCl, 0.01% Brij-35, 5 mM $CaCl_2$), gelatinase A (final concentration in well: 4.17 nM) activated with 1 mM of APMA (aminophenylmercuric acetate) for 30 minutes at 37° C. just before the enzymatic reaction and the substrate, fluorescent synthetic peptide (final concentration in well: 9.15 uM) in 96 well plate and then reacting for 30 minutes at 37° C., and the fluorescence intensity was measured at excitation 328 nm and emission 393 nm by spectrofluorimeter (Fmax(molecular device)). The inhibition rate (%) was calculated from the following equation:

$$\text{Inhibition Rate}(\%) = \frac{(D-C)-(B-A)}{(D-C)} \times 100$$

wherein,

A represents fluorescence intensity before the reaction with an inhibitor;

B represents fluorescence intensity after the reaction with an inhibitor;

C represents fluorescence intensity before the reaction without an inhibitor; and, D represents fluorescence intensity after the reaction without an inhibitor.

EXAMPLE 71

In vitro Inhibition on Gelatinase B (MMP-9)

In vitro inhibition rate on gelatinase B (MMP-9) was measured in a similar manner as in Example 70, except for employing gelatinase B (Boehringer Manneheim cat# 1758896, from human blood) and the concentration of gelatinase B (final concentration in well: 2.715 nM) and the concentration of the substrate, fluorescent synthetic peptide (final concentration in well: 4.575 uM).

EXAMPLE 72

In vitro Inhibition on Collagenase (MMP-1)

In vitro inhibition rate on collagenase (MMP-1) was measured in a similar manner as in Example 70, except for employing collagenase (AngioLab. Co., Ltd) and the concentration of the collagenase (final concentration in well: 7.25 nM).

TABLE 1

| Number | $R_1$ | $R_2$ | $R_4$ | $R_3$ | $IC_{50}$ (nM) MMP-2 | $IC_{50}$ (nM) MMP-9 | $IC_{50}$ (nM) MMP-1 |
|---|---|---|---|---|---|---|---|
| 1 | n-$C_5H_{11}$ | $CH_3$ | H | $CO_2H$ | 38.9 | 180.0 | |
| 2 | n-$C_5H_{11}$ | $CH_3$ | H | CONHOH | 0.3 | 1.0 | 1600 |
| 3 | n-$C_6H_{13}$ | $CH_3$ | H | $CO_2H$ | 100.0 | 1520.0 | |
| 4 | n-$C_6H_{13}$ | $CH_3$ | H | CONHOH | 0.5 | 3.0 | |
| 5 | n-$C_5H_{11}$ | $CH_3$ | Bn | $CO_2H$ | 63.5 | 130.0 | |
| 6 | n-$C_5H_{11}$ | $CH_3$ | Bn | CONHOH | 1.4 | 1.0 | |
| 7 | c-Hexyl-$CH_2$ | $CH_3$ | H | $CO_2H$ | 14.7 | 190.0 | |
| 8 | c-Hexyl-$CH_2$ | $CH_3$ | H | CONHOH | 0.5 | 3.0 | |
| 9 | c-Hexyl-$CH_2$ | $CH_3$ | Bn | $CO_2H$ | 23.6 | 110.0 | |
| 10 | c-Hexyl-$CH_2$ | $CH_3$ | Bn | CONHOH | 1.2 | 2.0 | |
| 11 | n-$C_5H_{11}$ | $PhCH_2$ | H | CONHOH | 0.4 | 1.5 | 13896 |
| 12 | n-$C_5H_{11}$ | $PhCH_2$ | Bn | CONHOH | 2.3 | 2.6 | |
| 13 | n-$C6H_{13}$ | $PhCH_2$ | H | CONHOH | 1.2 | 8.0 | 25640 |
| 14 | c-Hexyl-$CH_2$ | $PhCH_2$ | H | CONHOH | 1.2 | 9.0 | |
| 15 | c-Hexyl-$CH_2$ | $PhCH_2$ | Bn | CONHOH | 9.1 | 22.0 | |
| 16 | n-$C_5H_{11}$ | $CH_3SCH_2CH_2$ | H | CONHOH | 0.3 | 0.6 | 3013 |
| 17 | n-$C_6H_{13}$ | $CH_3SCH_2CH_2$ | H | CONHOH | 0.8 | 3.0 | |
| 18 | n-$C_5H_{11}$ | $CH_3SCH_2CH_2$ | Bn | CONHOH | 4.3 | 3.8 | |
| 19 | c-Hexyl-$CH_2$ | $CH_3SCH_2CH_2$ | H | CONHOH | 0.6 | 3.0 | |
| 20 | n-$C_5H_{11}$ | $HO_2CCH_2CH_2$ | H | $CO_2H$ | 47.0 | 610.0 | |
| 21 | n-$C_6H_{13}$ | $HO_2CCH_2CH_2$ | H | $CO_2H$ | 76.2 | 800.0 | 330400 |
| 22 | n-$C_6H_{13}$ | $HO_2CCH_2$ | H | $CO_2H$ | 95.0 | 420.0 | 311430 |
| 23 | n-$C_5H_{11}$ | Iso-Butyl | H | CONHOH | 0.2 | 0.4 | 3380 |
| 24 | n-$C_6H_{13}$ | Iso-Butyl | H | CONHOH | 0.4 | 2.0 | 7070 |
| 25 | n-$C_5H_{11}$ | 2-Indole$CH_2$ | H | $CO_2H$ | 6.4 | 20.0 | 11909 |
| 26 | n-$C_6H_{13}$ | 2-Indole$CH_2$ | H | $CO_2H$ | 9.1 | 20.0 | |
| 27 | n-$C_5H_{11}$ | 2-Indole$CH_2$ | H | CONHOH | 1.5 | 2.7 | |
| 28 | n-$C_6H_{13}$ | 2-Indole$CH_2$ | H | CONHOH | 3.0 | 6.0 | |
| 29 | $CH_3$ | Iso-Propyl | H | $CO_2H$ | 640.0 | 4800.0 | |
| 30 | $CH_3$ | Iso-Propyl | H | CONHOH | 5.0 | 34.0 | |
| 31 | $C_2H_5$ | Iso-Propyl | H | $CO_2H$ | 210.0 | 7400.0 | |
| 32 | $C_2H_5$ | Iso-Propyl | H | CONHOH | 1.3 | 16.0 | |
| 33 | $C_2H_5$ | Iso-Propyl | Bn | $CO_2H$ | 1200.0 | 6280.0 | |
| 34 | $C_2H_5$ | Iso-Propyl | Bn | CONHOH | 6.0 | 20.4 | |
| 35 | n-$C_3H_7$ | Iso-Propyl | H | $CO_2H$ | 150.0 | 4100.0 | |
| 36 | n-$C_3H_7$ | Iso-Propyl | H | CONHOH | 0.2 | 4.0 | |
| 37 | n-$C_3H_7$ | Iso-Propyl | Bn | $CO_2H$ | 900.0 | 3180.0 | |
| 38 | n-$C_3H_7$ | Iso-Propyl | Bn | CONHOH | 2.5 | 5.0 | |
| 39 | n-$C_4H_9$ | Iso-Propyl | H | $CO_2H$ | 1.6 | 144.0 | 3819 |
| 40 | n-$C_4H_9$ | Iso-Propyl | H | CONHOH | 0.3 | 0.2 | |
| 41 | n-$C_4H_9$ | Iso-Propyl | Bn | $CO_2H$ | 270.0 | 700.0 | |
| 42 | n-$C_4H_9$ | Iso-Propyl | Bn | CONHOH | 2.7 | 3.0 | |
| 43 | n-$C_5H_{11}$ | Iso-Propyl | H | $CO_2H$ | 16.0 | 189.0 | |
| 44 | n-$C_5H_{11}$ | Iso-Propyl | H | CONHOH | 0.2 | 0.5 | 2606 |
| 45 | n-$C_5H_{11}$ | Iso-Propyl | Bn | $CO_2H$ | 400.0 | 660.0 | |
| 46 | n-$C_5H_{11}$ | Iso-Propyl | Bn | CONHOH | 3.8 | 3.5 | |
| 47 | n-$C_6H_{13}$ | Iso-Propyl | H | $CO_2H$ | 15.0 | 178.0 | 172380 |
| 48 | n-$C_6H_{13}$ | Iso-Propyl | H | CONHOH | 0.6 | 3.1 | 2780 |
| 49 | n-$C_6H_{13}$ | Iso-Propyl | Bn | $CO_2H$ | 385.0 | 1767.0 | |
| 50 | n-$C_6H_{13}$ | Iso-Propyl | Bn | CONHOH | 3.0 | 4.9 | |
| 51 | n-$C_7H_{15}$ | Iso-Propyl | H | $CO_2H$ | 5.0 | 496.0 | 12504 |
| 52 | n-$C_7H_{15}$ | Iso-Propyl | H | CONHOH | 0.3 | 2.0 | 6303 |
| 53 | n-$C_7H_{15}$ | Iso-Propyl | Bn | $CO_2H$ | | | |
| 54 | n-$C_7H_{15}$ | Iso-Propyl | Bn | CONHOH | | | |
| 55 | n-$C_8H_{17}$ | Iso-Propyl | H | $CO_2H$ | 9.0 | 764.0 | |
| 56 | n-$C_8H_{17}$ | Iso-Propyl | H | CONHOH | 0.5 | 3.0 | |
| 57 | n-$C_8H_{17}$ | Iso-Propyl | Bn | $CO_2H$ | 780.0 | 5120.0 | |
| 58 | n-$C_8H_{17}$ | Iso-Propyl | Bn | CONHOH | 28.0 | 77.0 | |
| 59 | n-$C_{12}H_{25}$ | Iso-Propyl | H | $CO_2H$ | 170.0 | 4210.0 | |
| 60 | n-$C_{12}H_{25}$ | Iso-Propyl | H | CONHOH | 17.0 | 77.0 | |
| 61 | n-$C_{12}H_{25}$ | Iso-Propyl | Bn | $CO_2H$ | 23400.0 | 59600.0 | |

TABLE 1-continued

| Number | $R_1$ | $R_2$ | $R_4$ | $R_3$ | $IC_{50}$ (nM) MMP-2 | $IC_{50}$ (nM) MMP-9 | $IC_{50}$ (nM) MMP-1 |
|---|---|---|---|---|---|---|---|
| 62 | n-$C_{12}H_{25}$ | Iso-Propyl | Bn | CONHOH | 0.7 | 27.0 | |
| 63 | c-HexylCH$_2$ | Iso-Propyl | H | CO$_2$H | 9.3 | 202.0 | |
| 64 | c-HexylCH$_2$ | Iso-Propyl | H | CONHOH | 0.046 | 0.24 | 4671 |
| 65 | c-HexylCH$_2$CH$_2$CH$_2$ | Iso-Propyl | H | CO$_2$H | 8.0 | 0.7 | |
| 66 | c-HexylCH$_2$CH$_2$CH$_2$ | Iso-Propyl | H | CONHOH | 0.7 | 5.8 | |
| 67 | c-Pentyl | Iso-Propyl | H | CO$_2$H | 690.0 | 8250.0 | |
| 68 | c-Pentyl | Iso-Propyl | H | CONHOH | 1.4 | 5.0 | |
| 69 | PhCH$_2$ | Iso-Propyl | H | CO$_2$H | 90.0 | 99.0 | |
| 70 | PhCH$_2$ | Iso-Propyl | H | CONHOH | 0.7 | 0.7 | |
| 71 | p-ClPhCH$_2$ | Iso-Propyl | H | CO$_2$H | 40.0 | 79.0 | |
| 72 | p-ClPhCH$_2$ | Iso-Propyl | H | CONHOH | 0.2 | 0.6 | 2331 |
| 73 | p-MeOPhCH$_2$ | Iso-Propyl | H | CO$_2$H | 36.0 | 420.0 | |
| 74 | p-MeOPhCH$_2$ | Iso-Propyl | H | CONHOH | 0.8 | 0.2 | |
| 75 | PhCH$_2$CH$_2$CH$_2$ | Iso-Propyl | H | CO$_2$H | 1120.0 | 3190.0 | |
| 76 | PhCH$_2$CH$_2$CH$_2$ | Iso-Propyl | H | CONHOH | 10.7 | 34.0 | |
| 77 | Ph | Iso-Propyl | H | CO$_2$H | 410.0 | 1880.0 | |
| 78 | Ph | Iso-Propyl | H | CONHOH | 0.6 | 2.3 | |
| 79 | p-Me-Ph | Iso-Propyl | H | CO$_2$H | 250.0 | 1710.0 | |
| 80 | p-Me-Ph | Iso-Propyl | H | CONHOH | 0.74 | 2.0 | |
| 81 | p-Br-Ph | Iso-Propyl | H | CO$_2$H | 320.0 | 930.0 | |
| 82 | p-Br-Ph | Iso-Propyl | H | CONHOH | 5.3 | 28.0 | |
| 83 | p-F-Ph | Iso-Propyl | H | CO$_2$H | 1430.0 | 451.0 | |
| 84 | p-F-Ph | Iso-Propyl | H | CONHOH | 8.7 | 23.0 | |
| 85 | p-MeO-Ph | Iso-Propyl | H | CO$_2$H | 290.0 | 740.0 | |
| 86 | p-MeO-Ph | Iso-Propyl | H | CONHOH | 0.2 | 0.2 | 13432 |
| 87 | p-n-Bu-Ph | Iso-Propyl | H | CO$_2$H | 120.0 | 660.0 | |
| 88 | p-n-Bu-Ph | Iso-Propyl | H | CONHOH | 0.6 | 2.0 | |
| 89 | n-$C_4H_9$ | PhCH$_2$ | H | PO$_3$H$_2$ | 52200.0 | 4491610 | |
| 90 | n-$C_4H_{13}$ | PhCH$_2$ | H | PO$_3$H$_2$ | 40140.0 | 289770 | |
| 91 | c-HexylCH$_2$ | PhCH$_2$ | H | PO$_3$H$_2$ | 20560.0 | 537500 | |

TABLE 2

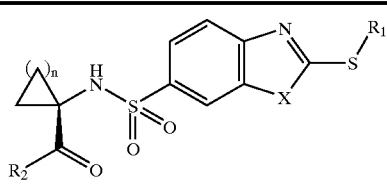

| Number | $R_1$ | $R_2$ | X | N | $IC_{50}$(nM) MMP-2 | $IC_{50}$(nM) MMP-9 |
|---|---|---|---|---|---|---|
| 1 | n-$C_4H_9$ | OH | S | 1 | 1219 | 7535 |
| 2 | n-$C_4H_9$ | NHOH | S | 1 | 18.4 | 26.6 |
| 3 | n-$C_4H_9$ | OH | S | 3 | 651 | 3922 |
| 4 | n-$C_4H_9$ | NHOH | S | 3 | 7.0 | 20.0 |
| 5 | n-$C_4H_9$ | OH | S | 4 | 246 | 1364 |
| 6 | n-$C_4H_9$ | NHOH | S | 4 | 5.9 | 14.2 |

TABLE 3

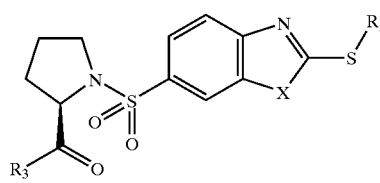

| Number | $R_1$ | $R_3$ | X | $IC_{50}$(nM) MMP-2 | $IC_{50}$(nM) MMP-9 |
|---|---|---|---|---|---|
| 1 | n-$C_5H_{11}$ | OH | S | 1210 | 8050 |
| 2 | n-$C_5H_{11}$ | NHOH | S | 5.8 | 4.2 |

TABLE 3-continued

| Number | $R_1$ | $R_3$ | X | $IC_{50}$(nM) MMP-2 | $IC_{50}$(nM) MMP-9 |
|---|---|---|---|---|---|
| 3 | n-$C_6H_{13}$ | OH | S | 944 | 14100 |
| 4 | n-$C_6H_{13}$ | NHOH | S | 5.6 | 1 |

TABLE 4

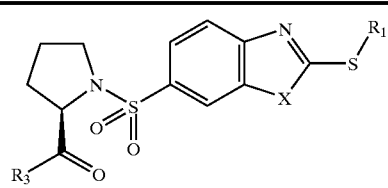

| Number | $R_1$ | $R_2$ | $R_3$ | X | $IC_{50}$(nM) MMP-2 | $IC_{50}$(nM) MMP-9 |
|---|---|---|---|---|---|---|
| 1 | n-$C_5H_{11}$ | H | OH | S | 380 | 1290 |
| 2 | n-$C_5H_{11}$ | H | NHOH | S | 0.4 | 0.6 |
| 3 | n-$C_5H_{11}$ | CH3 | OH | S | 37460 | 207257 |
| 4 | n-$C_5H_{11}$ | CH3 | NHOH | S | 1000 | 2052 |

TABLE 5

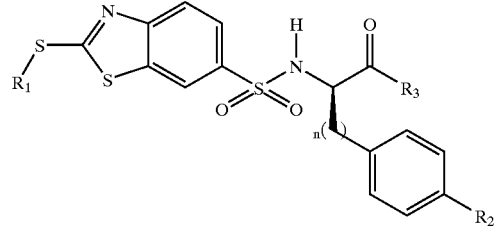

| Number | R$_1$ | R$_2$ | R$_3$ | N | IC$_{50}$(nM) MMP-2 | IC$_{50}$(nM) MMP-9 | IC$_{50}$(μM) MMP-1 |
|---|---|---|---|---|---|---|---|
| 1 | (±) n-C$_7$H$_{15}$ | H | OH | 2 | 119 | 1550 | |
| 2 | (±) n-C$_7$H$_{15}$ | H | NHOH | 2 | 3.4 | 39 | |
| 3 | (±) n-C$_7$H$_{15}$ | H | OH | 3 | 69 | 742 | |
| 4 | (±) n-C$_7$H$_{15}$ | H | NHOH | 3 | 1.63 | 6 | |
| 5 | (±) n-C$_7$H$_{15}$ | HCCCH$_2$—O— | OH | 1 | 81 | 84 | |
| 6 | (±) n-C$_7$H$_{15}$ | HCCCH$_2$—O— | NHOH | 1 | 3.63 | 2.74 | |
| 7 | (R) n-C$_7$H$_{15}$ | HCCCH$_2$—O— | OH | 1 | 56 | 3072 | |
| 8 | (R) n-C$_7$H$_{15}$ | HCCCH$_2$—O— | NHOH | 1 | 1.6 | 9.8 | |
| 9 | (R) n-C$_7$H$_{15}$ | HCCHCH$_2$—O— | OH | 1 | 137 | 7915 | |
| 10 | (R) n-C$_7$H$_{15}$ | HCCHCH$_2$—O— | NHOH | 1 | 1.2 | 8 | |
| 11 | (R) n-C$_7$H$_{15}$ | PhCH$_2$CH$_2$CH$_2$—O— | OH | 1 | 704 | 28770 | |
| 12 | (R) n-C$_7$H$_{15}$ | PhCH$_2$—O— | NHOH | 1 | 6 | 87 | |
| 13 | (R) n-C$_7$H$_{15}$ | PhCH$_2$—O— | OH | 1 | 684 | 1430 | |
| 14 | (R) n-C$_7$H$_{15}$ | PhCH$_2$CH$_2$—O— | NHOH | 1 | 23 | 134 | |
| 15 | (R) n-C$_7$H$_{15}$ | PhCH$_2$CH$_2$—O— | OH | 1 | 508 | 2330 | |
| 16 | (R) n-C$_7$H$_{15}$ | PhCH$_2$CH$_2$CH$_2$—O— | NHOH | 1 | 2 | 22 | |
| 17 | (R) n-C$_7$H$_{15}$ | Phthalimino-(CH$_2$)$_3$—O— | OH | 1 | 40 | 476 | |
| 18 | (R) n-C$_7$H$_{15}$ | Phthalimino-(CH$_2$)$_3$—O— | NHOH | 1 | 0.8 | 8 | |
| 19 | (R) n-C$_5$H$_{11}$ | PhCH$_2$CH$_2$CH$_2$—O— | OH | 1 | 340 | 915 | |
| 20 | (R) n-C$_5$H$_{11}$ | PhCH$_2$CH$_2$CH$_2$—O— | NHOH | 1 | 4.9 | 9.1 | |
| 21 | (R) n-C$_5$H$_{11}$ | Phthalimino-(CH$_2$)$_3$—O— | OH | 1 | 40 | 129 | |
| 22 | (R) n-C$_5$H$_{11}$ | Phthalimino-(CH$_2$)$_3$—O— | NHOH | 1 | 0.9 | 1.9 | |
| 23 | (R) n-C$_6$H$_{13}$ | HCCHCH$_2$—O— | OH | 1 | 101 | 536 | 1144.4 |
| 24 | (R) n-C$_6$H$_{13}$ | HCCHCH$_2$—O— | NHOH | 1 | 1.5 | 5 | 27.6 |
| 25 | (R) n-C$_6$H$_{13}$ | HCCCH$_2$—O— | OH | 1 | 62 | 462 | |
| 26 | (R) n-C$_6$H$_{13}$ | HCCCH$_2$—O— | NHOH | 1 | 6.4 | 9 | 45.8 |
| 27 | (R) n-C$_6$H$_{13}$ | PhCH$_2$CH$_2$CH$_2$—O— | OH | 1 | 251 | 1495 | |
| 28 | (R) n-C$_6$H$_{13}$ | PhCH$_2$CH$_2$CH$_2$—O— | NHOH | 1 | 7.6 | 30 | 139.7 |
| 29 | (R) n-C$_6$H$_{13}$ | Phthalimino-(CH$_2$)$_3$—O— | OH | 1 | 40 | 223 | |
| 30 | (R) n-C$_6$H$_{13}$ | Phthalimino-(CH$_2$)$_3$—O— | NHOH | 1 | 1.6 | 1.1 | 10.2 |
| 31 | (R) p-C$_1$PhCH$_2$ | Phthalimino-(CH$_2$)$_3$—O— | OH | 1 | 193 | 332 | |
| 32 | (R) p-C$_1$PhCH$_2$ | Phthalimino-(CH$_2$)$_3$—O— | NHOH | 1 | 4.5 | 5.8 | |
| 33 | (R) p-MeO—Ph | Phthalimino-(CH$_2$)$_3$—O— | OH | 1 | 1057 | 5148 | |
| 34 | (R) p-MeO—Ph | Phthalimino-(CH$_2$)$_3$—O— | NHOH | 1 | 3.2 | 7 | |
| 35 | (R) c-Pentyl | Phthalimino-(CH$_2$)$_3$—O— | OH | 1 | 1144 | 7956 | |
| 36 | (R) c-Pentyl | Phthalimino-(CH$_2$)$_3$—O— | NHOH | 1 | 4.7 | 23.5 | |

TABLE 6

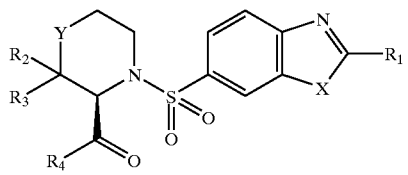

| Number | R$_1$ | R$_2$:R$_3$ | R$_4$ | Y | IC$_{50}$(nM) MMP-2 | IC$_{50}$(nM) MMP-9 | IC$_{50}$(nM) MMP-1 |
|---|---|---|---|---|---|---|---|
| 1 | n-C$_4$H$_9$—S— | CH$_3$:CH$_3$ | OH | S | 483 | 1474 | |
| 2 | n-C$_4$H$_9$—S— | CH$_3$:CH$_3$ | NHOH | S | 0.4 | 0.4 | |
| 3 | n-C$_6$H$_{13}$—S— | CH$_3$:CH$_3$ | OH | S | 172 | 795 | |
| 4 | n-C$_6$H$_{13}$—S— | CH$_3$:CH$_3$ | NHOH | S | 0.3 | 0.4 | 150 |
| 5 | c-HexylCH$_2$—S— | CH$_3$:CH$_3$ | OH | S | 46 | 232 | |
| 6 | c-HexylCH$_2$—S— | CH$_3$:CH$_3$ | NHOH | S | 0.7 | 1 | |
| 7 | MeO— | H:H | OH | CH$_2$ | 16100 | 13400 | |
| 8 | C$_2$H$_5$—S— | H:H | OH | CH$_2$ | 1560 | 3030 | |
| 9 | C$_2$H$_5$—S— | H:H | NHOH | CH$_2$ | 2.0 | 9.0 | |
| 10 | n-C$_4$H$_9$—S— | H:H | OH | CH$_2$ | 120 | 1820 | |

TABLE 6-continued

| Number | $R_1$ | $R_2$:$R_3$ | $R_4$ | Y | IC$_{50}$(nM) MMP-2 | IC$_{50}$(nM) MMP-9 | IC$_{50}$(nM) MMP-1 |
|---|---|---|---|---|---|---|---|
| 11 | n-$C_4H_9$—S— | H:H | NHOH | $CH_2$ | 1.3 | 0.7 | |
| 12 | n-$C_6H_{13}$—S— | H:H | OH | $CH_2$ | 86 | 2270 | |
| 13 | n-$C_6H_{13}$—S— | H:H | NHOH | $CH_2$ | 1.8 | 2.8 | |
| 14 | n-$C_7H_{15}$—S— | H:H | OH | $CH_2$ | 49 | 2250 | |
| 15 | n-$C_7H_{15}$—S— | H:H | NHOH | $CH_2$ | 1.7 | 8.9 | |
| 16 | n-$C_8H_{17}$—S— | H:H | OH | $CH_2$ | 53 | 1950 | |
| 17 | n-$C_8H_{17}$—S— | H:H | NHOH | $CH_2$ | 3.6 | 21.8 | |
| 18 | c-HexylCH$_2$—S— | H:H | OH | $CH_2$ | 31 | 680 | |
| 19 | c-HexylCH$_2$—S— | H:H | NHOH | $CH_2$ | 0.5 | 1.9 | |

TABLE 7

| Number | $R_1$ | X | $R_3$ | n | $R_4$ | IC$_{50}$(nM) MMP-2 | IC$_{50}$(nM) MMP-9 |
|---|---|---|---|---|---|---|---|
| 1 | Methyl | S | N-Morpholino | 1 | NHOH | 8.8 | 17.2 |
| 2 | Methyl | S | N-Morpholino | 1 | OH | 1846 | 9790 |
| 3 | n-Hexyl | O | —CO$_2$Et | 2 | NHOH | 19.1 | 1.5 |
| 4 | n-Hexyl | O | —CO$_2$Et | 2 | OH | 1800 | 1118 |
| 5 | n-Hexyl | O | N-Morpholino | 1 | NHOH | 14.0 | 4.4 |
| 6 | n-Hexyl | O | 3-Pyridyl | 0 | NHOH | 6.3 | 1.9 |
| 7 | c-Hexylmethyl | S | Hydroxyimino- | 1 | OH | 16.2 | 83.5 |
| 8 | n-Hexyl | O | Phenyl | 0 | NHOH | | 11.4 |
| 9 | Methyl | S | OH | 2 | NHOH | 7.4 | 13.1 |
| 10 | Methyl | S | AcO- | 2 | NHOH | 4.8 | 6.7 |
| 11 | c-Hexylmethyl | S | 1,3-dioxlane-2- | 1 | OH | 19.9 | 93.0 |
| 12 | n-Propyl | S | AcO- | 2 | NHOH | 1.6 | 2.0 |
| 13 | n-Propyl | S | OH | 2 | NHOH | 1.5 | 2.2 |
| 14 | n-Hexyl | S | AcO- | 2 | NHOH | 0.9 | 0.7 |
| 15 | n-Hexyl | S | OH | 2 | NHOH | 0.4 | 0.4 |
| 16 | c-Hexylmethyl | S | Phthalimido-1- | 2 | NHOH | 7.4 | 11.6 |
| 17 | c-Hexylmethyl | S | Succinimido-1- | 2 | NHOH | 1.8 | 2.7 |
| 18 | n-Propyl | S | —CO$_2$H | 2 | NHOH | 2.0 | 2.2 |
| 19 | n-Propyl | S | —CO$_2$Et | 2 | NHOH | 1.4 | 1.7 |
| 20 | Methyl | S | —CO$_2$H | 2 | NHOH | 6.7 | 9.3 |
| 21 | Methyl | S | —CO$_2$Et | 2 | NHOH | 2.7 | 3.3 |
| 22 | c-Hexylmethyl | S | —CO$_2$H | 3 | NHOH | 0.9 | 1.3 |
| 23 | c-Hexylmethyl | S | —CO$_2$Et | 3 | NHOH | 3.2 | 3.8 |
| 24 | c-Hexylmethyl | S | OH | 2 | NHOH | 0.6 | 1.0 |
| 25 | c-Hexylmethyl | S | AcO- | 2 | NHOH | 1.6 | 2.2 |
| 26 | n-Hexyl | S | 4-CO$_2$H—Ph— | 0 | NHOH | 0.5 | 0.2 |
| 27 | n-Hexyl | S | —CO$_2$H | 4 | NHOH | 0.2 | 0.2 |
| 28 | n-Hexyl | S | 4-MeCO$_2$—Ph— | 0 | NHOH | 20.0 | 15.3 |
| 29 | n-Hexyl | S | —CO$_2$Et | 4 | NHOH | 4.4 | 1.2 |
| 30 | c-Hexylmethyl | S | N-Morpholino | 1 | NHOH | 1.2 | 1.8 |
| 31 | c-Hexylmethyl | S | 3-Pyridyl | 1 | NHOH | 2.0 | 2.7 |
| 32 | c-Hexylmethyl | S | —CO$_2$Et | 0 | NHOH | 4.2 | 15.1 |
| 33 | n-Hexyl | S | N-Morpholino | 1 | NHOH | 0.7 | 0.4 |
| 34 | n-Hexyl | S | 3-Pyridyl | 0 | NHOH | 1.3 | 0.9 |
| 35 | n-Hexyl | S | —CO$_2$-t-Bu | 0 | NHOH | 3.2 | 1.6 |
| 36 | n-Hexyl | S | —CO$_2$Et | 2 | NHOH | 1.3 | 0.5 |

TABLE 7-continued

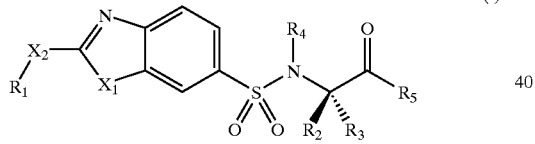

| Number | $R_1$ | X | $R_3$ | n | $R_4$ | $IC_{50}$(nM) MMP-2 | $IC_{50}$(nM) MMP-9 |
|---|---|---|---|---|---|---|---|
| 37 | n-Hexyl | S | —$CO_2$Et | 0 | NHOH | 2.1 | 1.5 |
| 38 | n-Hexyl | S | —$CO_2$H | 2 | NHOH | 0.4 | 0.2 |

As clearly illustrated and demonstrated as aboves, the present invention provides novel sulfonamide derivatives, which inhibit MMP activity, their isomers and the pharmaceutically acceptable salts thereof, and a process for preparing the compounds. Since the sulfonamide derivatives of the present invention selectively inhibit MMP activity in vitro, the MMP inhibitors comprising the sulfonamide derivatives as an active ingredient can be practically applied for the prevention and treatment of diseases caused by overexpression and overactivation of MMP.

Although the preferred embodiments of the present invention have been disclosed for illustrative purpose, those who are skilled in the art will appreciate that various modifications, additions and substitutions are possible, without departing from the scope and spirit of the invention as described in the accompanying claims.

What is claimed is:

1. A compound represented as the following general formula(I), and its isomers and pharmaceutically acceptable salts thereof:

(I)

wherein $R_1$ denotes hydrogen, $C_{1-12}$ alkyl, carbocyclic aryl-lower alkyl, $C_{3-7}$ cycloalkyl, $C_{3-7}$ cycloalkyl-lower alkyl, oxo $C_{3-7}$ cycloalkyl, amino $C_{3-7}$ cycloalkyl, thio $C_{3-7}$ cycloalkyl, oxo $C_{3-7}$ cycloalkyl-lower alkyl, amino $C_{3-7}$ cycloalkyl-lower alkyl, thio $C_{3-7}$ cycloalkyl-lower alkyl, $C_{2-12}$ lower alkenyl, $C_{2-12}$ lower alkynyl, carbocyclic aryl, heterocyclic aryl, heterocyclic aryl-lower alkyl, biaryl, halo lower alkyl, biaryl-lower alkylarylalkyl, hydroxy-lower alkyl, alkoxyloweralkyl, acyloxy-lower alkyl, alkyl thio lower alkyl, alkyl sulfinyl lower alkyl, alkyl sulfonyl lower alkyl, aryl thio lower alkyl, aryl sulfinyl lower alkyl, aryl sulfonyl lower alkyl, amino lower alkyl, mono lower alkyl amino lower alkyl, dialkylamino lower alkyl, acylamino lower alkyl, N-lower alkyl-piperazino-lower alkyl, N-(carbocyclic aryl-lower alkyl) piperazino-lower alkyl, heterocyclic aryl-lower alkyl piperazino-lower alkyl, morpholino-lower alkyl, thiomorpholino-lower alkyl, piperidino-lower alkyl, pyrrolidino-lower alkyl or piperidyl-lower alkyl;

$R_2$ denotes hydrogen, lower alkyl, carbocyclic aryl-lower alkyl, $C_{1-4}$ carbocyclic aryl-lower alkyl, $C_{1-4}$ heterocyclic aryl-lower alkyl, $C_{1-5}$ alkoxyphenyl-lower alkyl, $C_{1-5}$ alkenoxyphenyl-lower alkyl, $C_{1-5}$ alkynoxyphenyl-lower alkyl, heterocyclic aryl-lower alkyl, hydroxy-lower alkyl, alkoxyloweralkyl, acyloxy-lower alkyl, thio-lower alkyl, alkyl-thio lower alkyl, alkyl-sulfinyl lower alkyl, alkyl-sulfonyl lower alkyl, aryl-thio lower alkyl, aryl-sulfinyl lower alkyl, aryl-sulfonyl lower alkyl, amino lower alkyl, mono lower alkyl amino lower alkyl, dialkylamino lower alkyl, carboxyl-lower alkyl or acylamino lower alkyl;

$R_3$ denotes hydrogen or $C_{1-6}$ lower alkyl;

$R_4$ denotes hydrogen, $C_{1-12}$ alkyl, $C_{3-7}$ cycloalkyl, $C_{3-7}$ cycloalkyl-lower alkyl, oxo $C_{3-7}$ cycloalkyl, amino $C_{3-7}$ cycloalkyl, thio $C_{3-3}$ cycloalkyl, oxo $C_{3-4}$ cycloalkyl-lower alkyl, amino $C_{3-7}$ cycloalkyl-lower alkyl, thio $C_{3-7}$ cycloalkyl-lower alkyl, carbocyclic aryl, carbocyclic aryl-lower alkyl, heterocyclic aryl, heterocyclic aryl-lower alkyl, biaryl, biaryl-lower alkyl, halo lower alkyl, hydroxy-lower alkyl, alkoxyloweralkyl, acyloxy-lower alkyl, alkyl-thio lower alkyl, alkyl-sulfinyl lower alkyl, alkyl-sulfonyl lower alkyl, aryl-thio lower alkyl, aryl-sulfinyl lower alkyl, aryl-sulfonyl lower alkyl, amino lower alkyl, mono lower alkyl amino lower alkyl, dialkylamino lower alkyl, acylamino lower alkyl, carboxyl lower alkyl, N-lower alkyl-piperazino-lower alkyl, N-carbocyclic aryl piperazino-lower alkyl, heterocyclic aryl piperazino-lower alkyl, morpholino-lower alkyl, thiomorpholino-lower alkyl, piperidino-lower alkyl, pyrrolidino-lower alkyl, or piperidyl-lower alkyl;

$R_5$ denotes hydroxyl, alkoxyl, halogen, thiol, thioalkoxyl or hydroxylamine; and, or $X_1$ and $X_2$ denote S, O of N—$R_7$, wherein $R_7$ is hydrogen, $C_{1-6}$-lower alkyl, aryl, heteroaryl or arylalkyl wherein $R_2$ can form a ring together with either $R_3$ or $R_4$.

2. The compound of claim 1, wherein $R_2$ and $R_3$ are linked together to form a $C_{3-6}$ carbocyclic or heterocyclic ring represented as the following general formula(I-1):

(I-1)

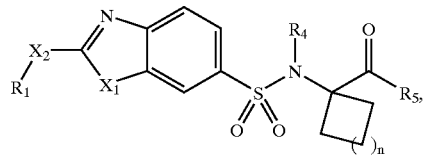

wherein n is an integer of 0 to 4.

3. The compound of claim 1, wherein $R_2$ and $R_4$ are linked together to form a heterocyclic ring represented as the following general formula(I-2):

(I-2)

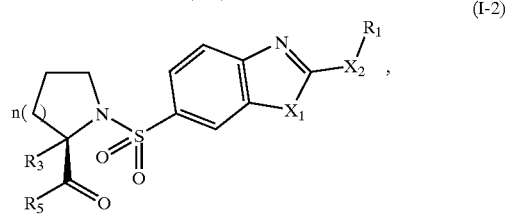

wherein n is an integer of 0 to 4.

4. A process for preparing a compound of claim 1, which comprises:
  (i) reacting sulfonyl halide(II) with compound(III) in an organic solvent in the presence of a base to give an intermediate compound(IV), wherein —C1 in Formula (II) refers to a halide;
  (ii) reacting the intermediate compound(IV) with R₄-L(L: reactive leaving group) in an organic solvent in the presence of a base to give an intermediate compound (V); and,
  (iii) hydrolyzing the intermediate compound(V) into a compound(I-3, R₅:OH), or further condensing the compound(I-3, R₅:OH) to prepare a compound(I-4, R₅:NHOH)

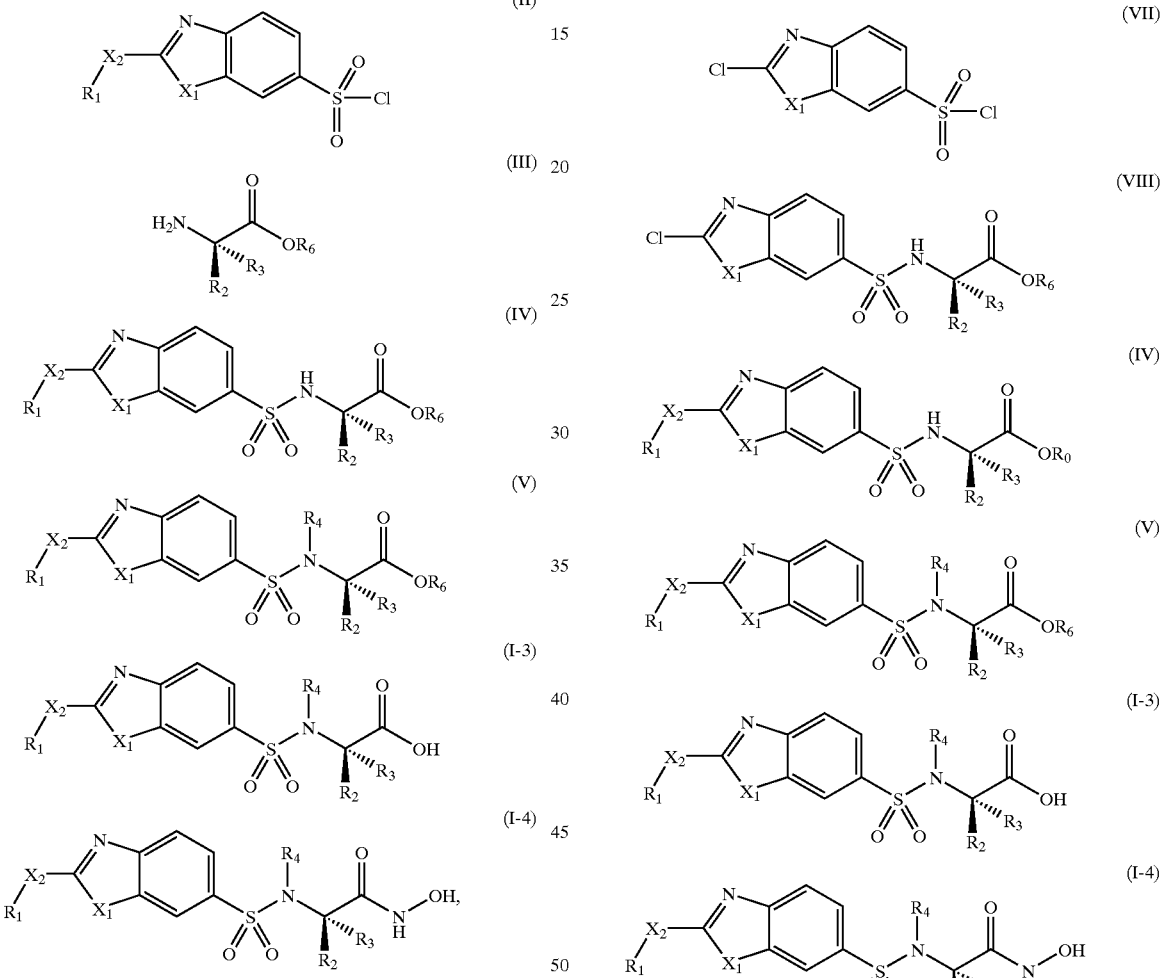

wherein R₆ is a substituent used as a protecting group of amino acid.

5. The process for preparing a compound represented as the general formula(I) of claim 4, wherein the hydrolysis in step(iii) is performed in the presence of a base.

6. A process for preparing a compound of claim 1, which comprises:
  (i) chlorosulfonylating a compound(VI) to give a compound(VII);
  (ii) reacting the compound(VII) with amino acid derivative(III) in an organic solvent in the presence of base to give an intermediate compound(VIII);
  (iii) heating the intermediate compound(VIII) and R₁—X₂H together at 70 to 80° C. in an organic solvent in the presence of base to give an intermediate compound(IV);
  (iv) reacting the intermediate compound(IV) with R₄-L (L: reactive leaving group) in an organic solvent in the presence of base to give an intermediate compound(V); and,
  (v) hydrolyzing the intermediate compound(V) into a compound (I-3, R5:OH), or further condensing the compound (I-3, R₅:OH) to prepare a compound(I-4, R5:NHOH),

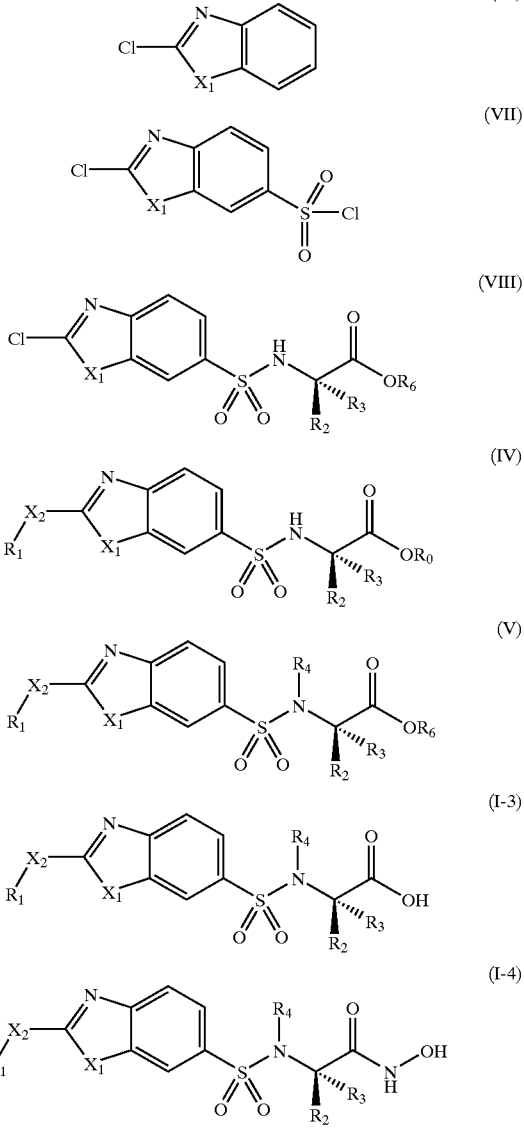

wherein R₆ is a substituent used as a protecting group of amino acid.

7. The process for preparing a compound represented as the general formula(I) of claim 6 wherein the hydrolysis in step(v) is performed in the presence of a base.

8. The process of claim 5 wherein the base comprises lithium hydroxide.

9. The process of claim 7 wherein the base comprises lithium hydroxide.

* * * * *